(12) United States Patent
Murison et al.

(10) Patent No.: US 10,081,531 B2
(45) Date of Patent: *Sep. 25, 2018

(54) ELECTRONIC VAPORISER SYSTEM

(71) Applicant: BEYOND TWENTY LTD., London (GB)

(72) Inventors: Ian Murison, London (GB); Stephen Marsh, London (GB)

(73) Assignee: BEYOND TWENTY LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/253,939

(22) Filed: Sep. 1, 2016

(65) Prior Publication Data

US 2017/0042237 A1 Feb. 16, 2017

Related U.S. Application Data

(63) Continuation-in-part of application No. 14/842,067, filed on Sep. 1, 2015, which is a continuation-in-part
(Continued)

(30) Foreign Application Priority Data

Feb. 28, 2014 (GB) .................................... 1403566.1
May 8, 2014 (GB) .................................... 1408173.1
(Continued)

(51) Int. Cl.
*A24F 47/00* (2006.01)
*B67D 7/36* (2010.01)
(Continued)

(52) U.S. Cl.
CPC .............. *B67D 7/36* (2013.01); *A24B 15/167* (2016.11); *A24F 15/14* (2013.01); *A24F 15/18* (2013.01);
(Continued)

(58) Field of Classification Search
CPC ....................................................... A24F 47/008
See application file for complete search history.

(56) References Cited

U.S. PATENT DOCUMENTS 3,612,363 A 10/1971 Carter
4,572,253 A 2/1986 Farmer et al.
(Continued)

FOREIGN PATENT DOCUMENTS

CN 201630238 U 11/2010
CN 202276832 U 6/2012
(Continued)

OTHER PUBLICATIONS

"Hidden Formaldehyde in E-Cigarette Aerosols", N. Engl. J. Med., 372:4, NEJM.org, Jan. 22, 2015, 392-394.

*Primary Examiner* — Eric Yaary
(74) *Attorney, Agent, or Firm* — Saul Ewing Arnstein & Lehr LLP

(57) ABSTRACT

An electronic cigarette vaporizer system includes a case and a vaporizer that is stored in the case; the system includes a non-contact sensor that detects release or withdrawal of the vaporizer from the case. When withdrawal of the vaporizer is detected, then the vaporizer electronic circuitry changes state, e.g. to a ready mode, or a pre-heating mode in which an inhalation detector is activated or to a heating mode, where an atomizing unit in the vaporizer is at least partly activated so that the vaporizer is fully heated when the first inhalation is taken.

23 Claims, 36 Drawing Sheets

Related U.S. Application Data of application No. 14/633,887, filed on Feb. 27, 2015, now Pat. No. 9,247,773.

(60) Provisional application No. 62/349,712, filed on Jun. 14, 2016, provisional application No. 62/045,701, filed on Sep. 4, 2014, provisional application No. 62/045,669, filed on Sep. 4, 2014, provisional application No. 62/045,692, filed on Sep. 4, 2014, provisional application No. 62/045,696, filed on Sep. 4, 2014, provisional application No. 62/045,651, filed on Sep. 4, 2014, provisional application No. 62/045,666, filed on Sep. 4, 2014, provisional application No. 62/045,657, filed on Sep. 4, 2014, provisional application No. 62/045,690, filed on Sep. 4, 2014, provisional application No. 62/045,680, filed on Sep. 4, 2014, provisional application No. 62/045,674, filed on Sep. 4, 2014, provisional application No. 62/045,688, filed on Sep. 4, 2014.

(30) Foreign Application Priority Data

| Jul. 23, 2014 | (GB) | 1413018.1 |
|---|---|---|
| Jul. 23, 2014 | (GB) | 1413019.9 |
| Jul. 23, 2014 | (GB) | 1413021.5 |
| Jul. 23, 2014 | (GB) | 1413025.6 |
| Jul. 23, 2014 | (GB) | 1413027.2 |
| Jul. 23, 2014 | (GB) | 1413028 |
| Jul. 23, 2014 | (GB) | 1413030.6 |
| Jul. 23, 2014 | (GB) | 1413032 |
| Jul. 23, 2014 | (GB) | 1413034.8 |
| Jul. 23, 2014 | (GB) | 1413036.3 |
| Jul. 23, 2014 | (GB) | 1413037.1 |
| Nov. 30, 2015 | (GB) | 1521110.5 |
| Mar. 1, 2016 | (GB) | 1603579.2 |
| Jun. 16, 2016 | (GB) | 1610531.4 |

(51) Int. Cl.

| B67D 7/02 | (2010.01) |
|---|---|
| B67D 7/78 | (2010.01) |
| F16K 25/00 | (2006.01) |
| F16K 24/04 | (2006.01) |
| B67D 7/62 | (2010.01) |
| H05B 3/14 | (2006.01) |
| B65D 85/00 | (2006.01) |
| B67D 7/42 | (2010.01) |
| A61M 11/04 | (2006.01) |
| A61M 15/06 | (2006.01) |
| B67D 7/14 | (2010.01) |
| B67D 7/34 | (2010.01) |
| G05B 19/416 | (2006.01) |
| G06F 21/44 | (2013.01) |
| H02J 7/00 | (2006.01) |
| H05B 1/02 | (2006.01) |
| A24F 15/14 | (2006.01) |
| A24F 15/18 | (2006.01) |
| B65D 83/00 | (2006.01) |
| B67D 7/54 | (2010.01) |
| F04B 43/04 | (2006.01) |
| F04B 49/06 | (2006.01) |
| G01R 31/28 | (2006.01) |
| H04M 1/725 | (2006.01) |
| G01K 13/02 | (2006.01) |
| A24B 15/16 | (2006.01) |
| G06Q 30/00 | (2012.01) |
| B65B 3/04 | (2006.01) |

(52) U.S. Cl.
CPC ......... *A24F 47/008* (2013.01); *A61M 11/042* (2014.02); *A61M 15/06* (2013.01); *B65D 83/0038* (2013.01); *B65D 85/70* (2013.01); *B67D 7/02* (2013.01); *B67D 7/0288* (2013.01); *B67D 7/145* (2013.01); *B67D 7/346* (2013.01); *B67D 7/42* (2013.01); *B67D 7/54* (2013.01); *B67D 7/62* (2013.01); *B67D 7/78* (2013.01); *F04B 43/046* (2013.01); *F04B 49/06* (2013.01); *F16K 24/04* (2013.01); *F16K 25/005* (2013.01); *G01K 13/02* (2013.01); *G01R 31/2825* (2013.01); *G05B 19/4166* (2013.01); *G06F 21/44* (2013.01); *H02J 7/0042* (2013.01); *H02J 7/0044* (2013.01); *H02J 7/0052* (2013.01); *H02J 7/0054* (2013.01); *H04M 1/7253* (2013.01); *H04M 1/72547* (2013.01); *H05B 1/0244* (2013.01); *H05B 3/141* (2013.01); *A61M 2205/3331* (2013.01); *A61M 2205/3368* (2013.01); *A61M 2205/3584* (2013.01); *A61M 2205/50* (2013.01); *A61M 2205/583* (2013.01); *A61M 2205/60* (2013.01); *A61M 2205/8206* (2013.01); *B65B 3/04* (2013.01); *G05B 2219/37371* (2013.01); *G06Q 30/016* (2013.01); *H02J 7/0063* (2013.01); *H05B 2203/021* (2013.01)

(56) References Cited

U.S. PATENT DOCUMENTS

| 4,702,397 | A | 10/1987 | Gortz et al. |
|---|---|---|---|
| 5,121,769 | A | 6/1992 | McCabe et al. |
| 5,332,125 | A | 7/1994 | Schmitkons |
| 5,751,320 | A | 5/1998 | Scheffelin et al. |
| 6,428,154 | B1 | 8/2002 | Kamiyama et al. |
| 6,637,430 | B1 | 10/2003 | Voges et al. |
| 2002/0112723 | A1 | 8/2002 | Schuster et al. |
| 2003/0225396 | A1 | 12/2003 | Cartledge |
| 2004/0159368 | A1 | 8/2004 | Eddins et al. |
| 2005/0016550 | A1 | 1/2005 | Katase et al. |
| 2005/0168540 | A1 | 8/2005 | Wilson et al. |
| 2005/0189275 | A1 | 9/2005 | Stewart et al. |
| 2005/0219302 | A1 | 10/2005 | Vogeley et al. |
| 2007/0045288 | A1 | 3/2007 | Nelson et al. |
| 2008/0230052 | A1 | 9/2008 | Montaser et al. |
| 2008/0239040 | A1 | 10/2008 | Umeda et al. |
| 2009/0126722 | A1* | 5/2009 | Sugita .................. A61K 9/0073 128/200.19 |
| 2009/0266358 | A1 | 10/2009 | Sacristan Rock et al. |
| 2009/0272379 | A1 | 11/2009 | Thorens et al. |
| 2010/0163063 | A1* | 7/2010 | Fernando .............. A24F 47/008 131/184.1 |
| 2010/0242975 | A1* | 9/2010 | Hearn ................... A24F 47/002 131/273 |
| 2010/0243754 | A1 | 9/2010 | Harris et al. |
| 2010/0243760 | A1 | 9/2010 | Birrenkott et al. |
| 2010/0313901 | A1 | 12/2010 | Fernando et al. |
| 2011/0036346 | A1 | 2/2011 | Cohen et al. |
| 2011/0120565 | A1 | 5/2011 | Saunders et al. |
| 2011/0226236 | A1 | 9/2011 | Buchberger et al. |
| 2011/0265806 | A1 | 11/2011 | Alarcon et al. |
| 2011/0279605 | A1 | 11/2011 | Borra et al. |
| 2011/0304468 | A1 | 12/2011 | Linsenmeyer et al. |
| 2012/0048266 | A1 | 3/2012 | Alelov et al. |
| 2012/0138162 | A1 | 6/2012 | Beaulieu et al. |
| 2012/0167906 | A1 | 7/2012 | Gysland et al. |
| 2012/0168977 | A1 | 7/2012 | Mazyar |
| 2012/0199663 | A1 | 8/2012 | Qiu et al. |
| 2012/0312313 | A1 | 12/2012 | Frija et al. |
| 2013/0046463 | A1* | 2/2013 | Bengtson ............... G01C 21/165 701/500 |
| 2013/0111882 | A1 | 5/2013 | Eriksson |

(56) References Cited

U.S. PATENT DOCUMENTS

| | | |
|---|---|---|
| 2013/0139894 A1 | 6/2013 | Fuhr et al. |
| 2013/0168880 A1* | 7/2013 | Duke .................. A24F 47/008 261/78.2 |
| 2013/0192615 A1 | 8/2013 | Tucker et al. |
| 2013/0220315 A1 | 8/2013 | Conley et al. |
| 2013/0255702 A1* | 10/2013 | Griffith, Jr. ........... A24F 47/008 131/328 |
| 2013/0284192 A1 | 10/2013 | Peleg et al. |
| 2013/0284194 A1 | 10/2013 | Newton et al. |
| 2013/0298905 A1* | 11/2013 | Levin .................. A24F 47/008 128/202.21 |
| 2013/0306064 A1 | 11/2013 | Thorens et al. |
| 2013/0306084 A1 | 11/2013 | Flick et al. |
| 2013/0319431 A1 | 12/2013 | Cyphert et al. |
| 2013/0319438 A1 | 12/2013 | Liu et al. |
| 2013/0327787 A1 | 12/2013 | Koltay et al. |
| 2013/0342157 A1 | 12/2013 | Liu et al. |
| 2014/0000638 A1 | 1/2014 | Sebastian et al. |
| 2014/0008452 A1 | 1/2014 | Iammatteo et al. |
| 2014/0020697 A1 | 1/2014 | Liu et al. |
| 2014/0060554 A1 | 3/2014 | Collett et al. |
| 2014/0096781 A1 | 4/2014 | Sears et al. |
| 2014/0123989 A1 | 5/2014 | Lamothe et al. |
| 2014/0123990 A1 | 5/2014 | Timmermans et al. |
| 2014/0166029 A1 | 6/2014 | Weigensberg et al. |
| 2014/0174459 A1 | 6/2014 | Burstyn et al. |
| 2014/0212334 A1 | 7/2014 | Klein et al. |
| 2014/0242213 A1 | 8/2014 | McCarty |
| 2014/0246035 A1 | 9/2014 | Minskoff et al. |
| 2014/0261491 A1* | 9/2014 | Hawes ................ A24F 47/008 131/328 |
| 2014/0270727 A1 | 9/2014 | Ampolini et al. |
| 2014/0283825 A1 | 9/2014 | Buchberger et al. |
| 2014/0299137 A1 | 10/2014 | Kieckbusch et al. |
| 2014/0299140 A1 | 10/2014 | Liu et al. |
| 2014/0299141 A1* | 10/2014 | Flick .................... H05B 1/0202 131/329 |
| 2014/0338685 A1 | 11/2014 | Amir |
| 2014/0345606 A1 | 11/2014 | Talon |
| 2014/0345635 A1 | 11/2014 | Rabinowitz et al. |
| 2014/0366898 A1 | 12/2014 | Bowen et al. |
| 2015/0007835 A1 | 1/2015 | Liu |
| 2015/0041345 A1 | 2/2015 | Kerkar |
| 2015/0053217 A1 | 2/2015 | Steingraber et al. |
| 2015/0114409 A1 | 4/2015 | Brammer et al. |
| 2015/0142387 A1 | 5/2015 | Alarcon et al. |
| 2015/0144145 A1 | 5/2015 | Chang et al. |
| 2015/0181945 A1 | 7/2015 | Tremblay |
| 2015/0196053 A1 | 7/2015 | Liu |
| 2015/0196058 A1 | 7/2015 | Lord |
| 2015/0208726 A1 | 7/2015 | Liu |
| 2015/0208731 A1 | 7/2015 | Malamud et al. |
| 2015/0245654 A1 | 9/2015 | Marsh et al. |
| 2015/0272216 A1 | 10/2015 | Xu et al. |
| 2015/0272217 A1 | 10/2015 | Chen |
| 2015/0289565 A1 | 10/2015 | Cadieux et al. |
| 2015/0305409 A1 | 10/2015 | Recio et al. |
| 2015/0313284 A1 | 11/2015 | Liu |
| 2015/0313287 A1 | 11/2015 | Lu et al. |
| 2015/0359263 A1 | 12/2015 | Bellinger |
| 2016/0050976 A1 | 2/2016 | Righetti |
| 2016/0057811 A1* | 2/2016 | Alarcon ............... H05B 1/0252 219/494 |
| 2016/0073692 A1 | 3/2016 | Alarcon et al. |
| 2016/0106936 A1 | 4/2016 | Kimmel |
| 2016/0128384 A1 | 5/2016 | Luciani et al. |
| 2016/0150824 A1 | 6/2016 | Marsh et al. |
| 2016/0157524 A1 | 6/2016 | Leon et al. |
| 2016/0198770 A1 | 7/2016 | Alarcon |
| 2016/0206000 A1* | 7/2016 | Lord .................... A24F 47/008 |
| 2016/0213066 A1 | 7/2016 | Borkovec et al. |
| 2016/0219933 A1 | 8/2016 | Henry, Jr. et al. |
| 2016/0271347 A1 | 9/2016 | Raichman et al. |
| 2016/0286860 A1 | 10/2016 | Flayler et al. |
| 2016/0345621 A1 | 12/2016 | Smith et al. |
| 2016/0353801 A1 | 12/2016 | Zinovik et al. |
| 2016/0360789 A1 | 12/2016 | Bramley et al. |
| 2016/0366939 A1 | 12/2016 | Alarcon et al. |
| 2017/0013883 A1 | 1/2017 | Han et al. |
| 2017/0020192 A1 | 1/2017 | Eveillard et al. |
| 2017/0042244 A1 | 2/2017 | Batista et al. |
| 2017/0071257 A1 | 3/2017 | Lin |
| 2017/0135401 A1 | 5/2017 | Dickens et al. |
| 2017/0215485 A1 | 8/2017 | Zitzke |
| 2017/0222468 A1 | 8/2017 | Schennum et al. |
| 2017/0238613 A1 | 8/2017 | Suess et al. |
| 2017/0334605 A1 | 11/2017 | Murphy et al. |

FOREIGN PATENT DOCUMENTS

| | | |
|---|---|---|
| CN | 202679020 U | 1/2013 |
| CN | 103914013 A | 7/2014 |
| CN | 203873004 U | 10/2014 |
| CN | 204232301 U | 4/2015 |
| CN | 204273244 U | 4/2015 |
| CN | 104783332 A | 7/2015 |
| DE | 102007011120 A1 | 9/2008 |
| EP | 1618803 A1 | 1/2006 |
| EP | 2047914 A | 4/2009 |
| EP | 2060397 A1 | 5/2009 |
| EP | 2201850 A1 | 6/2010 |
| EP | 2399636 A1 | 12/2011 |
| EP | 2468116 A1 | 6/2012 |
| EP | 2468118 A1 | 6/2012 |
| EP | 3020290 A1 | 5/2016 |
| EP | 3127439 A1 | 2/2017 |
| GB | 2507102 A | 4/2014 |
| GB | 2512325 A | 10/2014 |
| GB | 2512326 A | 10/2014 |
| GB | 2518598 A | 4/2015 |
| GB | 2523585 A | 9/2015 |
| GB | 2525725 A | 11/2015 |
| GB | 2525727 A | 11/2015 |
| GB | 2529629 A | 3/2016 |
| GB | 2529919 A | 3/2016 |
| GB | 2531830 A | 5/2016 |
| GB | 2534726 A | 8/2016 |
| GB | 2535239 A | 8/2016 |
| JP | H09149781 A | 6/1997 |
| KR | 20110009056 U | 9/2011 |
| KR | 1020130091473 A | 8/2013 |
| WO | 2005/025654 A | 3/2005 |
| WO | 2009001078 A2 | 12/2008 |
| WO | 2010/073018 A1 | 7/2010 |
| WO | 2010073122 A1 | 7/2010 |
| WO | 2011026846 A1 | 3/2011 |
| WO | 2011095781 A1 | 8/2011 |
| WO | 2013020220 A4 | 3/2013 |
| WO | 2013/060781 A1 | 5/2013 |
| WO | 2013/098397 | 7/2013 |
| WO | 2014/040988 A1 | 3/2014 |
| WO | 2014/054035 A1 | 4/2014 |
| WO | 2014/102091 A1 | 7/2014 |
| WO | 2014/190079 A2 | 11/2014 |
| WO | 2015028814 A1 | 3/2015 |
| WO | 2015035741 A1 | 3/2015 |
| WO | 2015051538 A1 | 4/2015 |
| WO | 2015/063126 A1 | 5/2015 |
| WO | 2015/091258 A1 | 6/2015 |
| WO | 2015/127429 A4 | 8/2015 |
| WO | 2015/128667 A1 | 9/2015 |
| WO | 2015/149242 A1 | 10/2015 |
| WO | 2015/165059 A1 | 11/2015 |
| WO | 2015/179002 A2 | 11/2015 |
| WO | 2015179641 A1 | 11/2015 |
| WO | 2016/009202 A1 | 1/2016 |
| WO | 2016/040575 A1 | 3/2016 |
| WO | 2016/096728 A1 | 6/2016 |
| WO | 2016/096780 A1 | 6/2016 |
| WO | 2016/150922 A2 | 9/2016 |

* cited by examiner

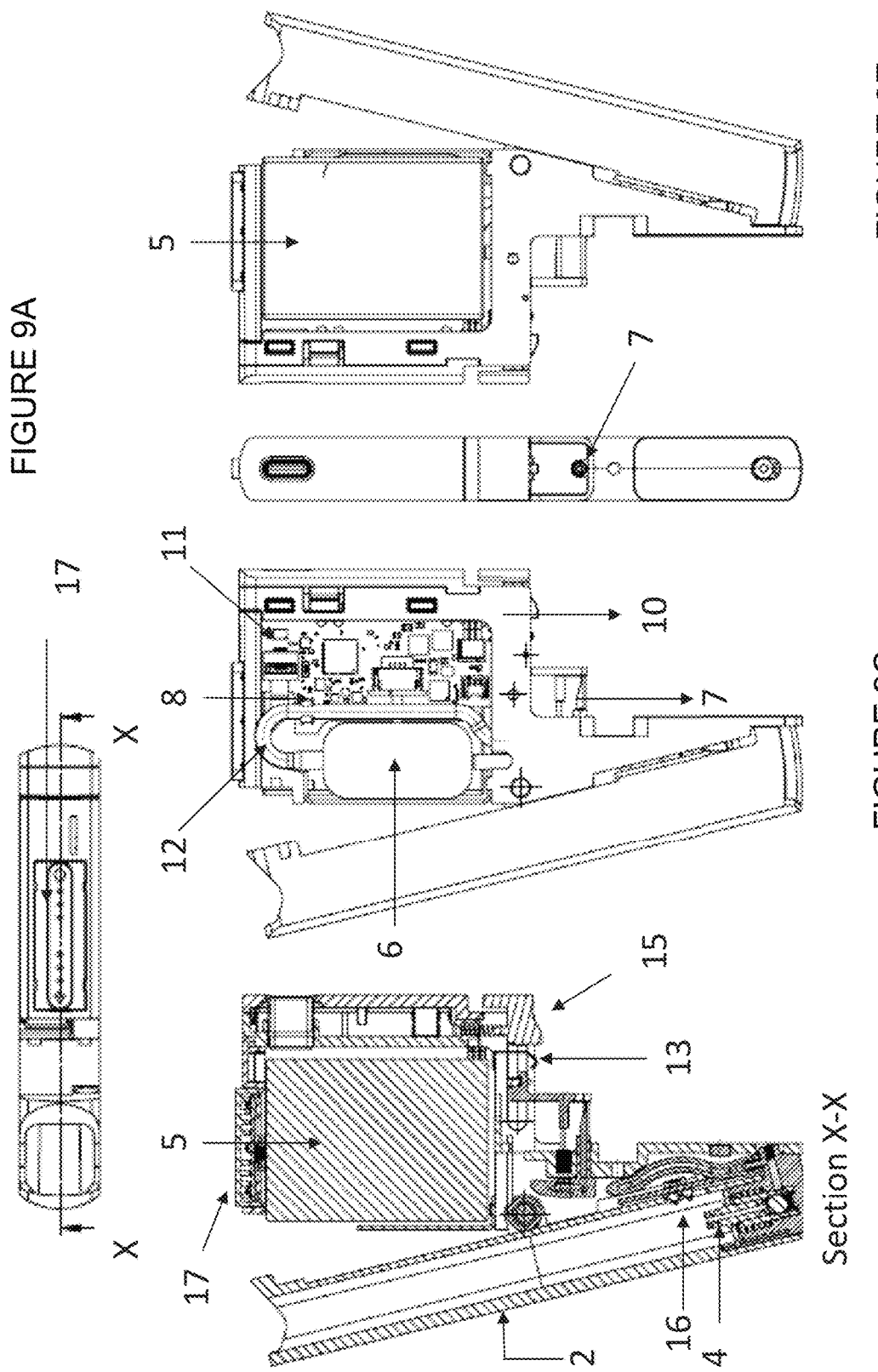

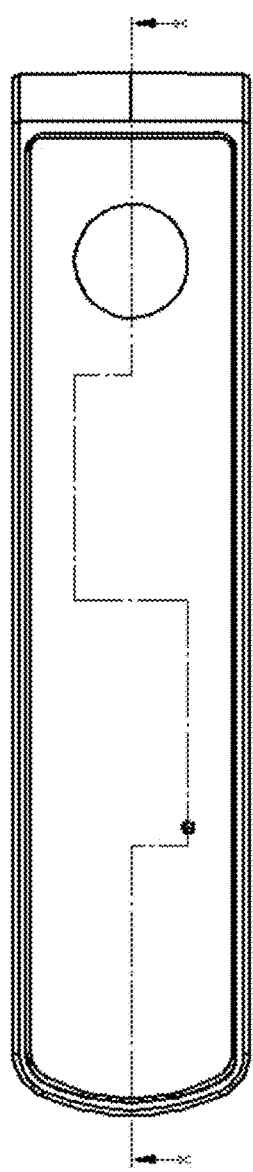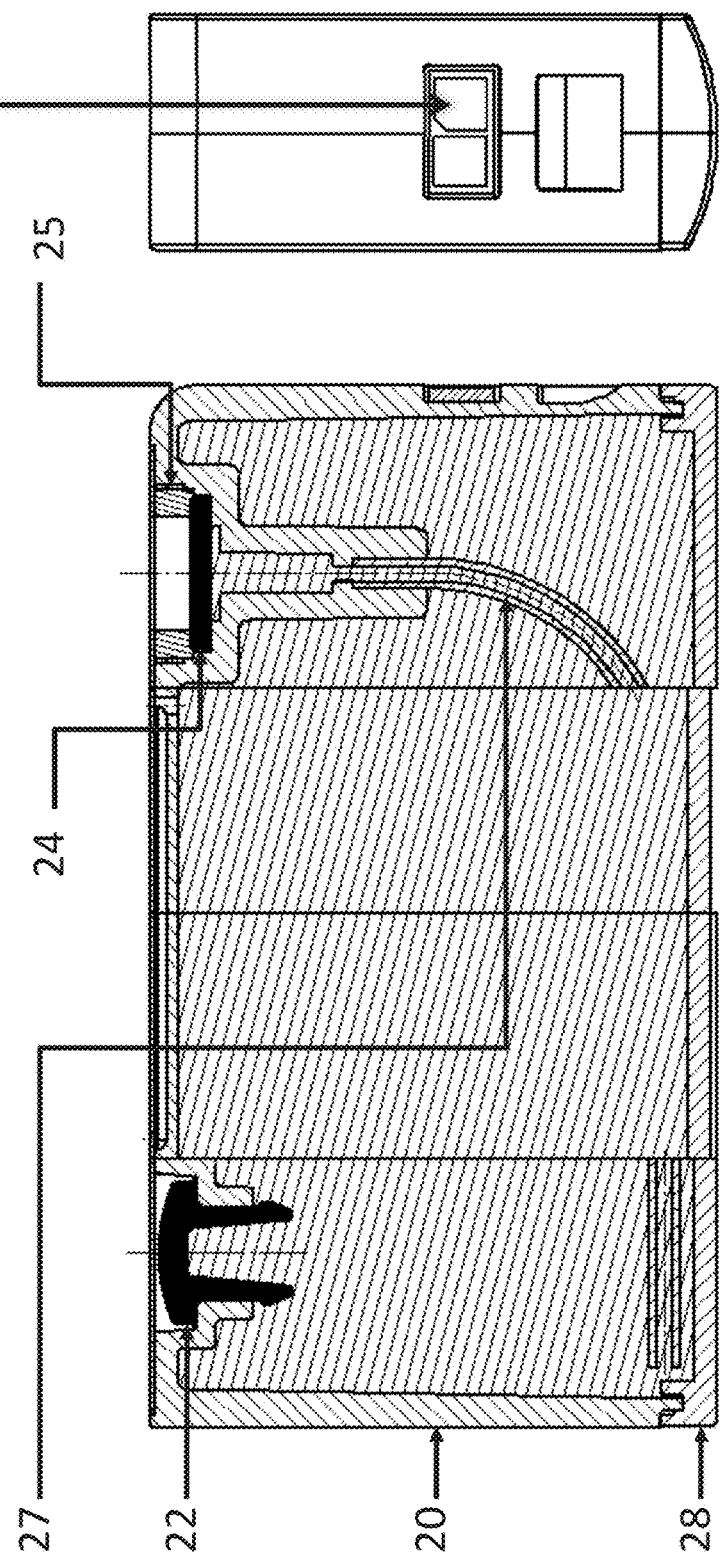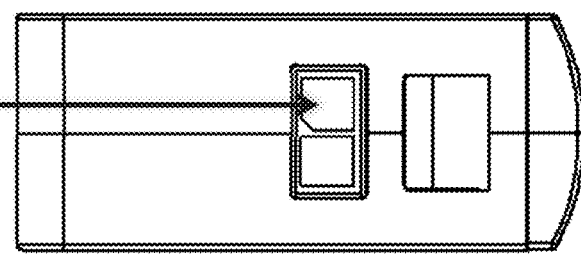
FIGURE 11A
FIGURE 11B
FIGURE 11C

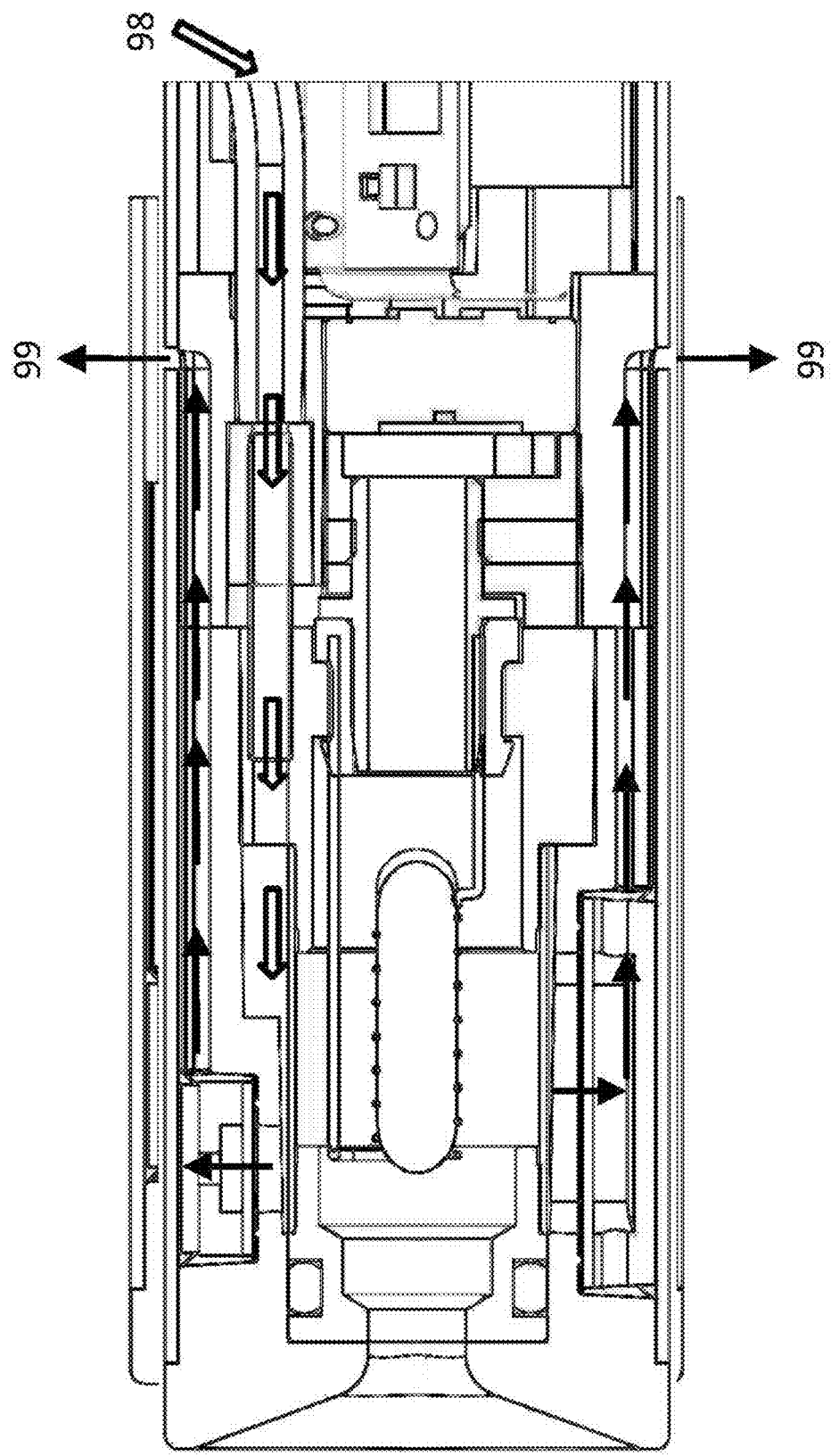

Section X-X

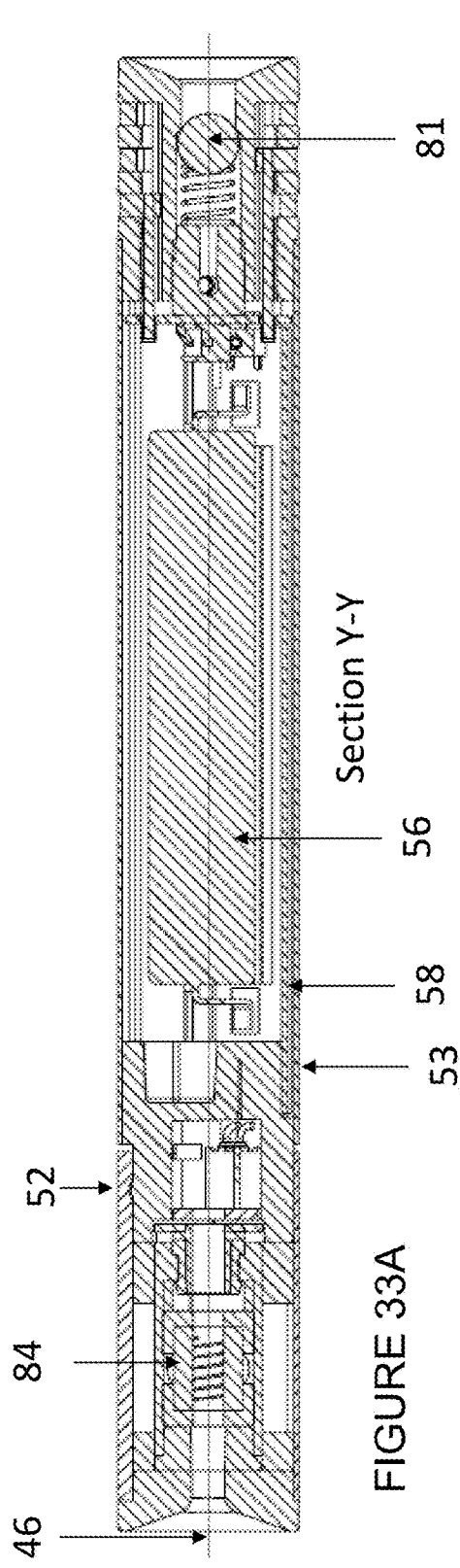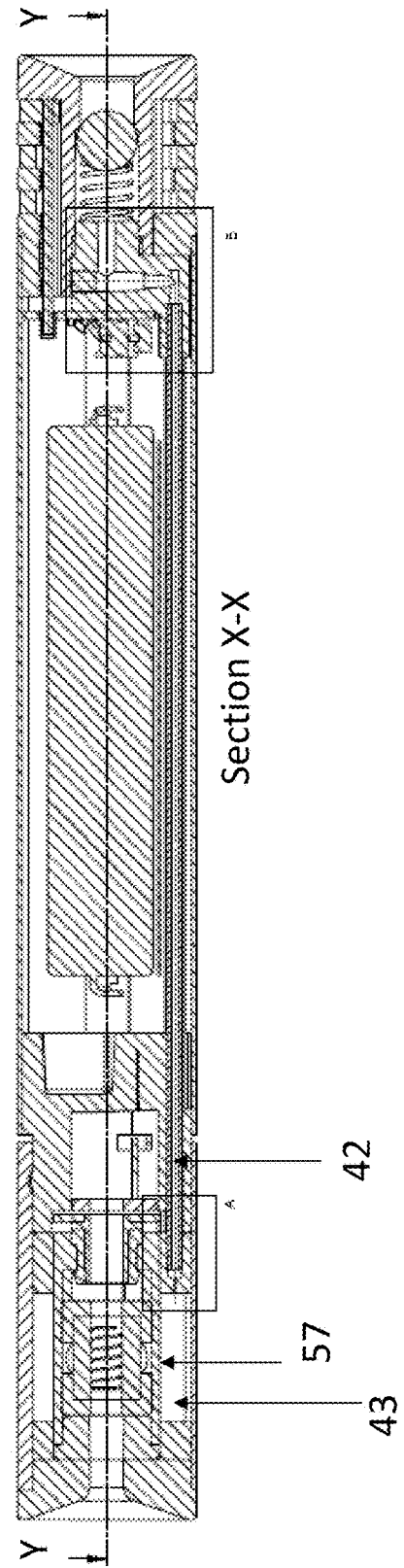

ELECTRONIC VAPORISER SYSTEM

CROSS-REFERENCE TO RELATED APPLICATIONS

This application is a continuation-in-part of U.S. application Ser. No. 14/842,067, filed Sep. 1, 2015, which is a continuation-in-part of U.S. application Ser. No. 14/633,887, filed Feb. 27, 2015, which is based on and claims priority to UK Application No. 1403566.1, filed Feb. 28, 2014; UK Application No. 1408173.1, filed May 8, 2014; UK Application No. 1413018.1, filed Jul. 23, 2014; UK Application No. 1413019.9, filed Jul. 23, 2014; UK Application No. 1413021.5, filed Jul. 23, 2014; UK Application No. 1413025.6, filed Jul. 23, 2014; UK Application No. 1413027.2, filed Jul. 23, 2014; UK Application No. 1413028.0, filed Jul. 23, 2014; UK Application No. 1413030.6, filed Jul. 23, 2014; UK Application No. 1413032.0, filed Jul. 23, 2014; UK Application No. 1413034.8, filed Jul. 23, 2014; UK Application No. 1413036.3, filed Jul. 23, 2014; UK Application No. 1413037.1, filed Jul. 23, 2014; U.S. Provisional Application No. 62/045,651, filed Sep. 4, 2014; U.S. Provisional Application No. 62/045,657, filed Sep. 4, 2014; U.S. Provisional Application No. 62/045,666, filed Sep. 4, 2014; U.S. Provisional Application No. 62/045,669, filed Sep. 4, 2014; U.S. Provisional Application No. 62/045,674, filed Sep. 4, 2014; U.S. Provisional Application No. 62/045,680, filed Sep. 4, 2014; U.S. Provisional Application No. 62/045,688, filed Sep. 4, 2014; U.S. Provisional Application No. 62/045,690, filed Sep. 4, 2014; U.S. Provisional Application No. 62/045,692, filed Sep. 4, 2014; U.S. Provisional Application No. 62/045,696, filed Sep. 4, 2014; and U.S. Provisional Application No. 62/045,701, filed Sep. 4, 2014. This application is also based on, and claims priority to U.S. Application No. 62/349,712, filed Jun. 14, 2016, GB Application No. 1521110.5, filed Nov. 30, 2015; GB Application No. 1603579.2, filed Mar. 1, 2016; and GB Application No. 1610531.4, filed Jun. 16, 2016, the entire contents of each of which being fully incorporated herein by reference.

BACKGROUND OF THE INVENTION

1. Field of the Invention

The field of the invention relates to an electronic vaporiser system. One example of an electronic vaporiser system is an e-cigarette, also known as a vapestick, inhalator, modding kit, personal vaporiser (PV), advanced personal vaporiser (APVs) or electronic nicotine delivery system (ENDS). In this specification, we will typically use 'PV' or 'vaporiser' as the generic term for an electronic vaporiser, namely the unit that the user actually places to their lips and inhales from. An electronic vaporiser system includes this unit. An electronic vaporiser can deliver nicotine as well as other substances, and can be a consumer electronics device, or a medicinally approved nicotine drug delivery system.

A PV, in the e-cigarette context, vapourises 'e-liquid' or a vaping substance to produce a non-pressurised vapour or mist for inhalation for pleasure or stress-relief, replicating or replacing the experience of smoking a cigarette. An 'e-liquid' or vaping substance is a liquid (or gel or other state) from which vapour or mist for inhalation can be generated and whose primary purpose is to deliver nicotine or other compounds, such as medicines. PVs are therefore mass-market consumer products that can be equivalent to cigarettes, and are then typically used by smokers as part of a cigarette reduction or cessation program. The main ingredients of e-liquids for vaping are usually a mix of propylene glycol and glycerine. E-liquids can include various flavourings and also come with varying strengths of nicotine; users on a nicotine reduction or cessation program can hence choose decreasing concentrations of nicotine, including at the limit zero concentration nicotine e-liquid. The term 'e-liquid' will be used in this specification as the generic term for any kind of vaping substance.

2. Description of the Prior Art

Conventional designs of re-fillable e-cigarette are somewhat complex because re-filling with e-liquid generally requires the user to unscrew the e-cigarette and to then manually drip onto an atomizing coil a small quantity of e-liquid. The overall user interaction with conventional re-fillable e-cigarettes (covering all aspects of how the user controls, re-fills, re-charges and generally interacts with the device) can therefore be complex and this is reflected in their design, which is often rather technical, with various control buttons. The overall user interaction is rarely intuitively clear. This is very different from the straightforward and simple (and, to smokers, deeply attractive) ritual of opening a pack of conventional cigarettes and lighting up. The complex user interaction that characterizes conventional refillable e-cigarettes has none of the simplicity or attractive ritual of opening a packet of cigarettes and lighting up.

Designing an e-cigarette system that replicates the simplicity of a conventional cigarette is a considerable challenge but is we believe key to the mass-market adoption of e-cigarettes by smokers, and is hence key to delivering on their considerable public health potential.

SUMMARY OF THE INVENTION

An electronic cigarette vaporiser system includes a case and a vaporiser that is stored in the case; the system includes a non-contact sensor that detects release or withdrawal of the vaporiser from the case. When withdrawal of the vaporiser is detected, then the vaporiser electronic circuitry changes state, e.g. to a ready mode, or a pre-heating mode in which an inhalation detector is activated or to a heating mode, where an atomising unit in the vaporiser is at least partly activated so that the vaporiser is fully heated when the first inhalation is taken.

BRIEF DESCRIPTION OF THE DRAWINGS

The invention will be described with reference to the drawings:

FIGS. 9A-9E are top, right-side cross-section, right, rear, and left views, respectively, of the major components in the case.

FIGS. 11A-11C are top, side cross-section, and front views, respectively of the major components in the cartridge for the electronic cigarette vaporiser system.

FIG. 19A is a cross-section side view of the air pressure equalization valve and atomising unit in the vaporiser, showing the air flow pattern.

FIG. 33A-33B are cross-sectional views of a vaporiser which uses a ceramic cell atomizing unit.

KEY TO INTEGERS USED IN THE FIGURES

Figure 1:
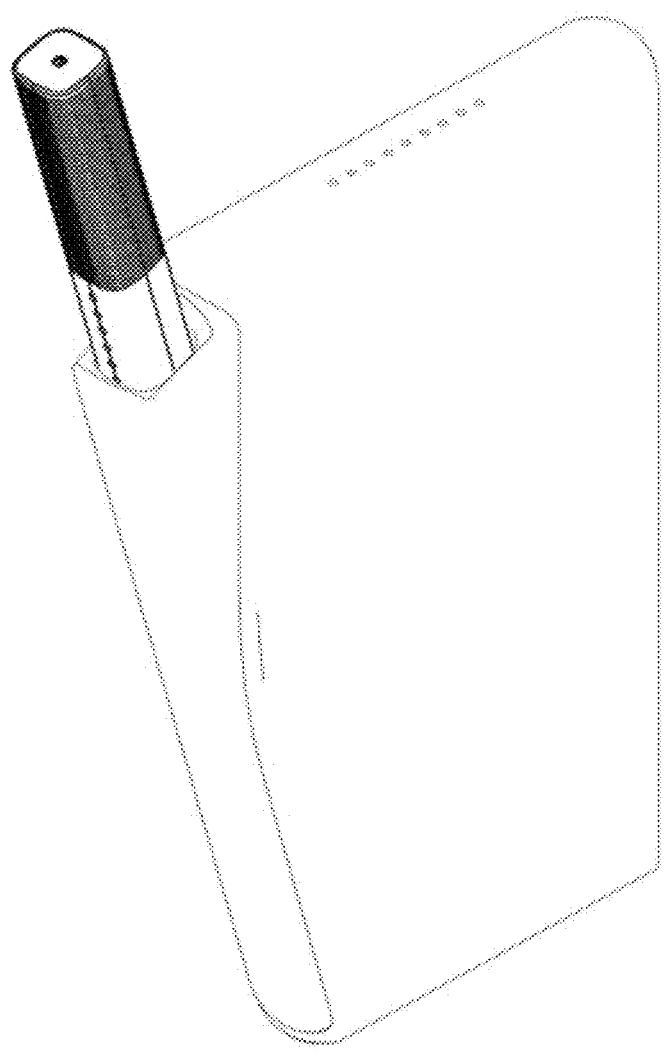
FIG. 1 is a perspective view of an electronic cigarette vaporiser case with a vaporiser partially extending from the case.

| Integer | Feature |
|---|---|
| 1 | The PV or vaporiser |
| 2 | Hinged PV holder |
| 3 | E-liquid cartridge or parent reservoir |
| 4 | Filling stem in the case |
| 5 | Main battery in the case |
| 6 | Piezo-electric micro pump in the case |
| 7 | Needle in the case that punctures the septum in the cartridge |
| 8 | Infra-red sensor placed around the e-liquid inlet tube feeding the piezo-pump |
| 9 | Left blank |
| 10 | Chassis assembly |
| 11 | PCB assembly board |
| 12 | e-liquid inlet tube feeding the piezo-pump |
| 13 | Data contact to read/write to security/authenticator chip 32 on the cartridge |
| 14 | Case assembly |
| 15 | Trigger latch assembly |
| 16 | Power and data contacts in the case and that engage with electrical contacts in the PV |
| 17 | Display panel on top of the case |
| 18 | Left blank |
| 19 | Left blank |
| 20 | Cartridge body |
| 21 | Cartridge inlet aperture, used for filling |
| 22 | Bung to seal the cartridge inlet aperture, |
| 23 | e-liquid outlet aperture |
| 24 | Septum that seals the e-liquid aperture but can be punctured by needle 7 in the case |
| 25 | Sealing ring for the septum 24 |
| 26 | Adhesive, tamper evident strip for the cartridge |
| 27 | E-liquid scavenger tube in the cartridge |
| 28 | Cartridge lid with PTFE porous membrane 31 welded to it |
| 29 | Air hole in the cartridge lid |
| 30 | Plenum chamber |
| 31 | PTFE air-porous but e-liquid impermeable membrane - allows air to vent but retains e-liquid |
| 32 | Security chip or authenticator |
| 33 | Left blank |
| 34 | Left blank |
| 35 | Cotton 'Z' shaped wick |
| 36 | Wire heating element |
| 37 | Coil assembly |
| 38 | Metal tube that encloses the coil assembly |
| 39 | Body that closes off one end of the metal tube 38 |
| 40 | End-cap that closes off the other end of the metal tube 38 |
| 41 | 'O' ring that seals the end-cap 40 |
| 42 | Stainless steel feed pipe that transfers e-liquid during pumping to the reservoir 44 around the metal tube 38 |
| 43 | Atomizing chamber inside the coil assembly 37 |
| 44 | Reservoir around the metal tube 38 |
| 45 | Air inlet |
| 46 | Vapour outlet aperture |
| 47 | Front seal tip |
| 48 | Silicone rubber stopper |
| 49 | Back seal |
| 50 | Fully assembled wick and coil assembly |
| 51 | Tip tube |
| 52 | Coil holder and mouthpiece, removable from main tube of the PV and assembled into tube/PV tip 53 |
| 53 | Tube - PV tip into which the coil holder assembles into |
| 54 | E-liquid filling assembly in the PV, including a check valve |
| 55 | Chassis within PV tube 53 |
| 56 | PV battery |
| 57 | e-liquid inlet aperture (2 mm diameter) in tube 38 |
| 58 | PCB in the PV |
| 59 | Air-flow sensor in the PV |
| 60 | Power wire in the PV |
| 61 | Electrically insulating spacer |

| Integer | Feature |
| --- | --- |
| 62 | Power plate or conductor providing power to the atomizing unit |
| 63 | Electrically insulating spacer |
| 64-69 | Left blank |
| 70 | Check valve body for e-liquid filling |
| 71 | Power ring, engaging with power source in the case |
| 72 | Insulating ring |
| 73 | Second power ring |
| 74 | Insulating ring |
| 75 | Third power ring |
| 76 | Electrical contact pin |
| 77 | Electrical contact pin |
| 78 | Electrical contact pin |
| 79 | Spring guide for the spring 80 that biases the stop valve |
| 80 | Spring that biases the stop valve |
| 81 | Stainless steel ball that acts as the stop valve |
| 82 | Seat for the stainless steel ball stop valve 81 |
| 83 | Filing stem or spigot in the case that pushes up against the stainless steel ball 81 in the PV |
| 84 | Cylindrical ceramic cell |
| 85 | Silicone cap |
| 86 | Silcone cap |
| 87 | Power bush |
| 88 | Heating wire wound inside the cylindrical ceramic cell |
| 89 | Front tip |
| 90 | Rounded rectangle air-permeable membrane in the mouthpiece 52 |
| 91 | Slug that secures air-permeable membrane 90 |
| 92 | Circular air-permeable membrane in the mouthpiece 52 |
| 93 | Slug that secures air-permeable membrane 92 |
| 95 | Bead against which each slug sits |
| 96 | Air vent channel leading from rounded rectangle air-permeable membrane 90 |
| 97 | Air vent channel leading from circular air-permeable membrane 92 |
| 98 | e-liquid path into the atomizing unit |
| 99 | Air path from each air-permeable membrane |
| 100 | The case |

DETAILED DESCRIPTION

We will now describe an implementation of the invention in the following 4 sections:

Section A: An introduction to the entire system from the user experience perspective Section B: Overview of some key components in the system Section C: A concise list of the key features Section D: A more detailed discussion of these key features Note that the majority of these features are not the invention; the claims define the invention.

Section A: An Introduction to the Entire System from the User Experience Perspective We will now walk through a high level view of the entire electronic vaporiser system that implements this invention from the user experience perspective. Reference may be made to WO 2015/128665, the contents of which are incorporated by reference.

Figure 2:
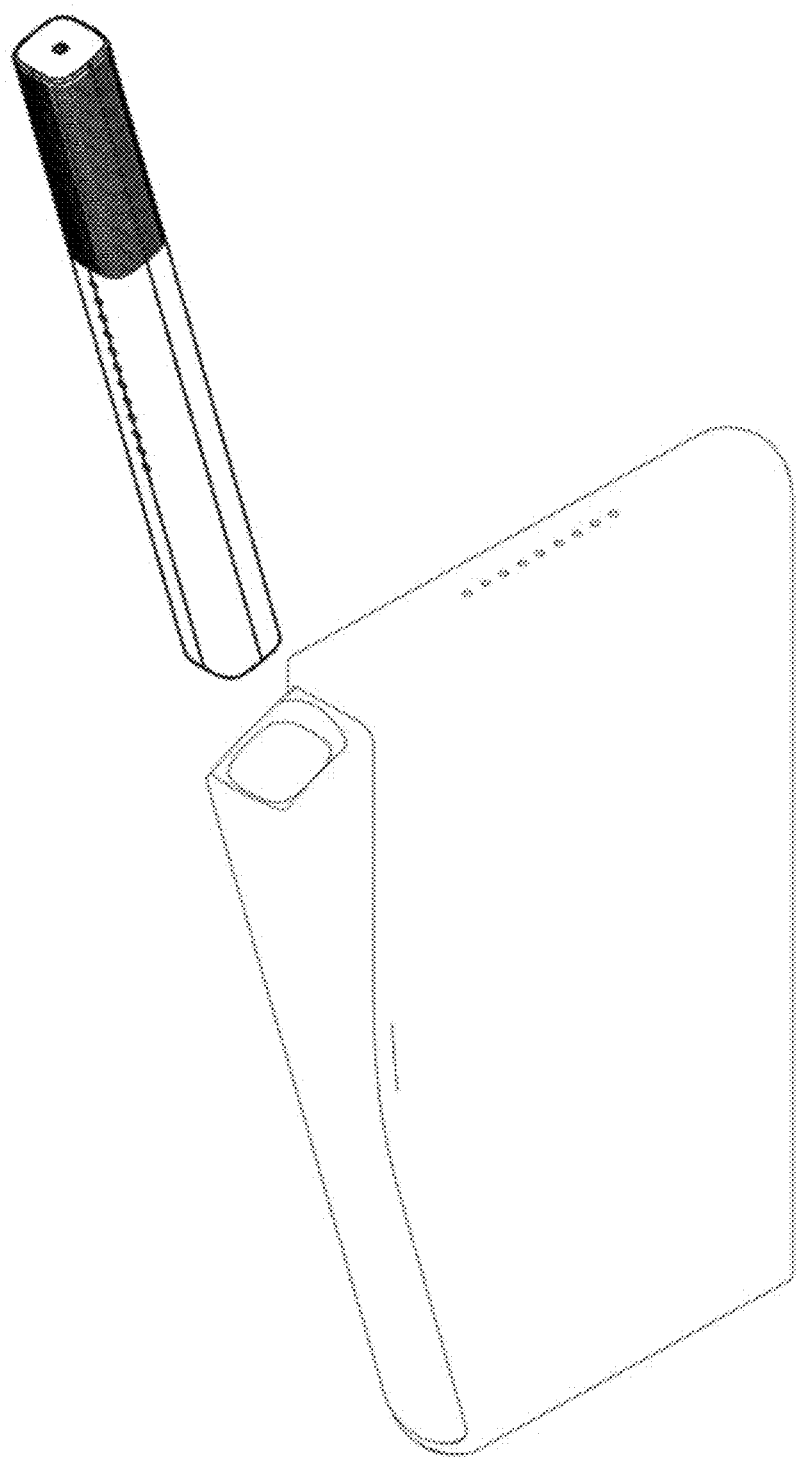
FIG. 2 is a perspective view of the electronic cigarette vaporiser case with a vaporiser fully withdrawn from the case

FIGS. 1 and 2 shows a perspective view of an electronic vaporiser e-cigarette system that implements the invention. The system includes a case that (i) stores an electronic vaporiser PV, and (ii) also re-fills the PV with e-liquid from a small, 10 mL, e-liquid closed-cartridge that the user has slotted into the case, and (iii) also re-charges the battery in the PV. Hence, when the PV is withdrawn from the case, as shown in FIG. 2, the electronic vaporiser PV is ready for use, and (depending on how long it has been stored in the case for) it will also have a full reservoir of e-liquid and a fully charged battery). Re-filling the PV with e-liquid and re-charging the battery in the PV occurs automatically whenever the PV is inserted back into the case.

The PV includes a series of 6 LEDs along one face. All the LED lights illuminate at the start of a vaping 'session' and go out (with the light furthest from the vapor going out first) indicating the amount left in the vaporiser. The session lasts the typical amount of a cigarette (8 to 10 puffs). When all the lights go out, you have to return the vaporiser to the case to have another vaping session. This vaping session is typically of equal duration to a standard cigarette and replicates the well understood behaviours, gestures and cues of smokers. Conventional re-fillable e-cigarettes often have a tank that stores the equivalent of 5 or 10 cigarettes and because they offer no clear beginning and end to a vaping session in a way that corresponds to smoking a normal cigarette, it is easy to consume excess nicotine. It is easier to regulate nicotine consumption (and hence reduce it) using our design of vaporizer because of the way the LEDs progressively extinguish in a way that corresponds to smoking a single cigarette.

The brightness of the LEDs is adjusted according to ambient light intensity (e.g. the LEDs dim automatically in low light), and reduces if in 'discrete' mode ('Discrete' mode enables a user to vape discretely—e.g. with a reduced volume of vapour and with dimmed or possibly no LED lights illuminated).

Unlike a conventional refillable e-cigarette, the PV includes no physical buttons to push in order to operate the PV: it is therefore much closer to a conventional cigarette than other e-cigarettes, which generally include multiple control buttons—something that many conventional smokers find off-putting. Since a key objective for this product is to benefit public health by appealling to smokers so that they can reduce or quit smoking, an over-riding design principle is to make the product as simple as possible, even though it is a refillable device, with the device replicating the form factor, rituals, behaviours, cues and gestures of conventional smoking. This makes the product appealing to established smokers. For example, the PV can be easily held between two fingers, just like a conventional cigarette—something that is impossible with a conventional refillable e-cigarette that typically includes a large and bulky battery pack.

With the PV stored in its case, full re-filling with e-liquid takes typically 30 seconds to 90 seconds. Generally, the PV's battery will not be fully discharged during a vaping session; the PV is meant to be stored in the case and hence will be regularly topped up. A full charge of the PV's battery might take 1 hour or more, but a top up from say 90% capacity to a full 100% might take a few minutes. Consequently, in a typical useage scenario, a vaper might use the product for vaping the equivalent of a single cigarette, and then replace the PV into the case for an hour or more. Whenever the user retrieves the PV from the case, it is then fully charged with power and with e-liquid, replicated taking a fresh cigarette out its pack.

The end or tip of the PV, which includes the heating element, is a user-replaceable component; the user can pull the tip off and replace it with a new one. This is useful if the sort of heating element (e.g. coil and wick) in the tip lasts 2 or 3 months or less, or if the tip has been damaged.

The 10 mL cartridge in the case stores e-liquid equivalent to approximately 50-100 cigarettes; it is readily replaced if the user needs to replace the cartridge because he has run out of e-liquid or if the user wishes to try a different flavor or strength of e-liquid.

The cartridge is 'closed', meaning that it is sealed after authorized filling with e-liquid and cannot then be re-filled by the end-user: this ensures compliance with safety regulations (such as the European Tobacco Products Regulation 2014/40/EU) and ensures that only the highest quality e-liquid from an authorized source is present in the cartridge. Also, because filling of the PV with e-liquid takes place when the PV is inside the case, there is minimal risk of leakage, in contrast with 'open tank' systems, which all need to be manually re-filled. Further, filling is entirely automatic, so the user does not have to disassemble the PV for filing; disassembly is normally required for re-fillable electronic vaporisers. Finally, because the main battery (a 1400 mAh battery) and the main e-liquid reservoir (10 mL) is in the portable carrying case, that means that the PV itself needs only a relatively small battery (120 mAh) and relatively small e-liquid reservoir (approx. 0.4 mL total volume; we fill approximately 0.2 mL of this volume with e-liquid): this in turn means that the PV itself can be much smaller than conventional re-fillable electronic vaporisers, and in fact be similar in size and shape to a conventional cigarette, and yet have the performance of a device with a much larger battery and e-liquid reservoir. This makes the electronic vaporiser system much more appealing to smokers who wish to stop smoking and start vaping (e.g. for health reasons, because vaping does not make you smell or turn your fingers and teeth yellow) but are put off by conventional designs of re-fillable electronic vaporiser which are often bulky and unattractive. As noted above, a slim, cigarette sized and shaped vaporizer can be held in the same was as a cigarette and the user can hence replicate the familiar gestures and behaviours associated with conventional smoking.

By having a PV that is cigarette sized (approximately 9.7 cm in length, and 1 cm in width) and shaped (approximately cylindrical, or tubular with rounded corners) and is withdrawn from a case that is similar in size to a cigarette packet, this system mimics the behavioural or ritualistic aspects smoking that are very appealing to smokers—nicotine reduction therapies that ignore these aspects are much less attractive to smokers and hence much less likely to lead to compliance with a smoking cessation program. This system hence replicates the rituals of handling an object similar in size to a packet of twenty cigarettes, of opening that packet and withdrawing a cigarette; and the tactile familiarity of holding a cigarette sized object and inhaling from it. This combination is we believe key to the large-scale consumer adoption of e-cigarettes. One objective for this product is to provide a vaping system that is a significantly more effective smoking cessation tool than conventional e-cigarettes.

To re-cap, the electronic vaporiser system shown in FIGS. 1 and 2 gives a PV with the compactness and form factor of a conventional cigarette, but with the vaping performance of a much larger and bulkier re-fillable PV, such as an 'open tank' system, because it (i) still accesses a large and powerful battery, but this battery is now displaced to the case and is not part of the vaporiser and (2) still accesses a large, 10 mL e-liquid tank, but this is now inside the case and is not part of the vaporiser.

Full dimensions are as follows:
Vaporiser: (mm. width×depth×height) 10×10×97 mm
Vaporiser replaceable tip: 10×10×24 mm
Case: 15.5×63×117.5 mm
Capsule: 12.5×26.9×55 mm.

Figure 3:
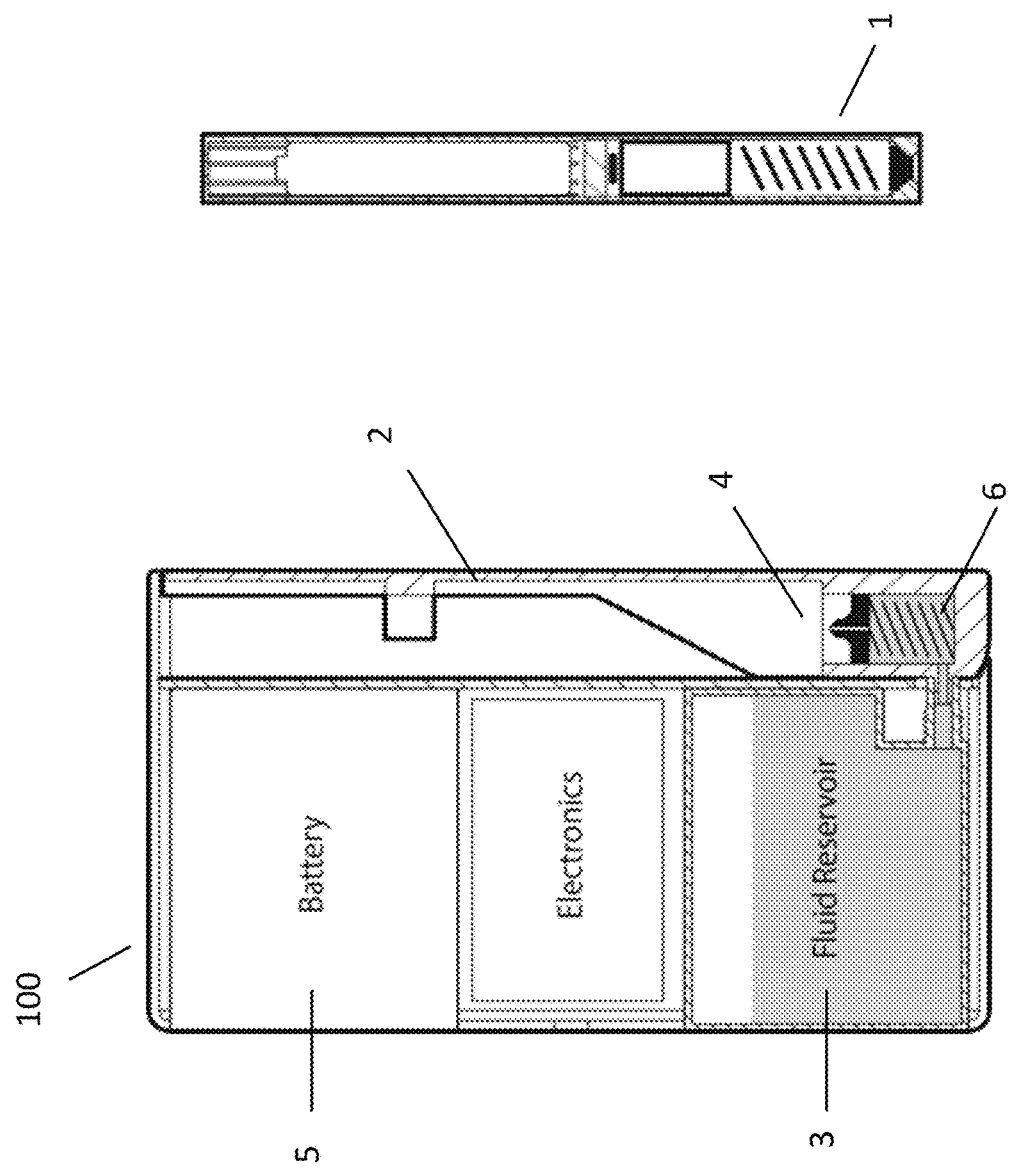
FIGS. 3A and 3B and 4A and 4B are cross-sectional schematic views of an electronic cigarette vaporiser system.

FIG. 3 is a schematic cross-section of the system, showing the key components. The case 100 includes a hinged PV holder 2, a battery 5, similar to a mobile phone battery, and a removable cartridge 3 that stores e-liquid. E-liquid is delivered from the cartridge 3 using a piezo-electric micro-pump 6 inside the case 100; e-liquid passes into the PV through a filling stem 4. The piezo-pump 6 could be mounted on the main electronics board in the case 100, or the base of the hinged PV holder 2, or be integrated into the cartridge 3, or even inside the PV itself.

Figure 4:
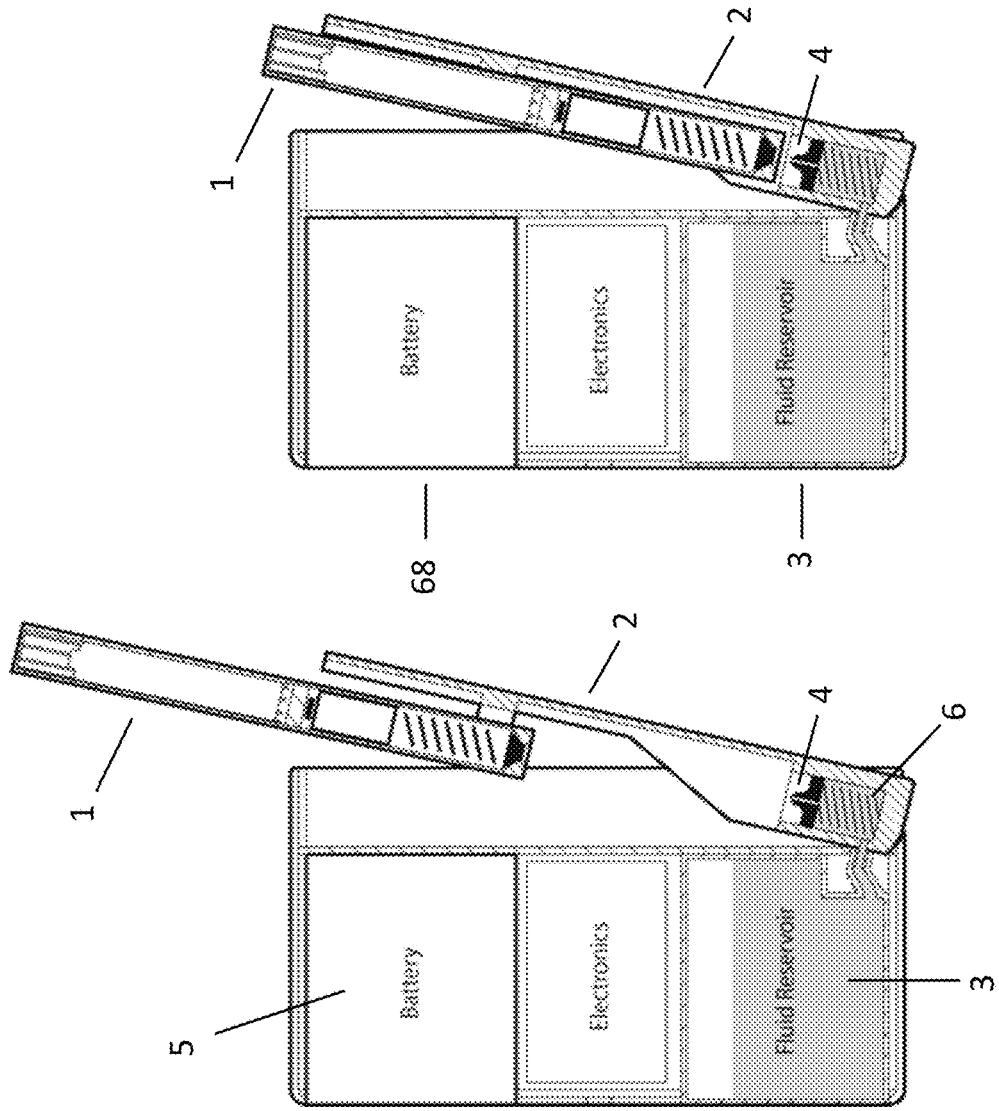

As shown in FIG. 4, the electronic vaporiser PV 1 slides in and out from a hinged holder 2 in the re-fill and re-charge case 100; when the PV 1 is stored into the case 100, the hinged holder 2 is closed, fully protecting the PV and ensuring that there is no real possibility of leakage of e-liquid from the PV into, e.g. a pocket or bag, unlike conventional electronic vaporiser systems.

When the PV 1 is fully inserted into the holder 2 then the filing stem 4 in case 100 protrudes into an aperture in the PV; when the case is fully closed and the user touches a control button, panel or switch in the case, or a fully automated mechanism is triggered, then the piezo-electric micro-pump 6 in the case 100 activates and pumps a metered amount of e-liquid (typically 0.2 mL) into the PV, typically to fill up a small 0.2 mL-0.6 mL e-liquid reservoir in the PV itself. 0.2 mL is the approximate quantity corresponding to a single cigarette, although this quantity is highly variable and depends on many different factors. In any event, a 0.4 mL reservoir should generally be equivalent to several cigarettes. It is also possible to design the PV with much larger reservoirs, e.g. 2 mL or higher, but there are user experience advantages to the PV being broadly equivalent to a small number of cigarettes, possibly just a single cigarette.

The pump 6 stops pumping when the required amount of e-liquid has been transferred. The PV can then be kept stored in the case, and a small battery in the PV is then re-charged by the main battery in the case whilst the PV is being stored. When the holder 2 is hinged open, with a trigger action (i.e. with the user pulling in the base of the hinged holder 2), then the PV 1 is gently and automatically lifted up a few mm from the holder using an ejection mechanism (e.g. magnetic or spring based) so the user can easily extract it. The PV 1 is then like a completely fresh electronic vaporiser at this time—fully re-filled with e-liquid and its battery fully topped up with charge. Because the relatively small capacity battery in the PV is regularly topped up by the main battery in the case, the PV vaping performance is very good and equivalent to that of a much bulkier PV with a large integrated battery; the latter is the sort of product that many smokers are reluctant to try because they look peculiar and unflattering to many smokers. A non-contact switch like a Reed switch in the case can detect removal of the PV and also re-insertion of the PV.

Figure 5:
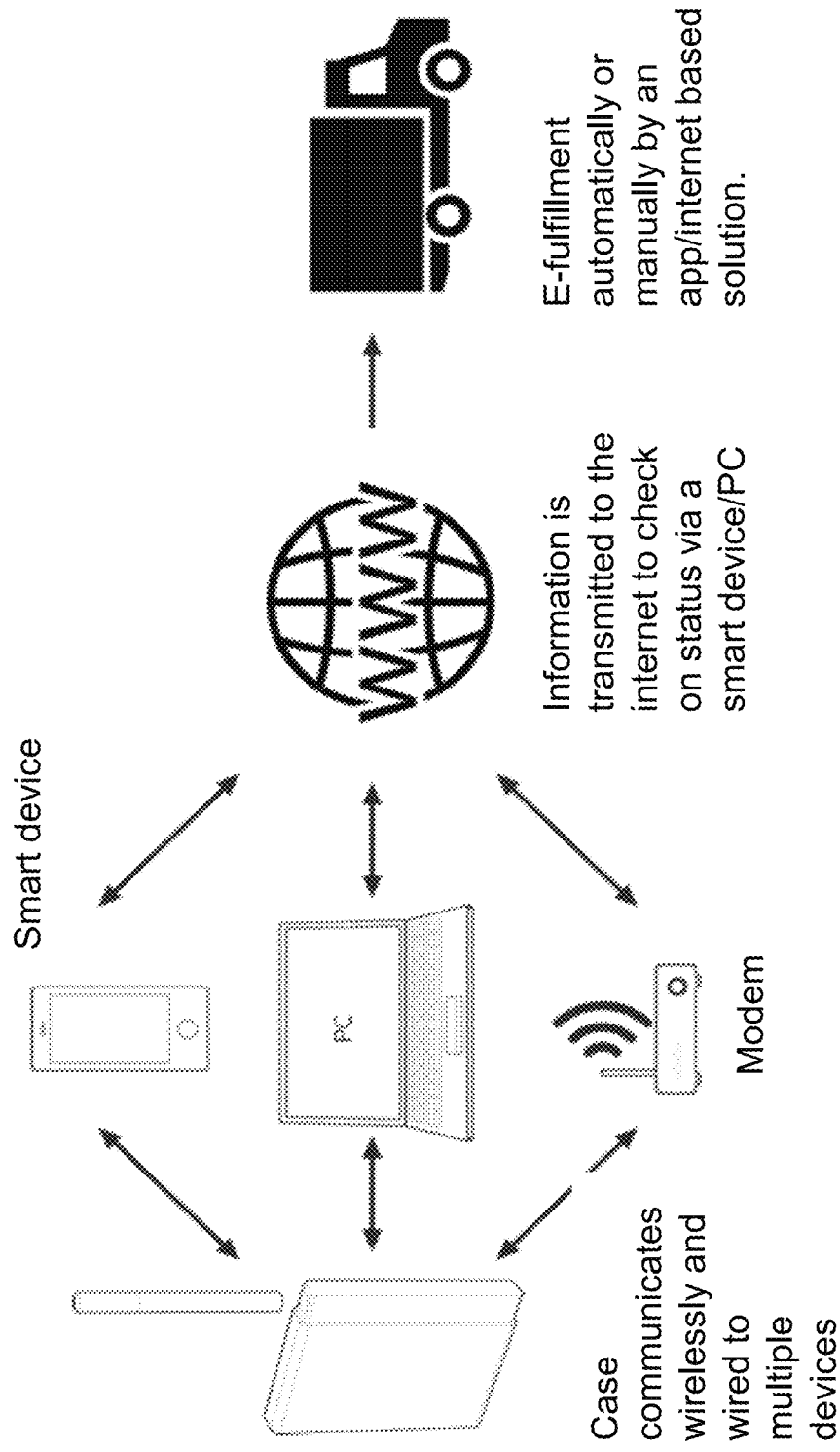
FIG. 5 schematically represents the connected nature of the electronic cigarette vaporiser system.

FIG. 5 shows schematically that the system is digitally connected; the case sends data to an app running on the user's smartphone, smartwatch, tablet or other computing device over short range wireless, such as Bluetooth. For example, when the case detects that the level of e-liquid in the cartridge is running low, then it sends a message to the app on the user's smartphone, alerting the user to that. The app gives the user the option of ordering replacement cartridges from an e-fulfillment platform. The case could also include a 3G, LTE or other form of wireless data module for direct communication with a remote server. Key features of the app are as follows:

Connects to the case via a Bluetooth connection on your Smartphone

From the app you can:
  Track your usage
  Purchase additional capsules direct to home
  Find the nearest shop to you
  Set goals—Financial, Health or use related
  Adjust basic settings on the vaporiser and case
  Get recommendations based on usage and taste
  See new flavours as they launch
  Receive special promotions
  Recommend a friend
  Set the system to auto-refill so that you never run out of capsules again and you don't have to keep on monitoring your level of liquid.

The case includes a USB C port for power and data transfer; the case can only be used with authorized chargers that can complete a satisfactory USB C handshake; this eliminates the danger from using cheap, unauthorized chargers.

The case includes an electronics module that controls the operation of the piezo pump and also logs usage statistics to improve customer service. The case gathers usage statistics and other data and sends it over the Internet, via the Bluetooth connected smartphone running a dedicated application, or directly, to the manufacturer's database.

The following data is logged and sent to the factory or manufacturer's database:

Power-up and power down events for both the case and also the PV (to enable the frequency and nature of handling to be measured).

Time of all use events (for example, users who always use the device first thing in the morning are likely to be highly addicted to smoking, and so progress with a nicotine reduction program is very useful to track)

System uptime (helps to improve battery usage and estimating liquid usage).

Vape count (i.e. the number and frequency of inhalations).
Vape strength (e.g. the strength of the inhalation).
Battery health.
Charging/discharged/charged events.
Vaping coil temperature.
Vape coil malfunction events.
Other malfunction events.
External temperature (for battery health and for correction of coil heating to ensure that the coil is at the optimal heating temperature, irrespective of ambient temperature).
E-liquid flavor, strength, ingredients and batch number
Any other information logged by the app: for example, the app could ask the user to rank their cigarette craving at various times during the day, both before and after using the electronic vaporiser on say a 1-10 scale; additionally, the app could ask the user if they are also still smoking cigarettes and how many, what times etc, whether any side-effects are experienced, whether the user feels fitter etc. This could provide valuable data indicating efficacy of the product, especially as part of a smoking reduction program or other clinical trials data that is useful for scientists and regulators.

All data is encrypted and standard data integrity techniques are used to guarantee that the data cannot be tampered with and that privacy is maintained.

Because the case is a connected device, it can be remotely locked. For example, if an owner loses the case, or is not in their direct control, or wants to ensure that it cannot be used by anyone else (e.g. children) then it can lock the case from the connected smartphone application.

Each capsule includes an authentication chip that is programmed with data such as the data of filling, batch number of e-liquid, source of e-liquid, tax or duty paid etc. Hence, if a specific batch of e-liquid is found to have contamination, then all cases in the world can be sent a message identifying those contaminated batches. The case, which checks the e-liquid batch number on each cartridge prior to filling from the cartridge, will then not fill from any cartridge with batch numbers matching the list of contaminated batches. Likewise, stolen or counterfeit cartridges, or cartridges for which duty has not been properly paid, can be identified by the manufacturer and a message sent to all cases to prevent their use. Finally, since use of e-cigarette electronic vaporisers may be unlawful in some places and countries, then the smartphone application, using the location capabilities of its host smartphone, can determine if the device is in a location where electronic vaporiser use is permitted or not and can disable the case and/or PV if appropriate. This can operate at the country level, or right down to specific buildings, airplanes etc.

Section B: Overview of Some Key Components in the System

Figure 6:
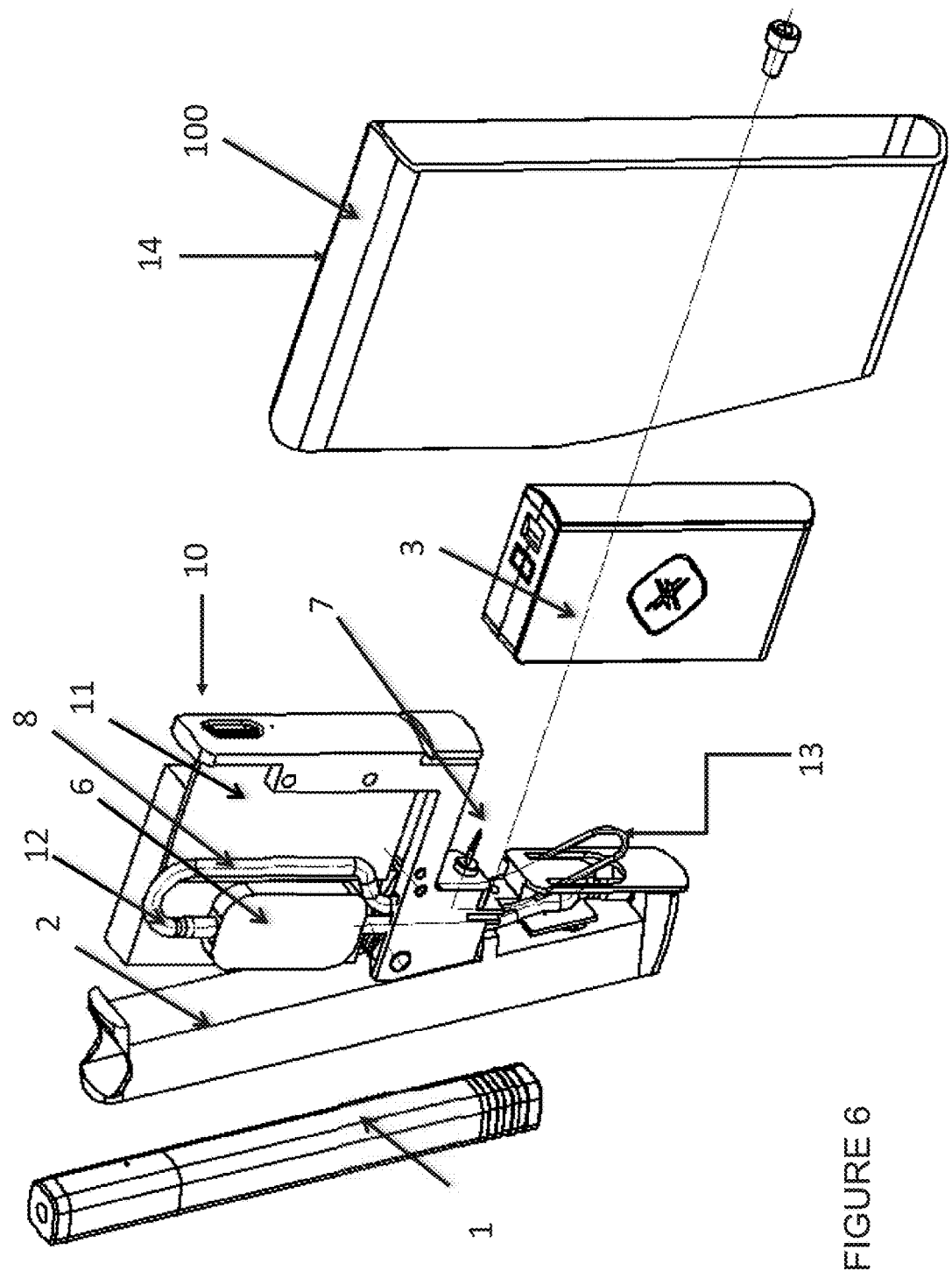
FIGS. 6 and 7 are exploded perspective views of the electronic cigarette vaporiser system.

Section A looked at the vaping system from the user experience perspective. In this Section B, we will give an overview of three of the main components in the system, as follows:

Section B1: Overview of the fluid transfer system
Section B2: Overview of the e-liquid cartridge
Section B3: Overview of the PV's atomising coil
Section B1: Overview of the Fluid Transfer System FIG. 6 is an isometric exploded view of the system. The case 100 includes a chassis assembly 10 on which all the major components are mounted. Chassis assembly 10 is slid into case assembly 14.

On the chassis assembly are mounted the electronics module on PCB assembly board 11, the piezo micro-pump 6, e-liquid inlet tube 12 that feeds the micro-pump 6 and the hinged PV holder 2 into which the user slides the PV 1. The replaceable 10 mL cartridge 3 slides into the side of the case 100, engaging against wire spring 13. As will be described later in more detail, the cartridge 3 includes a rubber septum; this is punctured by needle 7 when the cartridge 3 is fully inserted into the case; needle 7 leads via the thin tube 12 to piezo micro-pump 6.

Feed or inlet tube 12 includes a sensor 8 that can detect whether the feed into the piezo micro-pump 6 is liquid or air; this is very useful to know because the piezo-pump operates in different modes depending on the viscosity of the material being pumped. For example, if air is entering the piezo pump, then the piezo pump should operate at a high frequency, such as between 150-400 Hz (and preferably 300 Hz). But if the pump is pumping room temperature e-liquid, then the piezo pump should operate at a much lower frequency, such as 7-20 Hz (and preferably 15 Hz). If the e-liquid is even more viscous (for example, the ambient temperature is very cold), then the piezo pump may need to operate even more slowly. So being able to automatically alter the cycle time or frequency of the piezo-pump, based on an automatic assessment of the substance being pumped, is very useful. One way we can achieve this is for the sensor on the input line that feeds the piezo-pump to include a pair of electrical contacts on either side of the tube: when there is e-liquid in the portion of the tube around which the sensors are placed, then there is a large resistance (but one that is measurable by an electronics module in the case); when there is air in that portion, then the resistance is infinite or too high to measure. When e-liquid is detected, then that information can be combined with an ambient temperature measurement from a solid-state thermometer in the case to control the piezo-pump so that it operates at its optimal cycle time or frequency. Other sensing methods are possible: for example, a capacitive sensor or an infra-red light sensor (passing light through the inlet tube and detecting high or low levels of light absorption) could readily detect whether there was air or liquid in the piezo-pump inlet tube.

Where the piezo pump 6 has twin-piezo actuators, then one problem that can arise is that each actuator, over time, starts to operate slightly differently. Proper operation of the pump requires both actuators to operate identically, delivering exactly the same quantity of liquid for each pumping stroke. Pumping performance can drop significantly over time because of this mis-match in operation and output. In our system, a microcontroller can independently adjust the phase or timing of each voltage pulse that triggers a piezo-actuator—so for example, one actuator can be given a slightly longer or more powerful voltage pulse than the other if that would remedy the imbalance; the microcontroller can continuously or regularly monitor the efficiency of the entire pump (for example using a small MEMS based flow sensor) and adjust the phase relationship until the optimum pumping performance is achieved. For example, if one actuator is delivering less e-liquid than the other, then the power delivered to the first actuator can be increased, e.g. the start of the voltage pulse can be brought forward or the peak voltage delivered to the first actuator can be increased, all relative to the second actuator. The microcontroller can monitor the pumping performance of the entire unit and adjust the various parameters until optimal pumping is achieved.

The output tube from the piezo micro-pump 6 leads to a filling stem or tube (not shown in FIG. 6, but integer 4 in FIG. 9) at the bottom of the hinged holder. This filling stem engages with a filling aperture in the bottom end (or side) of the PV, as will be described later.

Careful selection of materials is needed for nicotine compatibility—for example, nicotine can react with some plastics (such as polycarbonates), can leach compounds out of other plastics and can evaporate through others. Tubing 12 can be made of an inert nicotine-compatible material such as Tygon™ LMT55; the piezo-pump can be the MP6 micro-pump from Bartels Mikrotechnik GmbH with actuators made of polyimide.

Figure 7:
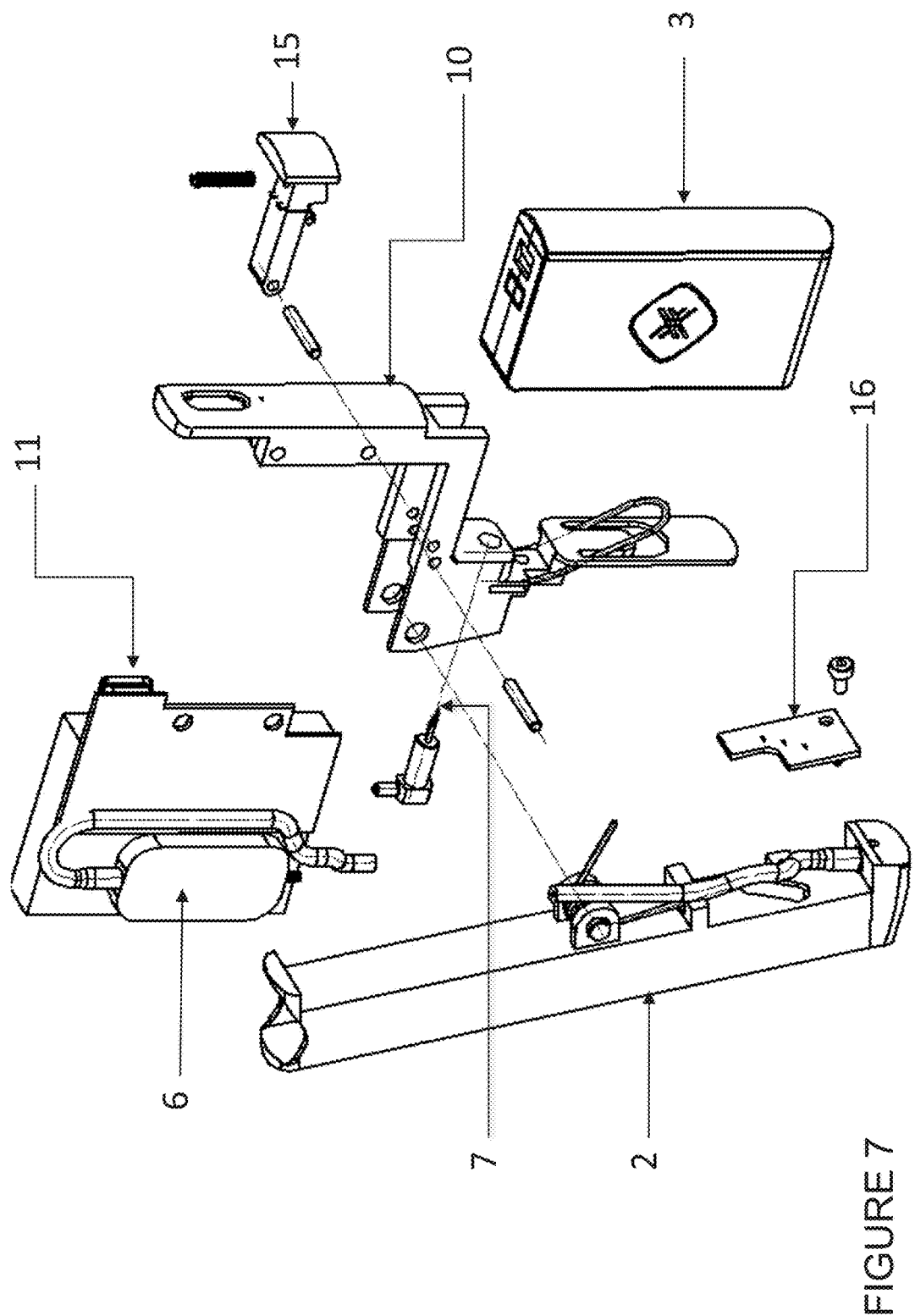

FIG. 7 is an isometric exploded view of the chassis assembly components from FIG. 6. Specifically, FIG. 7 shows the hinged PV holder 2, micro-pump 6 mounted on PCB assembly board 11, chassis 10. FIG. 7 also shows the trigger latch assembly 15; this is pushed by the user to eject cartridge 3 using the force of wire spring 13. Electrical contacts are made to ring contacts on the PV via a contacts assembly 16; power and data is transferred via contacts assembly 16.

Figure 8C:
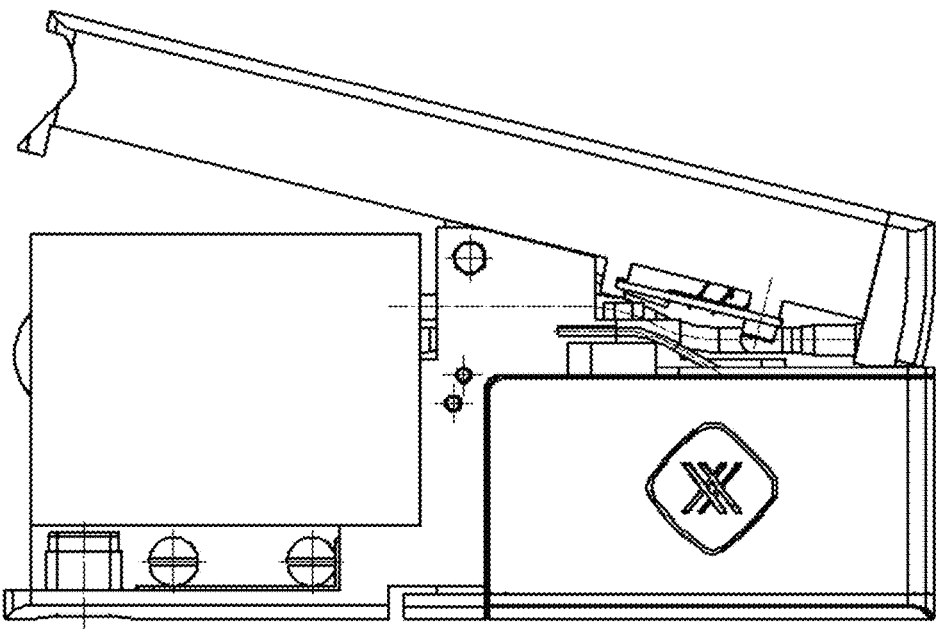
FIGS. 8A, 8B and 8C are right, rear and left side views, respectively, of the major components in the case for the electronic cigarette vaporiser system.
Figure 8B:
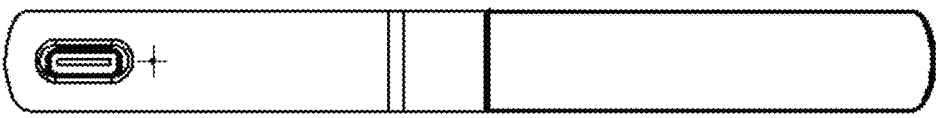
Figure 8A:
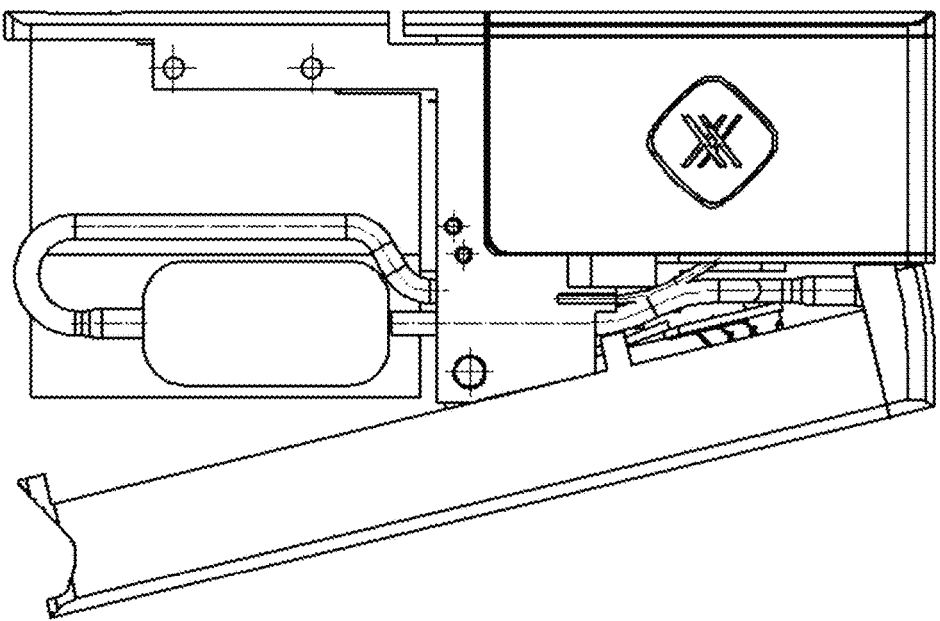

FIG. 8 are orthographic views, front and back, of the fully assembled system, with the cartridge slotted into position, and the hinged holder in the open position.

FIG. 9 shows five cross section views (FIGS. 9A to 9E) of the chassis assembly. FIG. 9A shows a top view, including the empty PV holder 2 and a small display panel 17 that shows system information using simple graphics (such as battery charge state; e-liquid fill state). A section XX line is drawn and FIG. 9B is the side view cross section along the XX line. Main battery 5, hinged PV holder 2 and filling stem 4 are shown. At the base of the filling stem 4 is a simple spring-biased stainless steel ball 16 which acts as a stop valve; when piezo-pump 6 pumps e-liquid into the PV, then stainless steel ball 16 rises off its seat and permits e-liquid to pass up the filling stem 4. As soon as piezo-pump 6 stops pumping, stainless steel ball 16 sits back down and seals the filling stem, preventing any downstream drops of e-liquid from dripping out. A read/write data contact 13 contacts the data leads for the security or authenticator chip fixed to the cartridge. FIG. 9C shows the PCB assembly board 11 that lies adjacent to the case battery 5, mounted on chassis assembly 10. Piezo-pump 6 is mounted on the battery 5 and is fed e-liquid from e-liquid inlet tube 12. An infra-red sensor 8 is placed around the e-liquid inlet tube 12 and detects whether the inlet tube has air in it at that point, or e-liquid (since the light absorption of e-liquid is far greater that air). The inlet end of the e-liquid inlet tube 12 is connected to a needle 7; in this needle punctures the septum in the cartridge and enables e-liquid to be sucked out from the cartridge by the piezo-pump 6.

FIG. 9D is a rear view, showing needle 7. FIG. 9E is a side view, showing the battery 5.

Key features of the case are the following:

Case Feature 1: The case includes a piezo-electric pump. The case includes a piezo-electric pump to transfer small but accurate quantities of e-liquid in from the cartridge or other parent reservoir to a child reservoir in the PV.

Case Feature 2: The case or PV has a 'discrete' mode. In 'discrete' mode, the PV reduces the amount of vapour produced, or its density (e.g. by reducing the coil temperature by 10%) but maintains that temperature within a range where the vaping experience is still good, but vapour quantity or density is reduced. This is useful for a restaurant or office.

Case Feature 3: The case or PV includes a 'power mode' with coil temperature monitoring—e.g. to increase the amount of vapour produced, the user can activate a button or sensor on the PV, but crucially coil temperature is measured or inferred or limited to ensure that it remains at a safe operating temperature.

Case Feature 4: The case has a PV ejection mechanism: An automatic lifting mechanism (e.g. magnetic or spring-based) that gently lifts the PV up a few mm from the case to enable a user to easily grasp it when the case is opened.

Case Feature 5: A non-contact sensor in the case detects PV release from the case: A non-contact sensor (e.g. a magnetic sensor, such as a reed switch, Hall effect sensor) detects when the PV enters and leaves the charge/re-fill case.

Case Feature 6: A sensor in the feed-line to the fluid transfer mechanism (e.g. piezo pump) detects characteristics of the flow through the feed-line and automatically alters the operation of the fluid transfer mechanism depending on the detected or inferred nature of the substance (e.g. air or e-liquid; the viscosity of that e-liquid) passing through the feed-line.

Case Feature 7: Any imbalance in the operation of a piezo-actuator that forms a pair of piezo-actuators is detected and the phase or voltage profile delivered to that actuator is altered so that the imbalance is addressed.

Section D gives further details of each of these features.

Section B2: Overview of the e-Liquid Cartridge

Figure 10:
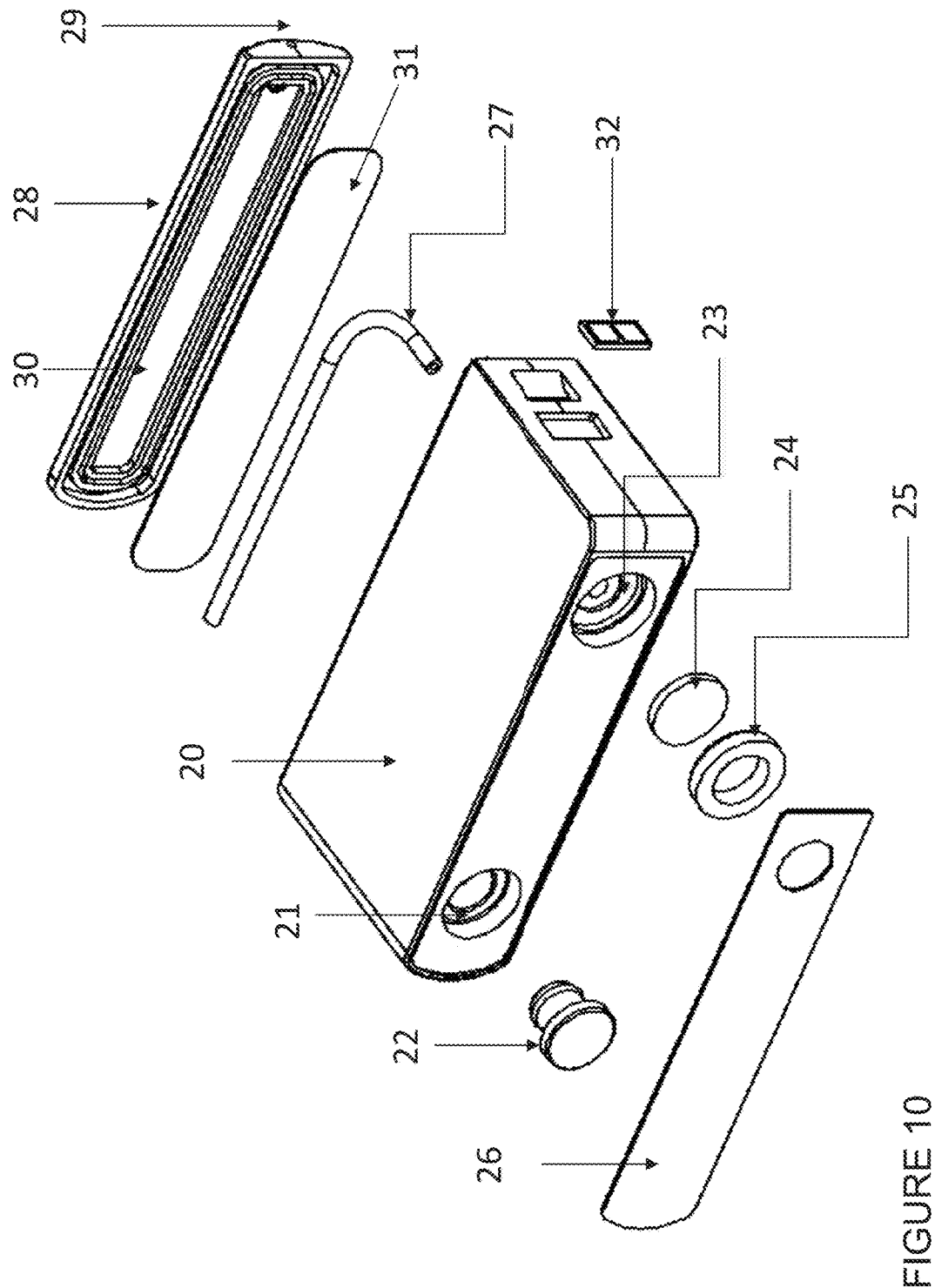
FIG. 10 is an exploded perspective view of the major components in the cartridge for the electronic cigarette vaporiser system.

FIG. 10 is an isometric exploded view of the components in the cartridge. The cartridge includes a body 20 made of a clear plastic material that is compatible with nicotine storage (such as HDPE—high density polyethylene; PETG—polyethylene terephthalate; or COC—cyclic olefin copolymers) with two apertures in its top face; the e-liquid inlet aperture 21 to the left side of the body is used when filling the cartridge on an automated or semi-automated filling line: 10 mL of e-liquid is passed into the cartridge through a filling head and then inert argon gas purges all oxygen from inside the cartridge to prevent oxidation of the nicotine. A bung 22, or other form of seal, then seals or closes off that aperture 21. A rubber septum 24 sits in aperture 23 and is sealed in place with ring 25 and seals aperture 23, which is the e-liquid outlet aperture. The septum 24 is a PTFE (polytetrafluoroethylene)/silicone/PTFE disc.

So the cartridge includes two apertures, (a) an outlet aperture 23 being sealed by a septum 24 designed to be penetrated or punctured by a needle or stem in the case that withdraws e-liquid from the cartridge and (b) an inlet aperture 21 being used to fill the cartridge on a filing line and then being covered with a bung or plug 22. Aperture 21 enables fast and efficient filling on an automated filling line, reliable sealing of the cartridge to minimize contamination risk and also easy integration of the cartridge with the case, all at very low cost.

An adhesive, tamper evident strip 26 is then applied over the top of the bung 22 and the septum 24 and ring 25. The body includes a standard scavenger tube 27 fixed to the outlet 23 that leads to the rubber septum 24, so that the last droplets of e-liquid in the cartridge can be extracted.

An air pressure valve is included in the cartridge. If no air pressure valve is provided, then, as the cartridge empties, a partial vacuum forms, retarding fluid transfer out of the cartridge. The valve also prevents contaminants from entering the cartridge/reservoir, which hence preserves the condition and stability of the e-liquid. It also permits only limited quantities of air to enter the cartridge (e-liquid can deteriorate when exposed to free flowing air for long periods).

The valve has the following structure. A lid 28 is positioned against one face of the cartridge body. The lid 28 includes a small air hole 29 to allow air to enter and leave a plenum 30 formed by the lid 28 as one face, and ridges in the lid 28 as the sides and a Porex™ PTFE sheet 31 facing the lid as the opposite face. The sheet can be any material that is impermeable to e-liquid but bi-directionally permeable to air, hence enabling air pressure equalization within the cartridge; PTFE is especially suitable because it is very stable in the presence of e-liquid, and so introduces no contaminants. The plenum 30 provides for a large surface area for the air/PTFE interface. Other materials apart from PTFE are possible; for example, paper coated with PTFE may be suitable. The air-side of the PTFE sheet 31 may include fine strands of polypropylene to increase the surface area and to facilitate welding to the clear plastic body 20.

Another feature is that each cartridge has its own unique serial number written in a One-Wire flash memory chip or authenticator 32, such as the Maxim DS28E15 security chip. After a cartridge is installed into a case, a microcontroller (MCU) in the case reads its serial number and verifies that its hash-function is valid. If the verification is good, the cartridge will be used to refill the PV. If not, the MCU in the case will block any liquid usage from such cartridge.

The manufacturer tracks all serial numbers so that if some cartridges are found to be defective then all cartridges made as part of the same batch can be identified and a signal sent to the case to prevent them being used and to trigger an explanatory message to be displayed on the smartphone application. The term microcontroller used in this specification includes other forms of processors, microprocessors, ASICs etc.

The MCU can also write-data into the chip 32—for example the estimated or measured amount of e-liquid left in the cartridge; this enables cartridges that have been unlawfully re-filled to be spotted by the MCU (since they can be tracked to have expelled significantly more than the known capacity of the cartridge—e.g. 10 mL) and can then be prevented from being used.

At manufacture or filling or fulfillment (or a combination of these) data is burnt to the chip that defines flavor, nicotine strength, batch number, date of manufacture, tax paid and any other useful information. The cartridge is then packaged and ready to be shipped. FIG. 11 are side, top and front views of the cartridge. The total fluid capacity is 11.6 cc.

In addition, the cartridge could include a bag-in-bottle or BiB system—e.g. this would allow the contents of the cartridge to be almost completely emptied, avoiding wastage, yet also protecting the contents of the cartridge from oxidation and contaminants. A material like DuPont Surlyn can be used for the inner bag.

Key features of the cartridge are the following:

Cartridge Feature 1: The cartridge or other form of parent reservoir includes an air pressure valve.

Cartridge Feature 2: the cartridge includes a memory chip

Cartridge Feature 3: the cartridge includes two e-liquid apertures, one an inlet, the other an outlet.

Cartridge Feature 4: the cartridge stores the batch number of the e-liquid it is filled with and can be remotely disabled from using specific batch numbers Section D describes these features in more detail.

Section B3: Overview of the PV's Atomising Coil

Figure 12:
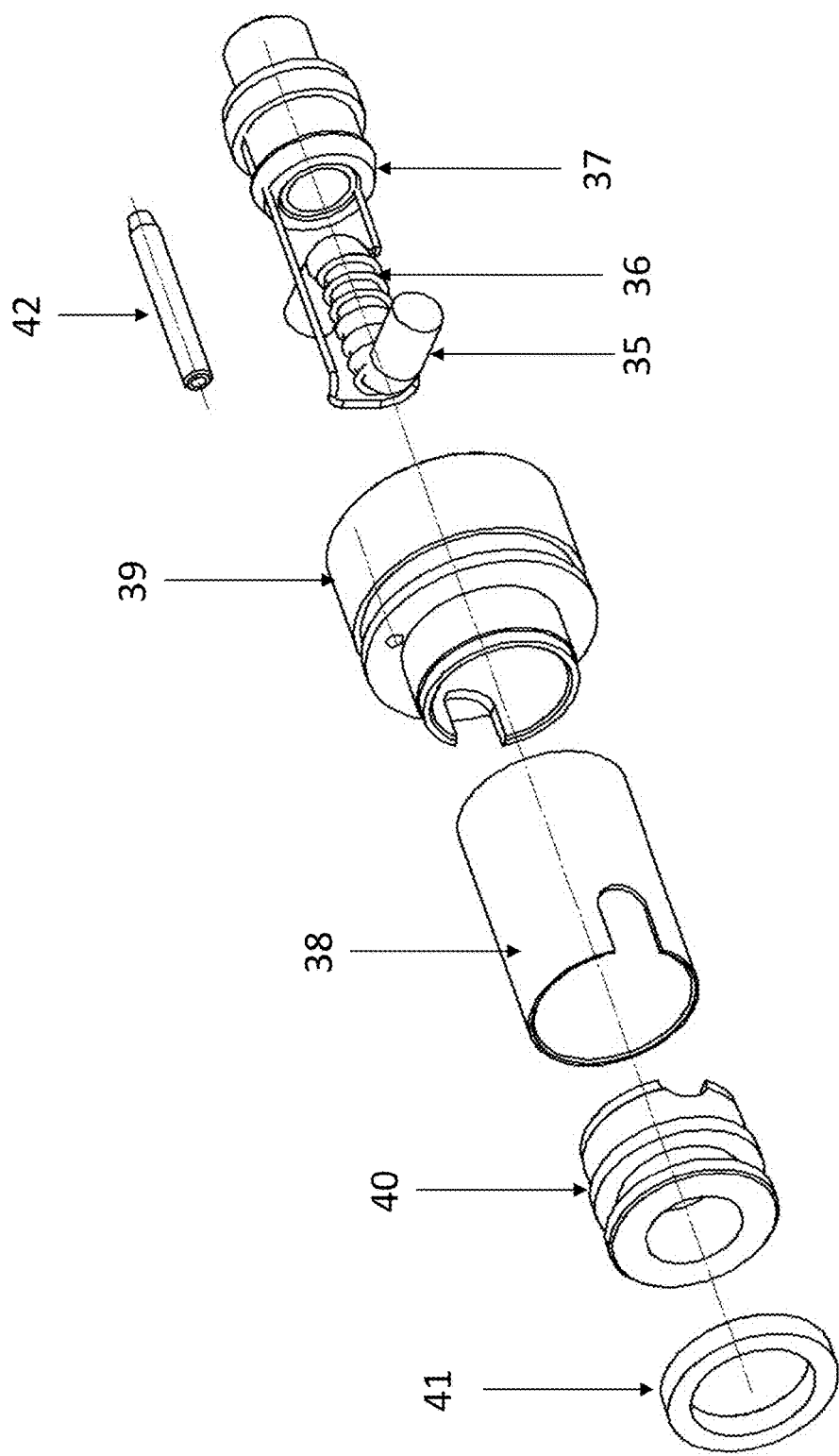
FIG. 12 is an exploded perspective view of the major components in one design of atomising unit.

We will now look at the wick and heating coil assembly. FIG. 12 is an isometric exploded view of the components in one type of wick and heating coil assembly. The wick 35 can take several different forms, such as a ceramic cell like the cCell from Shenzen Smoore Technology Limited, or a more conventional cotton wicking coil arrangement.

FIG. 12 shows the latter; it shows a 'z' shaped piece of compressed cotton 35 or a porous ceramic with a body arranged longitudinally along the long axis of the PV electronic vaporiser in a vapourising chamber to interrupt the air flow path through that chamber. One end of the wick 35 includes an end section, angled at right angles with respect to the body, and protruding into an e-liquid reservoir; the other end of the wick includes an end section, also angled at right angles with respect to the body, and protruding into that e-liquid reservoir. A NiChrome wire heating element 36 is wound around the wick body 35; other materials for the heating element may also be used, such as titanium, tungsten and other materials; the key design criteria for material choice is to minimize the risk of any harmful products entering the user's lungs, particularly as the heating element starts to degrade. Coil assembly 37 is mounted inside tube 38, closed off at one end by body 39 and at the other end by end cap 40, which seals against 'O' ring 41. Tube 38 forms the inner wall of the e-liquid reservoir; this small reservoir, capacity approximately 0.2 mL, surrounds tube 38. The cotton wick 35 protrudes through a gap in the side of tube 38 into this reservoir, drawing e-liquid in from the reservoir.

The FIG. 12 design is especially easy to mass-assemble since it requires very few steps to complete. Also, because the heating element and wick runs longitudinally through the vapourising chamber, and there is no straight through path for air through the vapourising chamber, but instead the incoming air has to flow around and over the heating element and wick, the design provides a good quality vaping experience.

Figure 13:
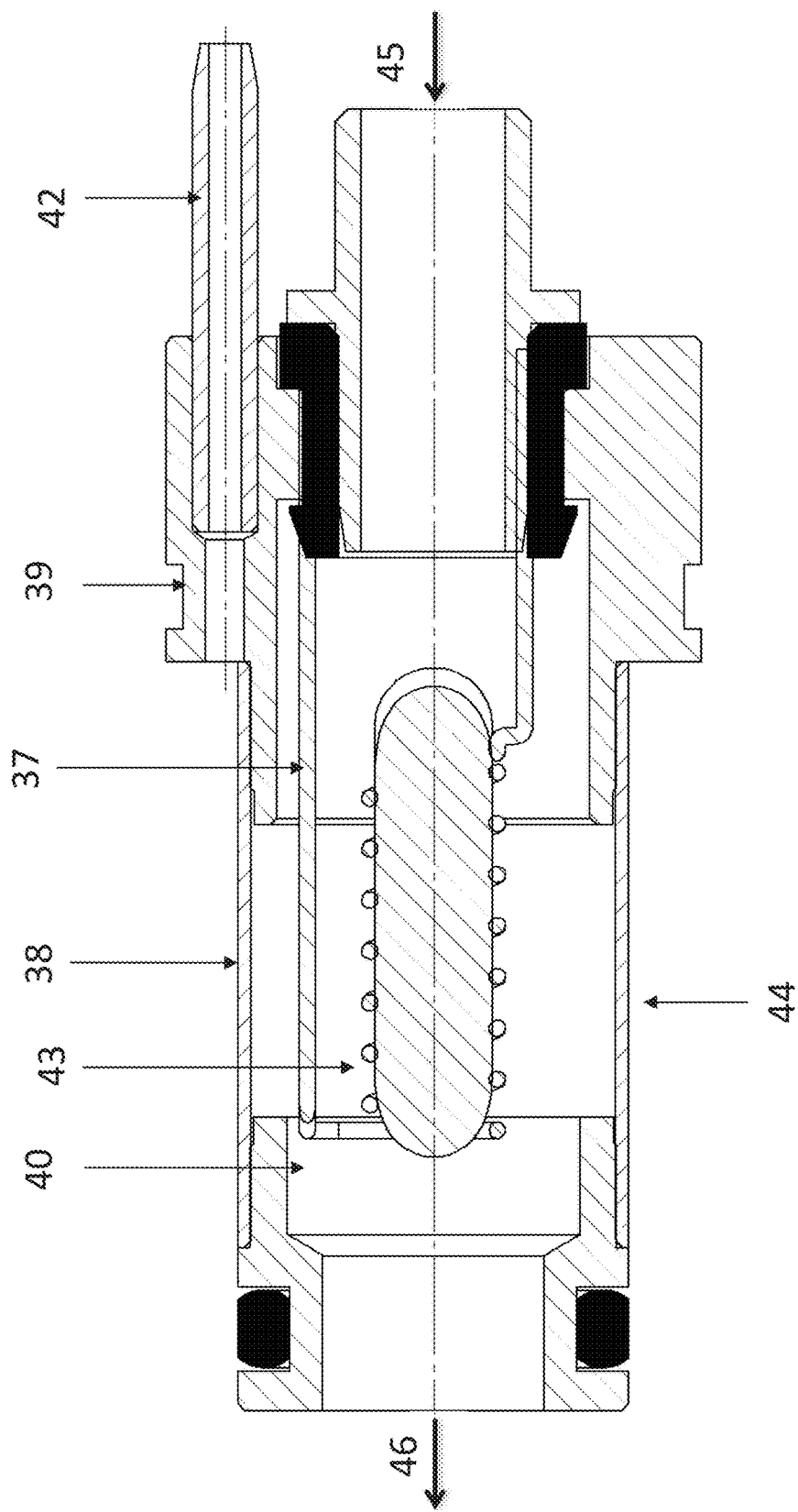
FIG. 13 is a cross-section view of the major components in the atomising unit.

FIG. 13 is a cross section through the fully assembled wick and coil assembly. It shows the e-liquid stainless steel feed pipe 42 (which is connected to the piezo micro-pump during filling and filled with e-liquid from the cartridge) that feeds the concentric reservoir, indicated generally at 44, that surrounds tube 38. E-liquid is pumped into the reservoir 44 and then drawn by the wick into the coil assembly. Air passes from inlet 45 and then has to divert up and around the coil and assembly 37; the chamber 43 is the atomizing chamber where heated micro-droplets of e-liquid are carried by the air passing over the coil out through aperture 46. But requiring the airflow to divert up and around the coil assembly, vortices are formed which are more efficient at drawing out the micro-droplets of e-liquid.

Figure 14:
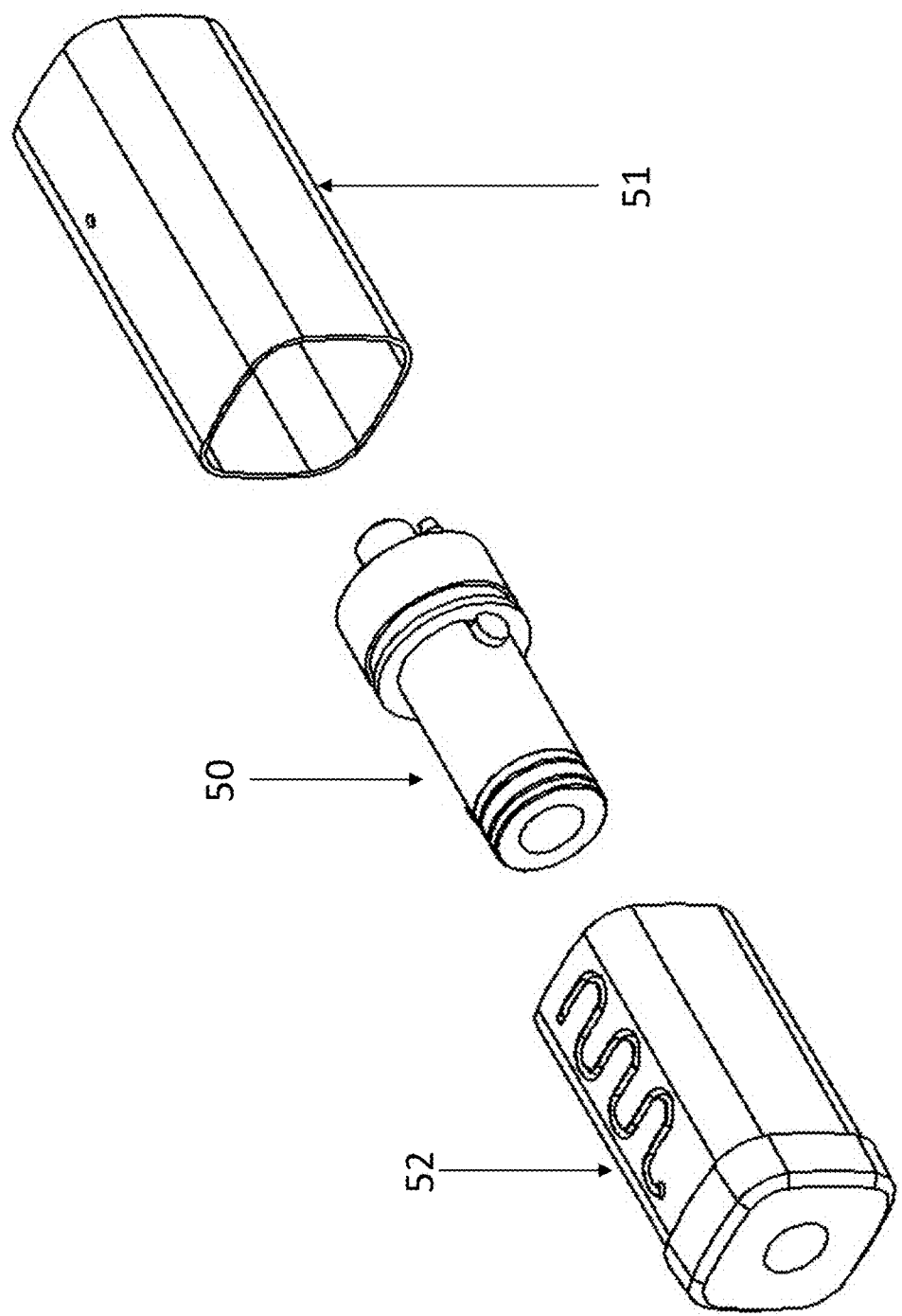
FIG. 14 shows the user-replaceable tip and the atomising unit.

As shown in FIG. 14, the fully assembled wick and coil assembly 50 is inserted into a coil holder 52 which serves as a mouthpiece; the coil holder 52 can then be press-fitted onto the main tube 51 of the PV that includes the battery, electronics and e-liquid filling aperture (which is at the end of the PV furthest from the mouthpiece).

The combined mouthpiece/coil holder 52 can be readily removed from the tube and replaced with a new or different combined mouthpiece/coil holder; hence, as soon as there is any sign of degradation of the wick or coil, or perhaps the user simply wishes to try a different wick/coil design (since it may deliver different vaping characteristics), then the user can simply pull the old coil holder 52 off and insert a new one. Hence, the PV includes a front section 52 containing a wick and heating assembly but no e-liquid cartridge; the front section is removable to enable a replacement front section to be used, for example once the original wick or heating element starts to degrade. The rest of the PV can be re-used with a fresh front section 52.

Note that because the case has a micro-pump (e.g. piezoelectric or peristaltic or any other effective, reliable, accurate and low-cost form of pump), it can be used in reverse to fully drain the PV of e-liquid so that if the coil holder is replaced then there will be very little e-liquid to drip out. Activation of the reverse pumping can be through a control on the case, or via an app on a connected smartphone: for example, with the PV stored in the case, then the user opens up the associated app on his smartphone; one option is 'drain PV if replacing coil holder'; when that is activated, then the app sends a control signal to the electronics module in the case, which in turn causes the micro-pump to operate to drain the PV fully. When switching between flavours, it can be useful to vape with a completely unflavoured e-liquid; a 'cleaning' routine with unflavoured e-liquid is hence supported.

The PV includes an air pressure valve or device so that excess air can escape from the e-liquid 'child' reservoir in the PV. Air needs to escape from the child reservoir in the PV when that reservoir is being filled up with e-liquid, and air needs to enter into the child reservoir as e-liquid is consumed in normal use, since otherwise a partial vacuum would be created, which would tend to prevent or retard e-liquid in the child reservoir wicking/entering the atomising coil unit. The PV air pressure relief system, used with the cotton-type wick of FIGS. 11-13 is shown in FIGS. 15-19.

Figure 15:
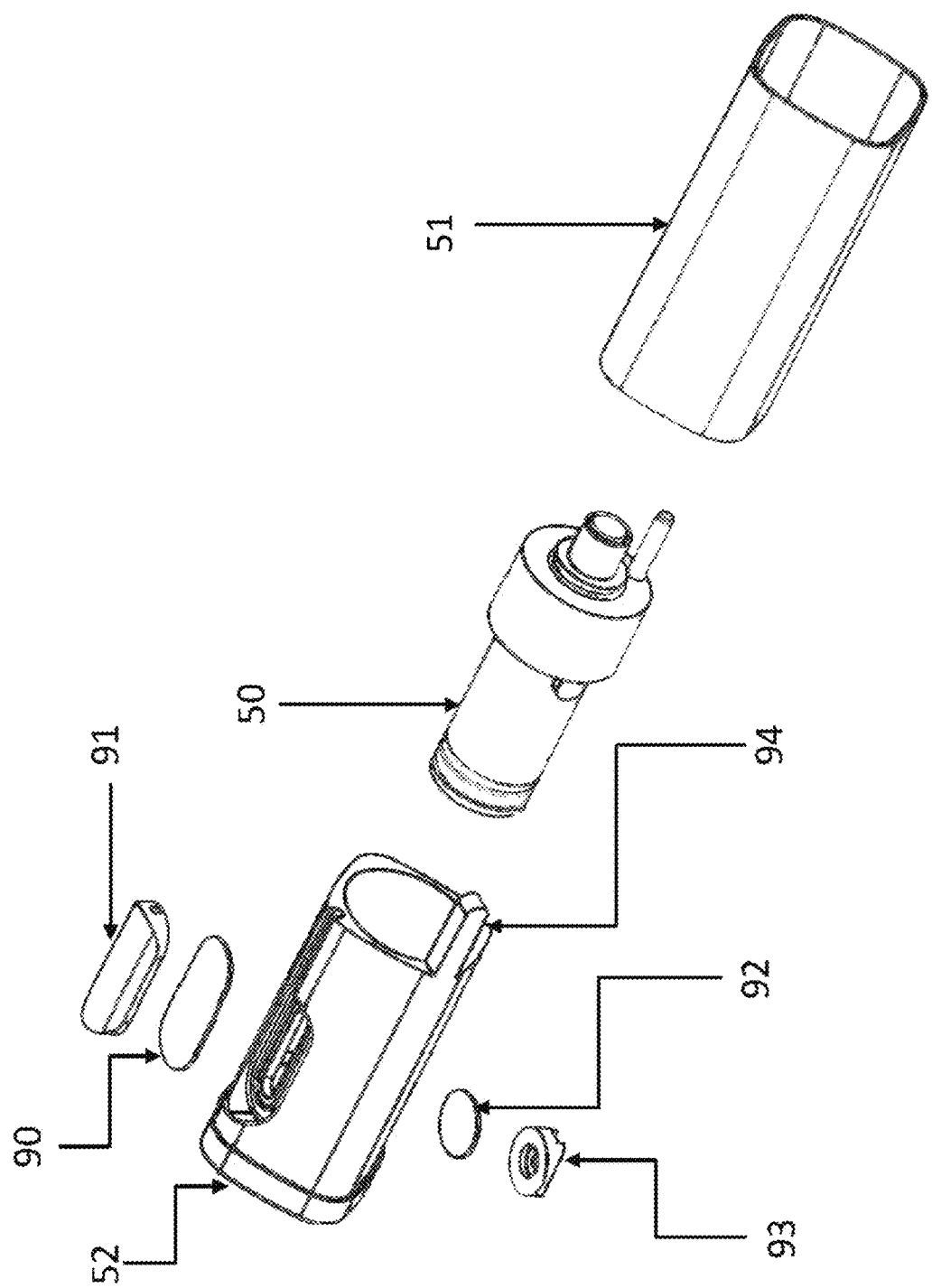
FIG. 15 shows the tip and an air pressure equalization valve in the vaporiser.

FIG. 15 is an exploded view of the PV tip assembly. The coil wick assembly 50, shown in FIGS. 12, 13 and 14, is inserted into a cast aluminium alloy LM25 tip casting 52; tip casting for the mouthpiece 52 is then inserted into the body 53. Tip casting mouthpiece 52 includes the air pressure relief system; this includes a rounded rectangle shaped membrane 90 on one side of the mouthpiece 52, secured by slug 91. On the opposing face of the casting 52 is a second, circular PTFE membrane 92, secured in place by slug 93. Instead of a PTFE membrane, other materials are possible; these materials must be porous to air, but impermeable to e-liquid. Sintered metal is one alternative material; a porous ceramic could also be used.

Figure 16:
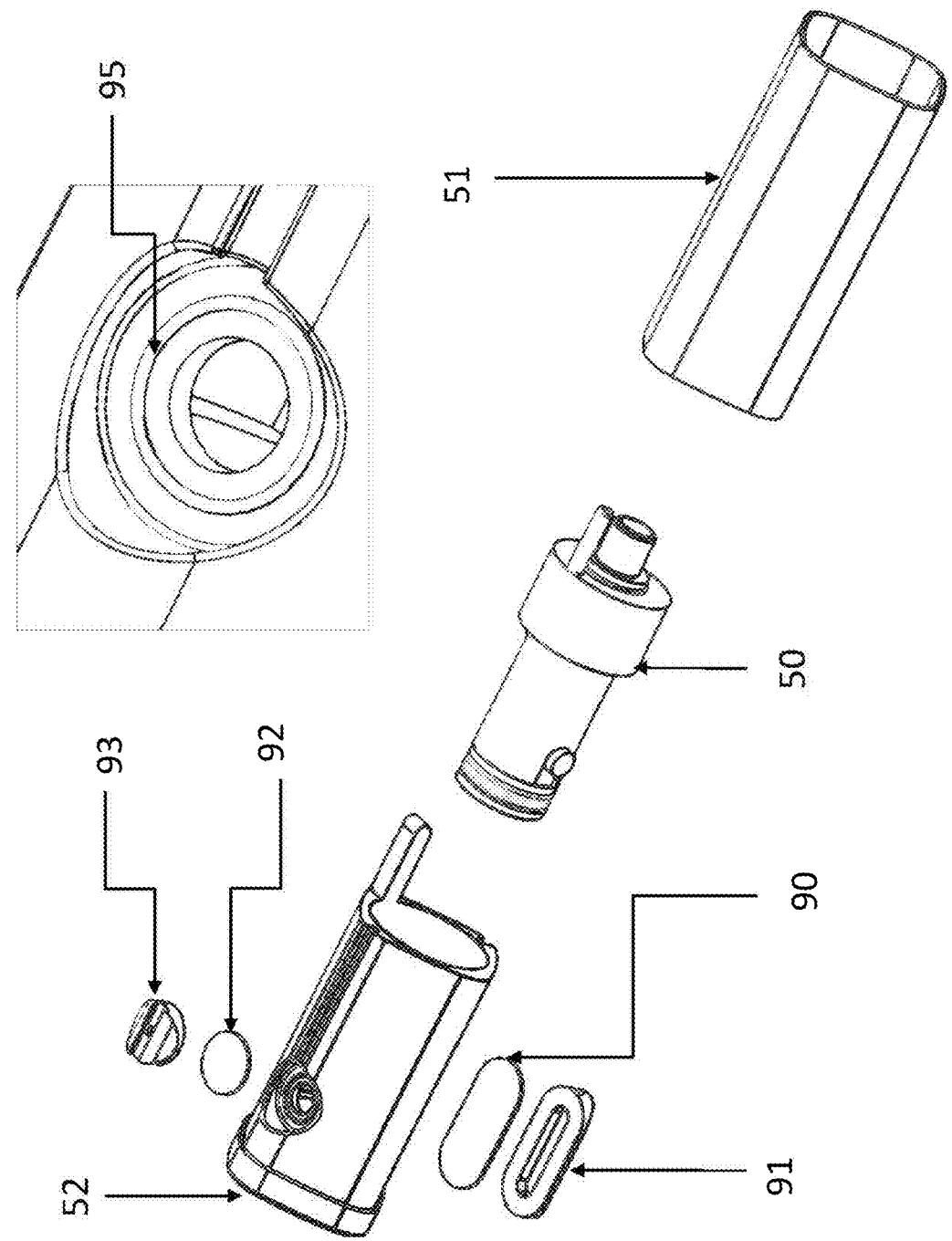
FIG. 16 shows an exploded view of the air pressure equalization valve.
Figure 17:
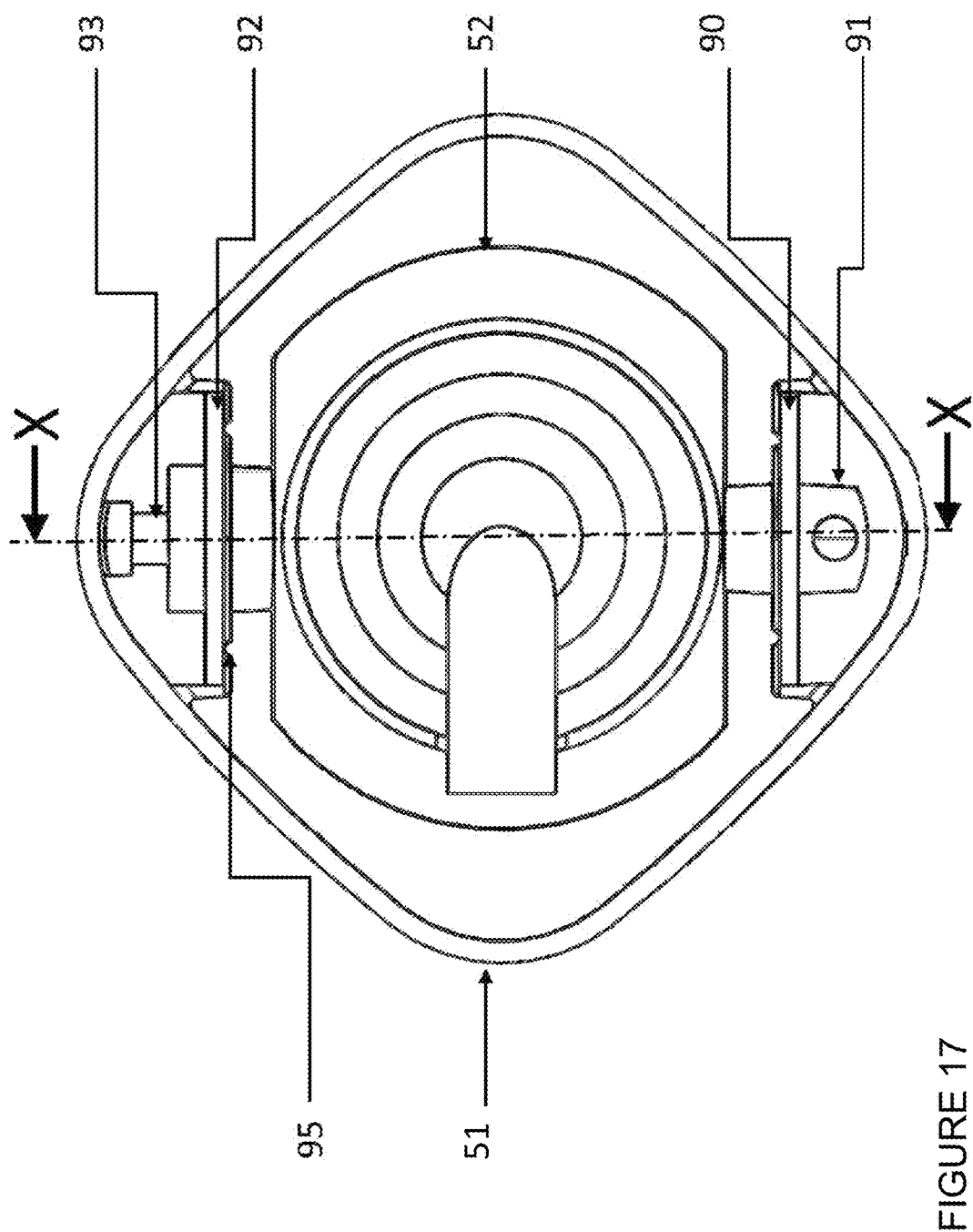
FIG. 17 is a cross-section frontal view of the air pressure equalization valve in the vaporiser.

FIG. 16 shows the FIG. 15 construction but from a different viewpoint. FIG. 17 is a cross-section view through this construction. There is an interference fit between each slug 91, 93 and the body 53; this creates a compressive force on each PTFE membrane 90, 92, which each sit on bead 95.

Figure 18:
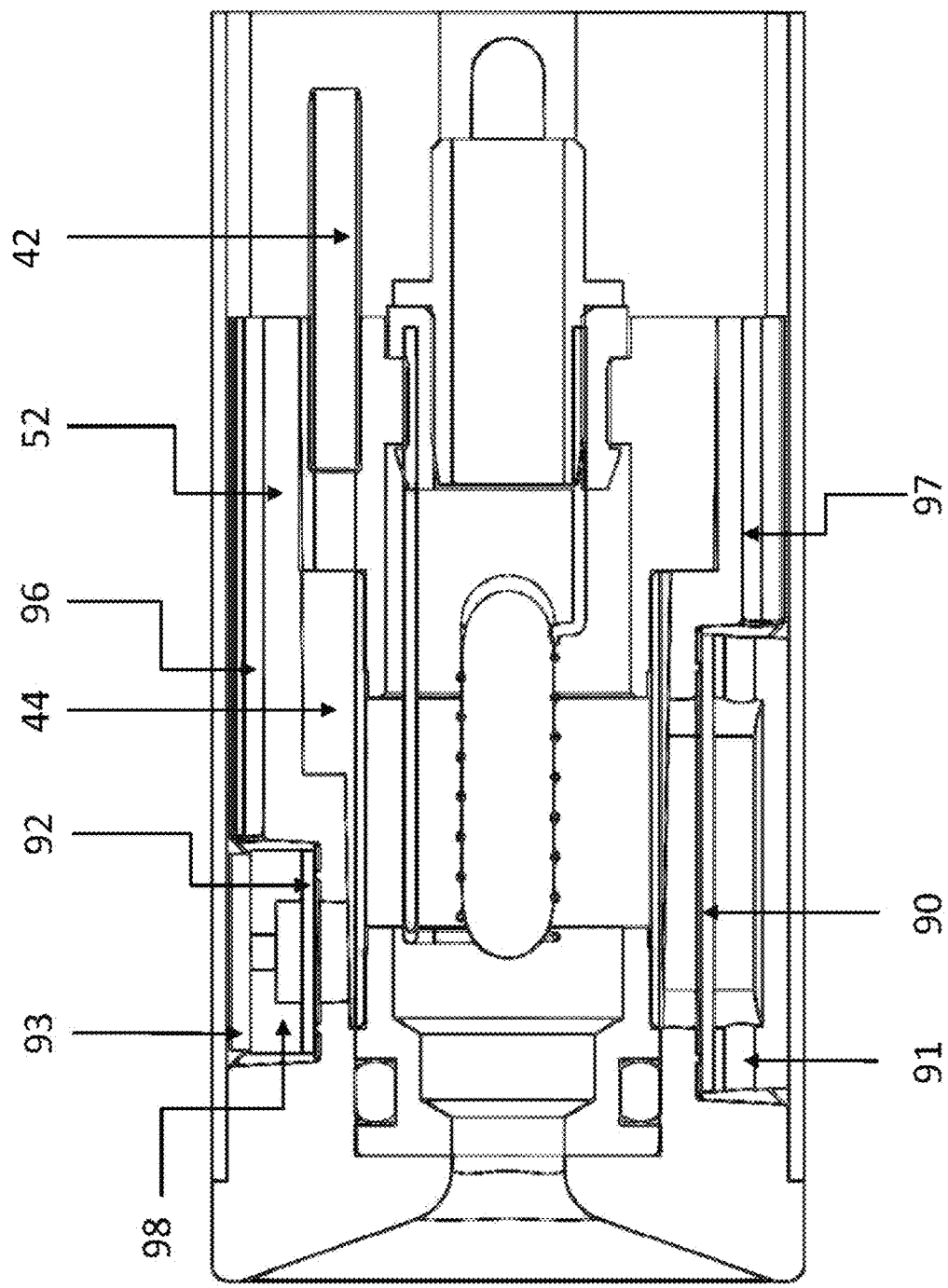
FIG. 18 is a cross-section side view of the air pressure equalization valve and atomising unit in the vaporiser.

FIG. 18 is a longitudinal cross-section through the X-X marked in FIG. 17. In addition to the components shown in FIG. 17, we show in this cross-section the e-liquid feed pipe 42 that feeds the reservoir 44. Air is displaced up past each PTFE membrane 90, 92 and passes along an air vent channel 96, 97, formed in the top of tip casting 52.

FIG. 19A shows the fluid path 98 and the air path 99 (note that air can flow both in and out of the PV through this air path; if the air pressure inside the PV drops (for example, it is in an airplane flying at high altitude), then air needs to pass into the reservoir 44 to prevent e-liquid leaking out from the PV.

Figure 19B:
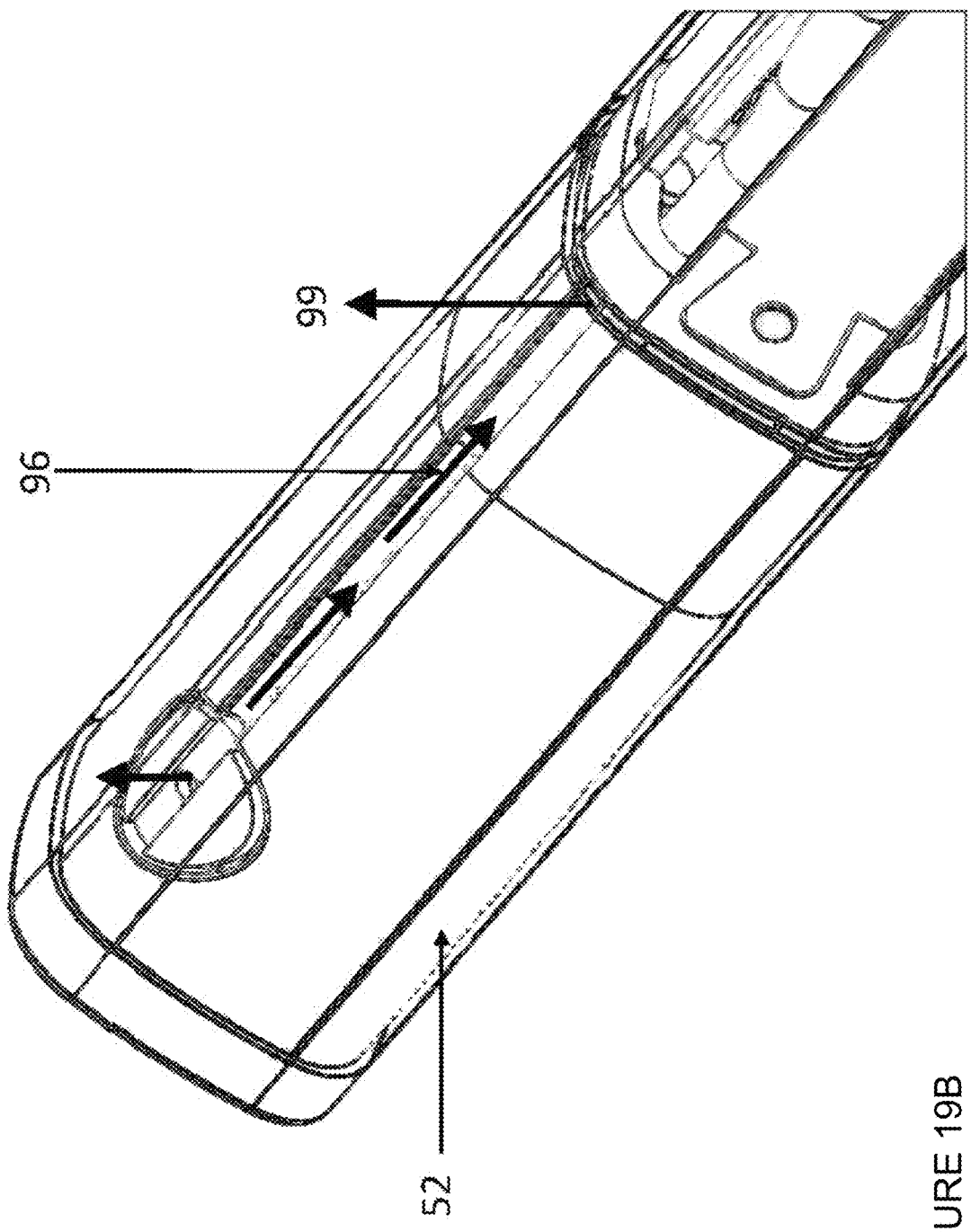
FIG. 19B is a perspective view of the vaporiser and the air flow pattern.
Figure 19C:
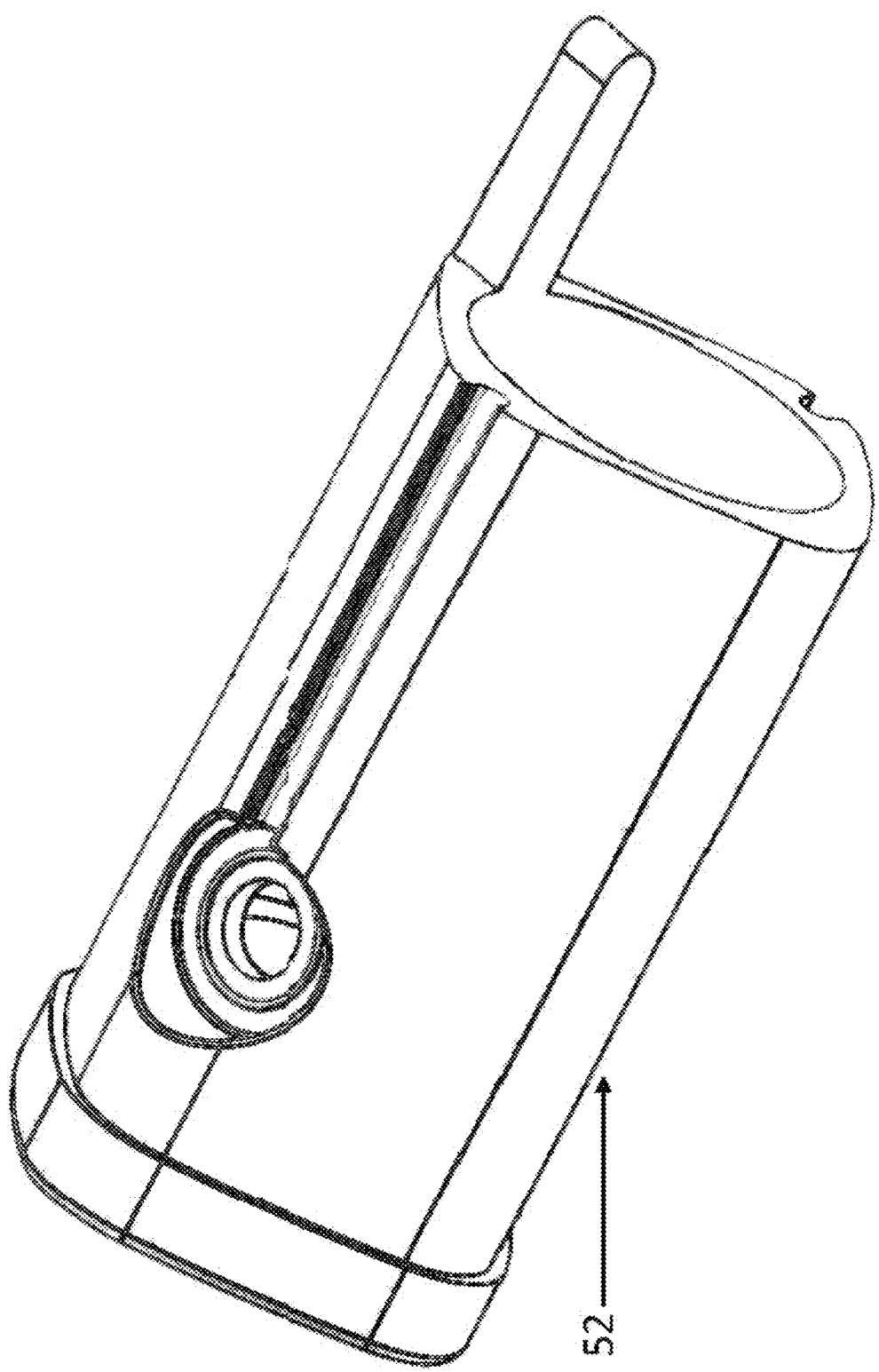
FIG. 19C is a perspective view of the vaporiser.

FIG. 19B shows a perspective view of the air vent channel 96 formed in the top of tip casting 52, with the arrows indicating the air escape path 99. FIG. 19C shows a perspective view of the tip casting 52 with the slug removed.

Where a ceramic cell is used, such as the T28 from Shenzen Smoore, then the cylindrical wall of the ceramic cell itself serves as the air-pressure valve because the wall is itself bi-directionally air-permeable. During pressurised filing of a PV that has a ceramic cell, or if ambient air pressure drops, then air can pass through the wall and into the atomizing chamber which vents to the outside. Conversely, if the ambient air pressure increases, then air can pass into the internal reservoirs in the PV via the ceramic walls—in both cases, this ensures that air pressure equalization is achieved, and without the need for an additional air pressure relief system as shown in FIGS. 15-19.

A ceramic cell however presents leakage challenges when being filled under pressure, as happens with the design we are describing. We solve this problem with a pair of silicone washers, end-caps or 'O' rings on either end of the cylindrical ceramic cell. This is shown in FIGS. 20-25.

Figure 20C:
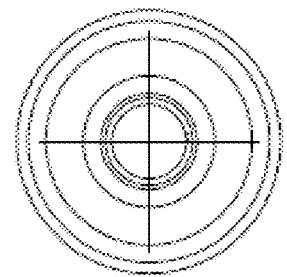
FIGS. 20A-C are top, side cross-section and bottom views, respectively of a ceramic cell atomizing unit with silicone end-pieces.
Figure 21:
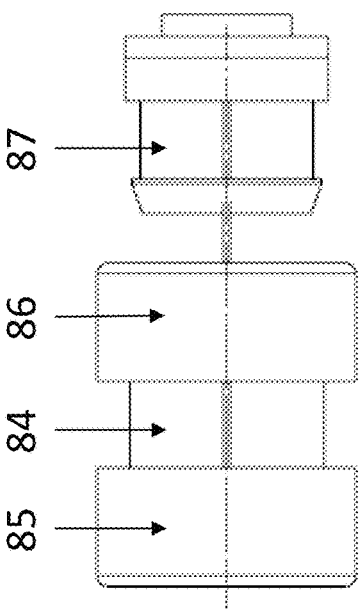
FIGS. 21-22 show a ceramic cell atomizing unit with silicon end-pieces.
Figure 20B:
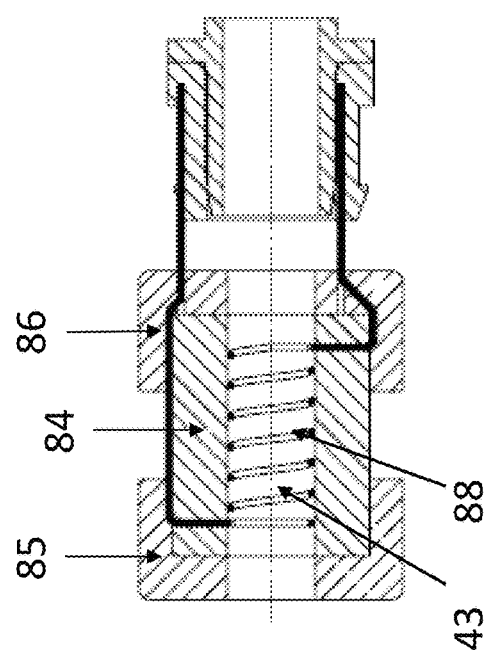
Figure 22:
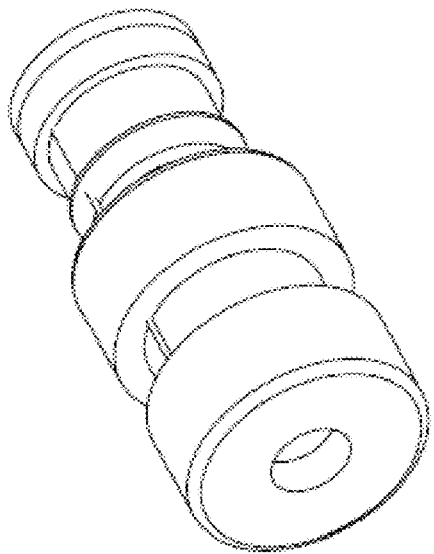
Figure 20A:
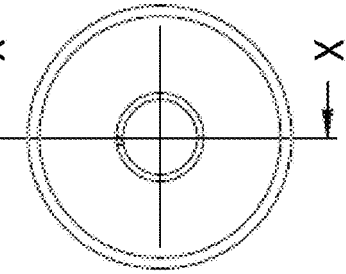

Referring to FIGS. 20-22, the ceramic cell, such as the T28 cCell from Shenzen Smoore, is a short cylinder 84 of ceramic material enclosing a helical heating wire 88 would along the inner bore of the cylinder. The heating wires are connected to a power bush 87. E-liquid is drawn through the porous ceramic walls of the cylinder 84, where it contacts the heated wires 88 and creates an atomized mist of e-liquid vapour in the atomizing chamber 43, from where it is drawn out by a user's inhalation. A ceramic cell is typically wrapped in cotton and then placed within a metal tube; e-liquid wets the cotton, forming an e-liquid reservoir around the ceramic coil, and is then wicked through the ceramic walls. Where the user manually drips e-liquid into this sort of atomizing unit, then it performs well. However, where the e-liquid reservoir around the ceramic coil is pumped under pressure, as it will be with the piezo-pump based system we have been describing, then a cotton wrap will leak and will also lead to very uneven wetting of the ceramic coil. We solve these problems by providing silicone end-caps 85 and 86 around the ceramic coil 84. The section of the ceramic coil 84 that is not covered by the silicone end-caps 85 and 86 is approximately 2 mm wide, but that is sufficient to receive e-liquid and distribute it evenly through the ceramic walls 84. A cotton strip may also be wrapped around this exposed section of the coil to reduce ingress of e-liquid.

Figure 23A:
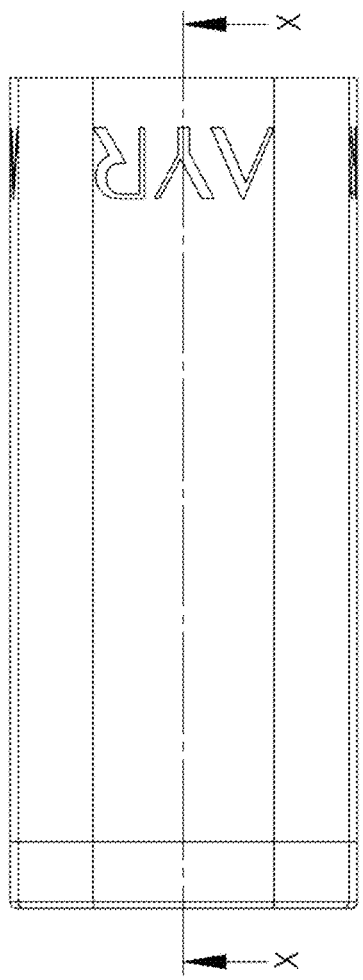
FIGS. 23A-C are side, side cross-section, and top views, respectively, of a ceramic cell atomizing unit with silicon end-pieces.
Figure 23C:
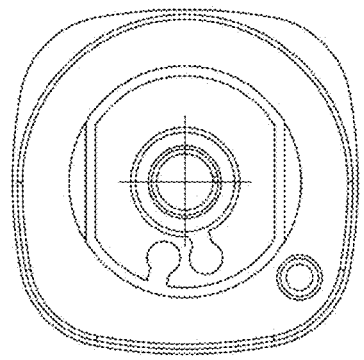
Figure 23B:
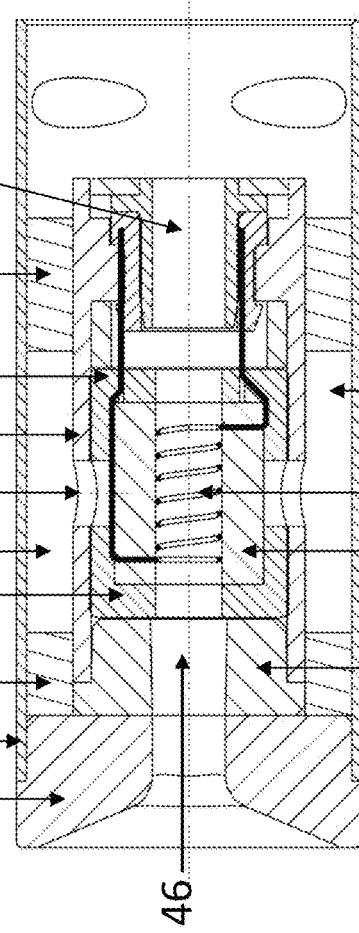

FIG. 23 shows a cross-sectional view of the components in the removable and user-replaceable mouthpiece 52, including the ceramic cell 84. The ceramic cell 84, with silicone end-caps 85, 86 is placed within metal tube 38. Metal tube 38 includes an opposing pair of circular e-liquid inlet apertures (approx. 2 mm in diameter) that line up over the section of the ceramic coil 84 that is not covered by the silicone end-caps 85, 86. Metal tube 38 is placed within tip tube 51; the annular region forms an e-liquid reservoir 44 around the metal tube 38; an e-liquid feed tube supplies e-liquid into this reservoir 44. A front seal 47 and back seal 49 seal off each end of the reservoir. A silicone rubber stopper 48 closes off one-end of the tube 38, and includes a central aperture 46 through which e-liquid vapour, created in the atomizing chamber 43, can pass. A front tip 89 defines the front face of the mouthpiece.

The silicone end caps make the coil more robust and impact resistant because they form protective silicone barriers. Because silicone is a good thermal insulator, it prevents the tip from getting too hot and burning a user's lips; it also improves the thermal effectiveness of the heating element. Instead of silicone, another suitable material, such as rubber or a soft plastic, or another type of elastomer, could be used. Material requirements are that it can (i) form an effective seal around the ceramic unit; (ii) withstand high temperatures; (iii) will not introduce any toxic compounds into the e-liquid and (iv) is easy to mold around the ceramic unit and (v) is thermally insulating.

Figure 24B:
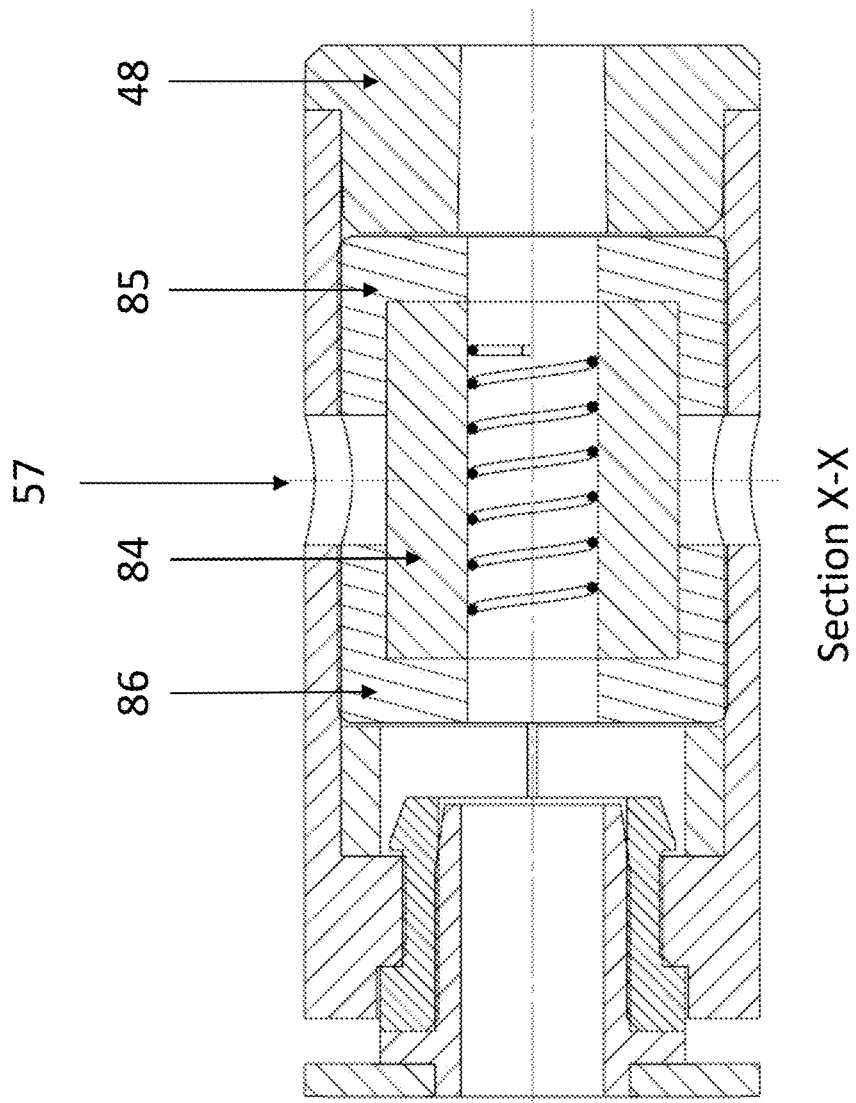
FIGS. 24A-B are top and side cross-section views, respectively, of a ceramic cell atomizing unit with silicon end-pieces.
Figure 24A:
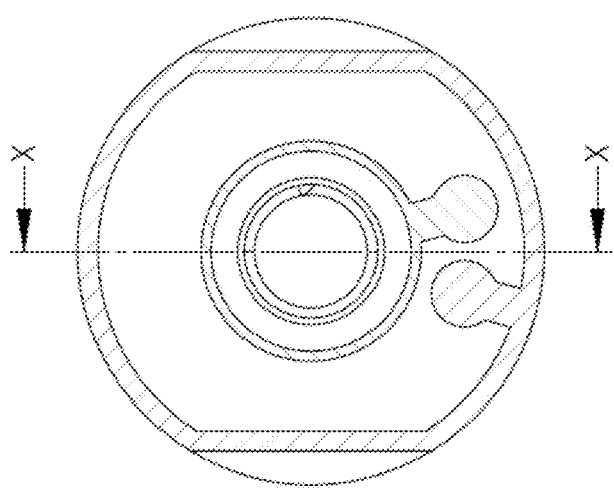
Figure 25:
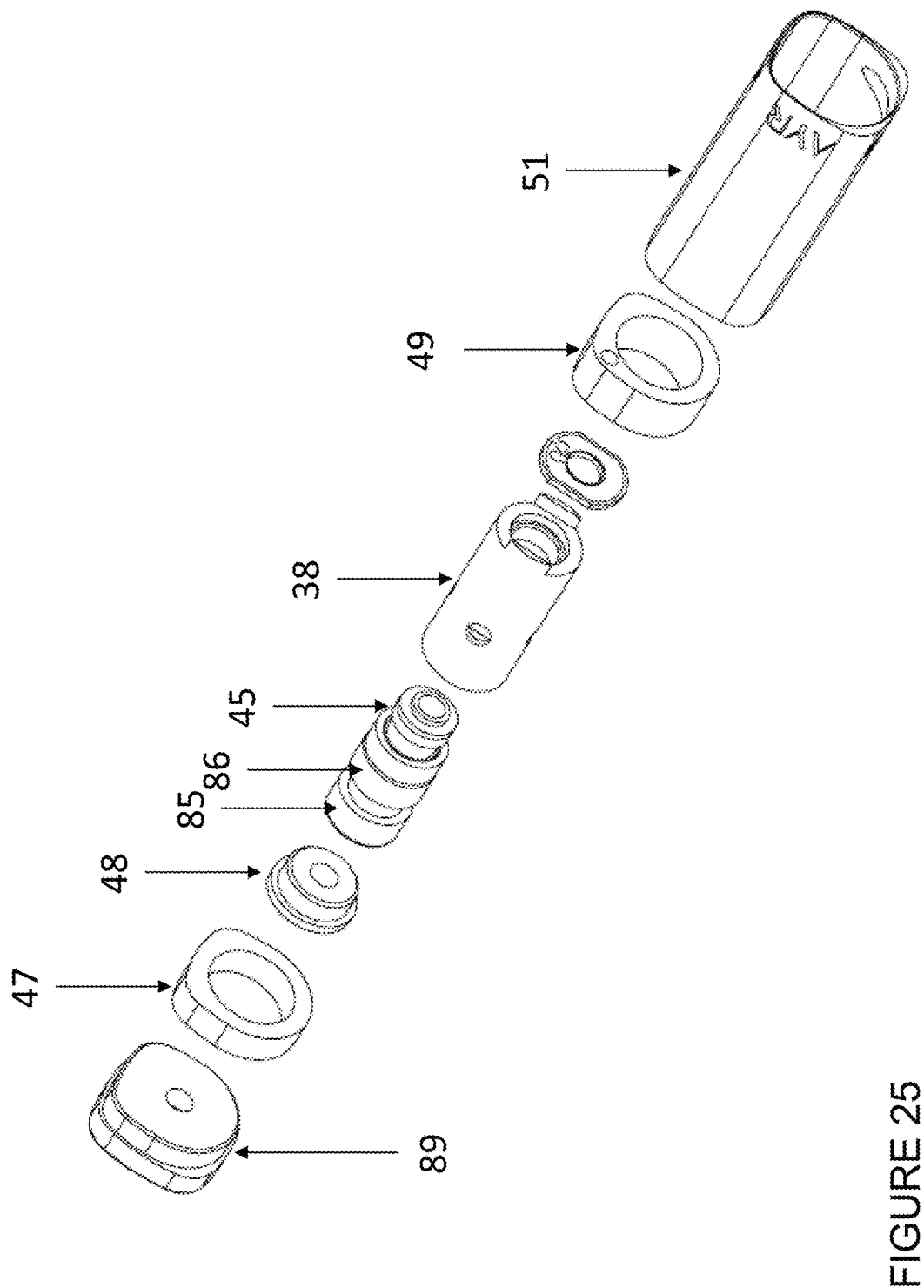
FIG. 25 is an exploded view of all the mouthpiece components shown in cross-section in FIG. 23.

FIG. 24 is an enlarged view cross-sectional view of the ceramic coil 84, silicone end-caps 85, 86 and silicone rubber stopper 48 (but facing in the opposite direction compared with FIG. 23). FIG. 25 is an exploded view of all the mouthpiece components shown in cross-section in FIG. 23.

Figure 26:
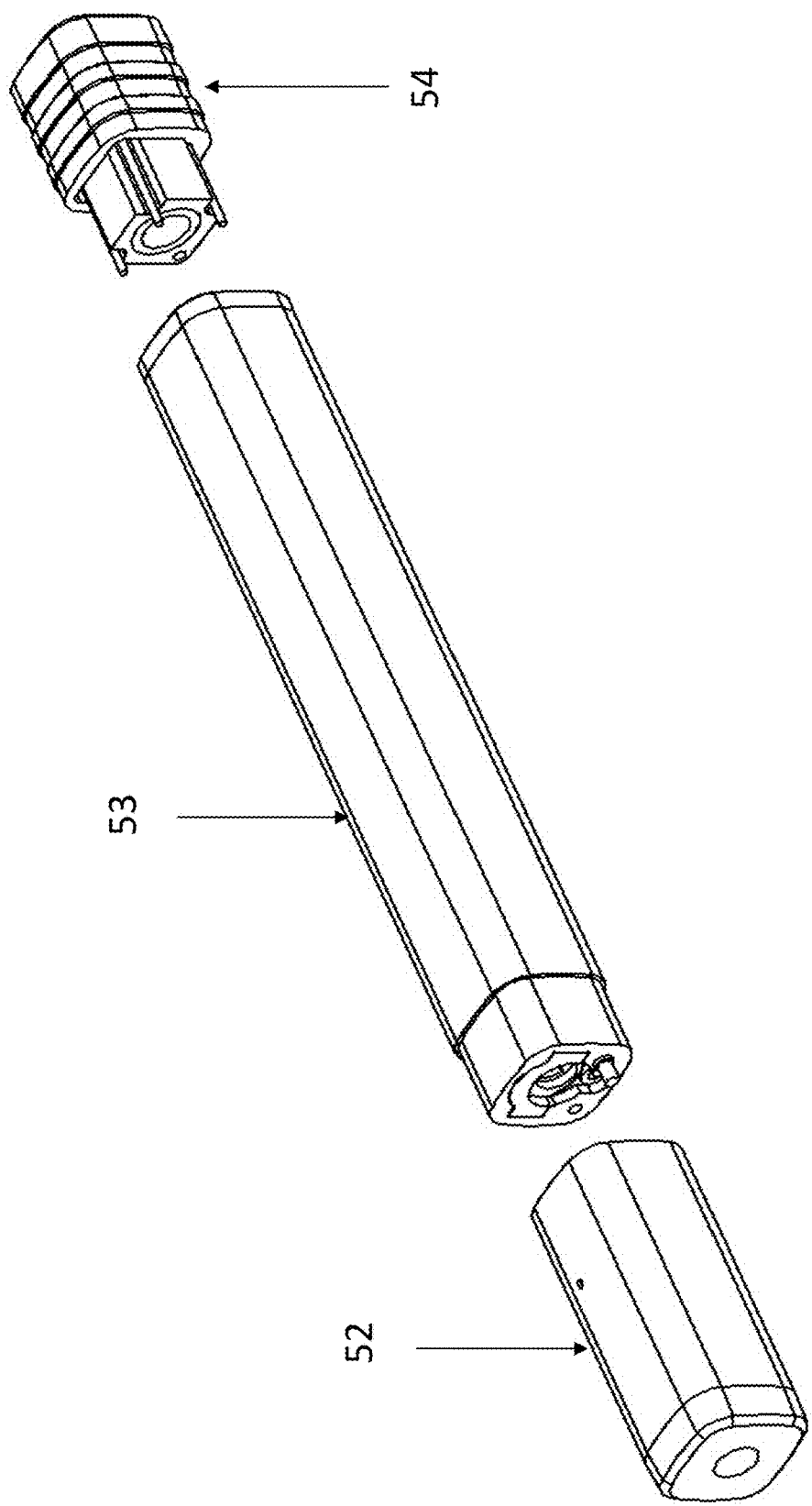
FIG. 26 is a perspective view of the major elements of the vaporiser, each separated.

FIG. 26 shows the entire electronic vaporiser PV, with the mouthpiece or coil holder 52 at one end (and which includes the components shown in FIG. 25); the main body tube 53, and at the far right hand end the e-liquid filling end, including a check valve assembly 54.

Figure 27:
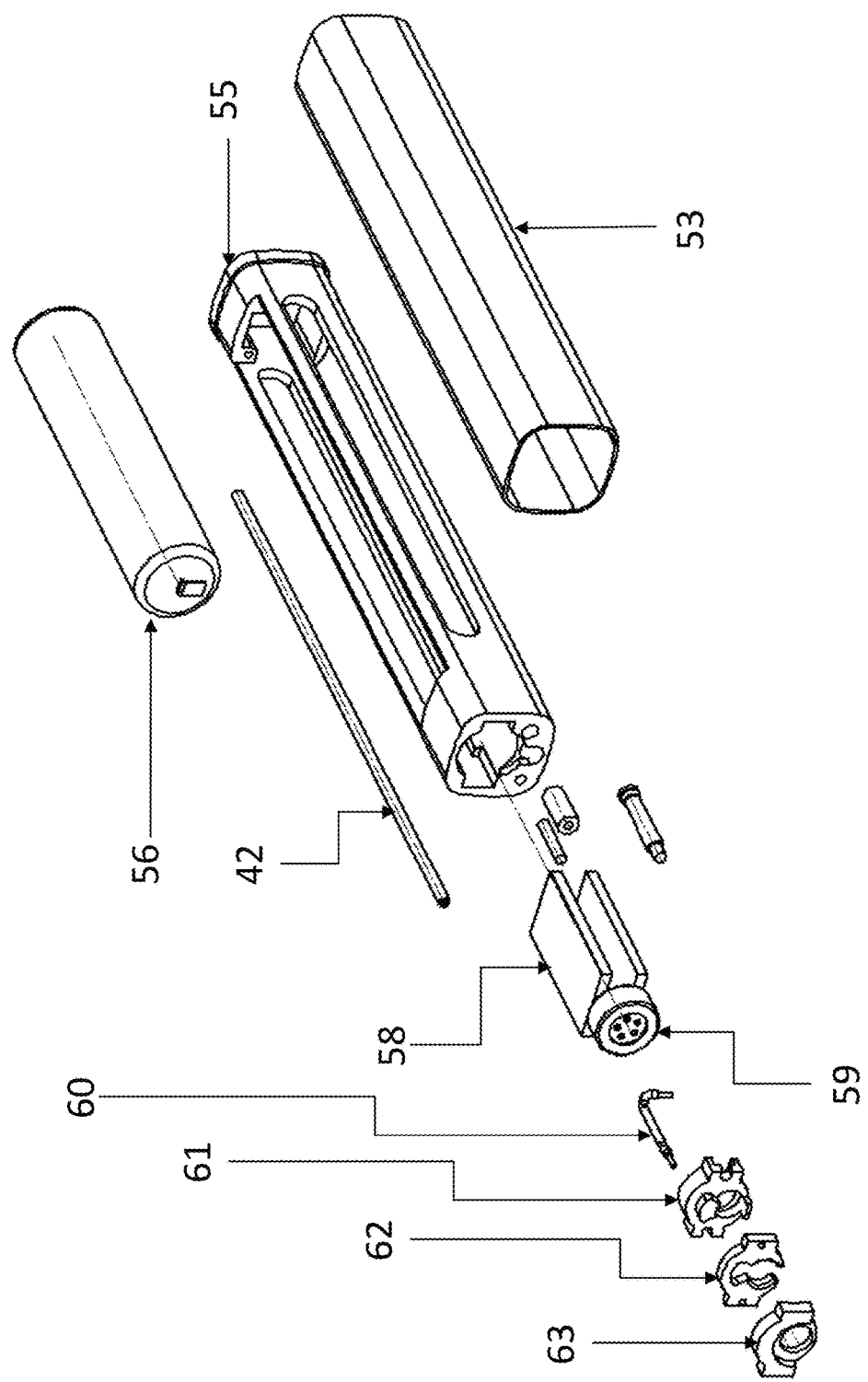
FIG. 27 is an exploded view of some of the major elements of the main body in the vaporizer, (and hence excluding the atomizing unit and mouthpiece, and the e-liquid filling mechanism).

FIG. 27 is an exploded view of the main body. It includes an external tube 53, and a chassis 55 which holds the main components, including a battery 56 and a fluid tube 42 that passes e-liquid from the e-liquid filling end (not shown) up through the main body and into the reservoir surrounding the wick and coil assembly (not shown). Within the chassis is a small electronics PCB 58, which includes a small processor or MCU and digital I/O; power and data I/O is via two metal rings sitting round the outside of the tube, as will be described later. PCB 58 can also be placed running above the battery, close to one of the main faces of the external tube 53.

The PCB 58 includes an IMU (inertial measurement unit) to detect when it is being lifted up and out of the case to control and/or track certain behaviours. The IMU is connected to a microcontroller (MCU) in the PV. The PV can also sense when a user is touching it—e.g. with a capacitive sensor. This provides a control signal to the MCU in the PV and hence enables movement associated with the user holding the PV to be distinguished from other movement of the PV.

An airflow sensor 59 is used to detect airflow and to activate the heating element. PCB also includes a temperature sensor. The airflow sensor 59 can also be used to operate as a spirometer—for example, measuring air flow and/or peak flow when the user is both sucking and blowing into the PV, and without activating the vaping function. This could be very useful for smokers with compromised lung functioning who wish to have a simple way of tracking the improvement in lung function that is very likely associated with giving up smoking; this can be an added motivation to continue with a smoking cessation programme based on using this device. The spirometer data captured by the airflow sensor can be sent to the user's app and displayed on the smartphone running the app and also shared with a physician.

The MCU in the PV can measure or estimate coil resistance; if the coil resistance is higher than some limit we can say that the coil needs to be replaced. Likewise, if the resistance starts to fluctuate, then that is also an indication that the coil needs replacing.

The MCU in the PV directly measures current and voltage delivered to the coil; it calculates coil resistance from this data. We have empirically mapped resistance to temperature for various coil/atomizing combinations and can store that map with the memory accessible by the MCU, enabling the MCU in the PV to estimate coil temperature and ensure that it is optimal. This is especially useful during 'power' mode when increased power is delivered to the coil as it then becomes important to be able to ensure that the coil temperature is not so high that undesirable compounds are produced.

Another feature is that each specific type of coil (e.g. design, materials, type of heating coil etc.) has a unique resistance profile which can be seen when a small current is passed through the coil (this is done momentarily before the full current for heating purposes is applied). This resistance profile is detected by the microcontroller, which in turn compares it to stored profiles to find the best match; the microcontroller then uses knowledge of the likely type of coil being used to ensure that it is used optimally—for example, different coil types could have different optimal operating temperatures and maximum safe temperatures. For a typical Kanthal wire coil, we have found that the optimal temperature is approximately 130° C. with a 60% to 40% VG mixture, and a relatively small water component; the MCU is able to determine the coil temperature through empirical mapping of the detected resistance against previously calculated or directly measured temperatures; accuracy is approximately ±10° C. or better. We set the maximum coil temperature at 150° C. since temperatures higher than 160° C. could be associated with the release of undesirable contaminants. Different optimal and maximum temperatures will be a function of the specific coil material and coil assembly design (e.g. a ceramic coil can operate at higher temperatures), and the e-liquid being used. Since the specific type of e-liquid (including flavours, water content, PV/VG mix etc.) being used by the device is known from data in the cartridge, this data is used by the MCU to set the optimal and maximum temperatures.

Another benefit to detecting or inferring the coil temperature is that we can rapidly compensate for high air-flow rates, which tend to cool a coil down quite quickly, and also very cold ambient temperatures. The PV also includes an integral temperature sensor measuring ambient temperature and feeding that data to the MCU; if the air is at −5° C., then the PV will deliver significantly more power to the coil than if the air temperature is +30° C., in order to achieve optimal 130° C. operating temperature. It may trigger a longer or more powerful pre-heat of the coil before the first inhalation is even detected by the air pressure sensor in the PV—for example, when the case is first opened or when the PV is first withdrawn from the case in very cold air, then pre-heat can start rapidly and at high power to ensure that the coil is at the optimal temperature when the first inhalation is taken.

The MCU in the PV also monitors each inhalation to measure e-liquid consumption and heating coil degradation.

Returning to the specific components shown in FIG. 27, a power wire 60 is shown, together with rear electrically insulating spacer 61, power plate 62 connected to the power wire 60, and front electrically insulating spacer 63. Power plate 62 provides power from battery 56 to the heating coil assembly.

Figure 28:
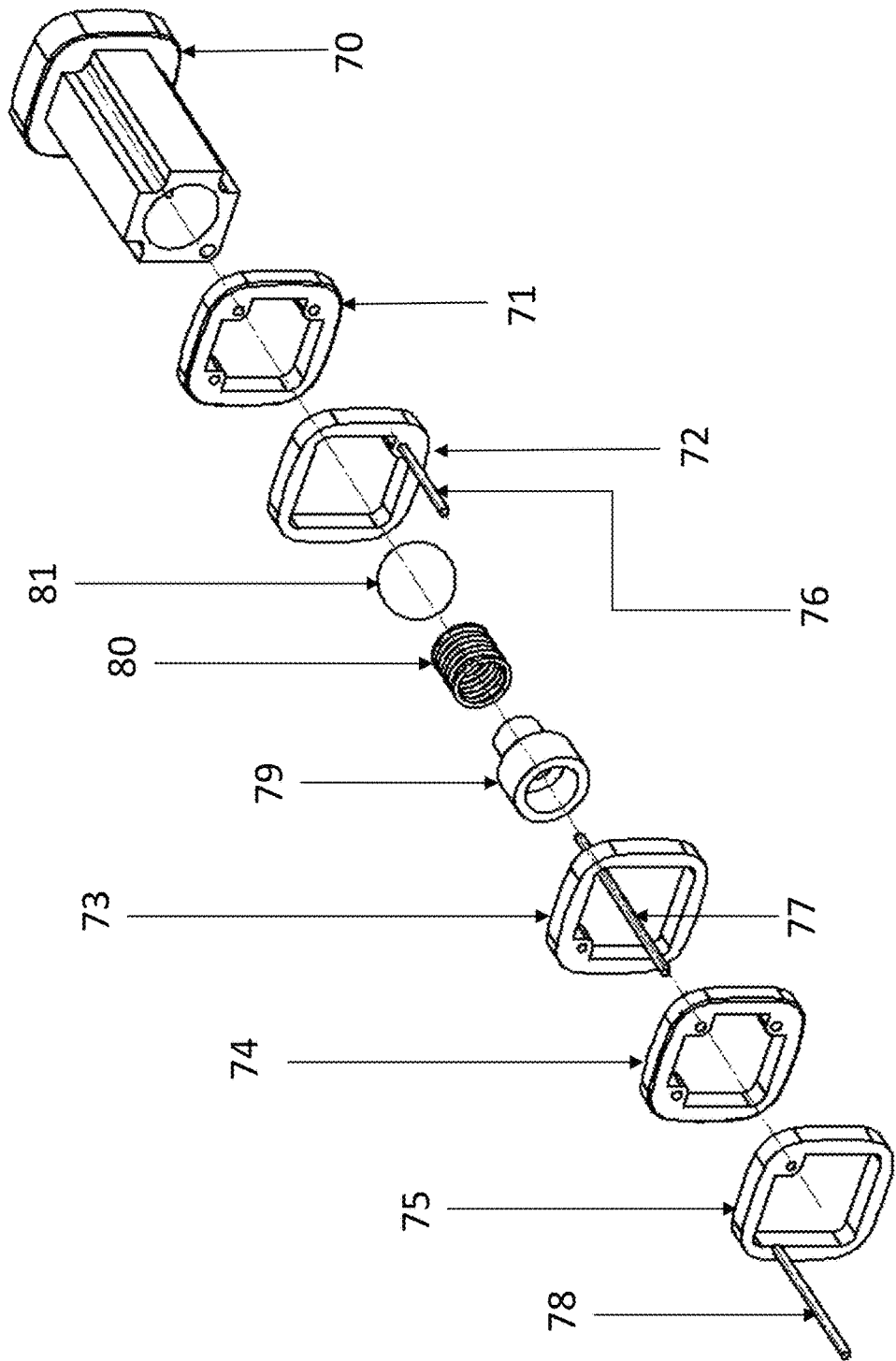
FIG. 28 is an exploded view of the major elements of the e-liquid filling end of the vaporiser.

FIG. 28 shows an exploded view of the e-liquid filling end, which is the check valve assembly 54 in FIG. 26. On check valve body 70 are mounted (moving from right to left in the Figure) a power ring 71, an insulating ring 72, a second power ring 73, a further insulating ring 74 and a third power ring 75. Electrical contact pins 76, 77 and 78, pass through the rings. Both power and data is sent via these power rings.

Inside the check valve body 70 is the e-liquid filling or stop valve. It includes spring 80 mounted on spring guide 79; the spring 80 biases stainless steel 316L ball 81, and ball 81 acts as the stop valve.

Figure 29B:
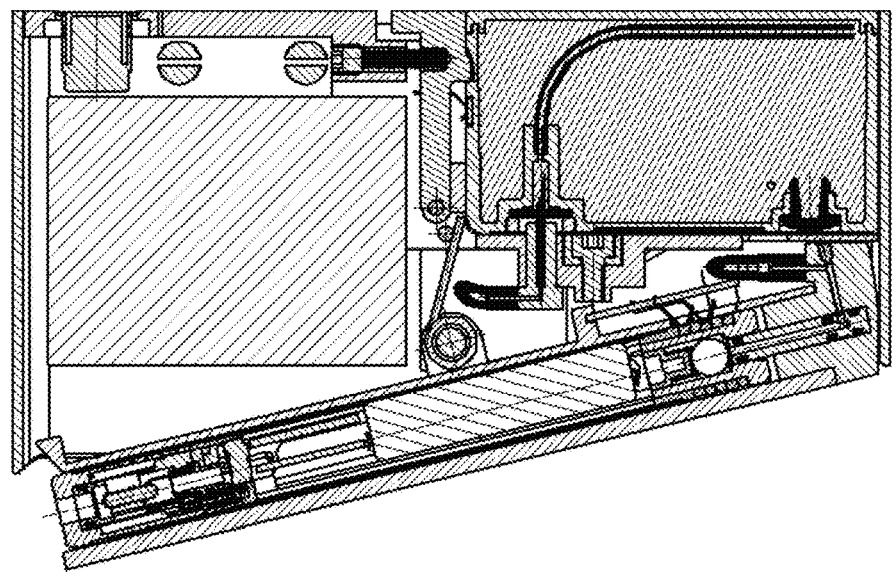
FIGS. 29A-B are cross-sectional views of the vaporiser in the case during filling with e-liquid
Figure 29A:
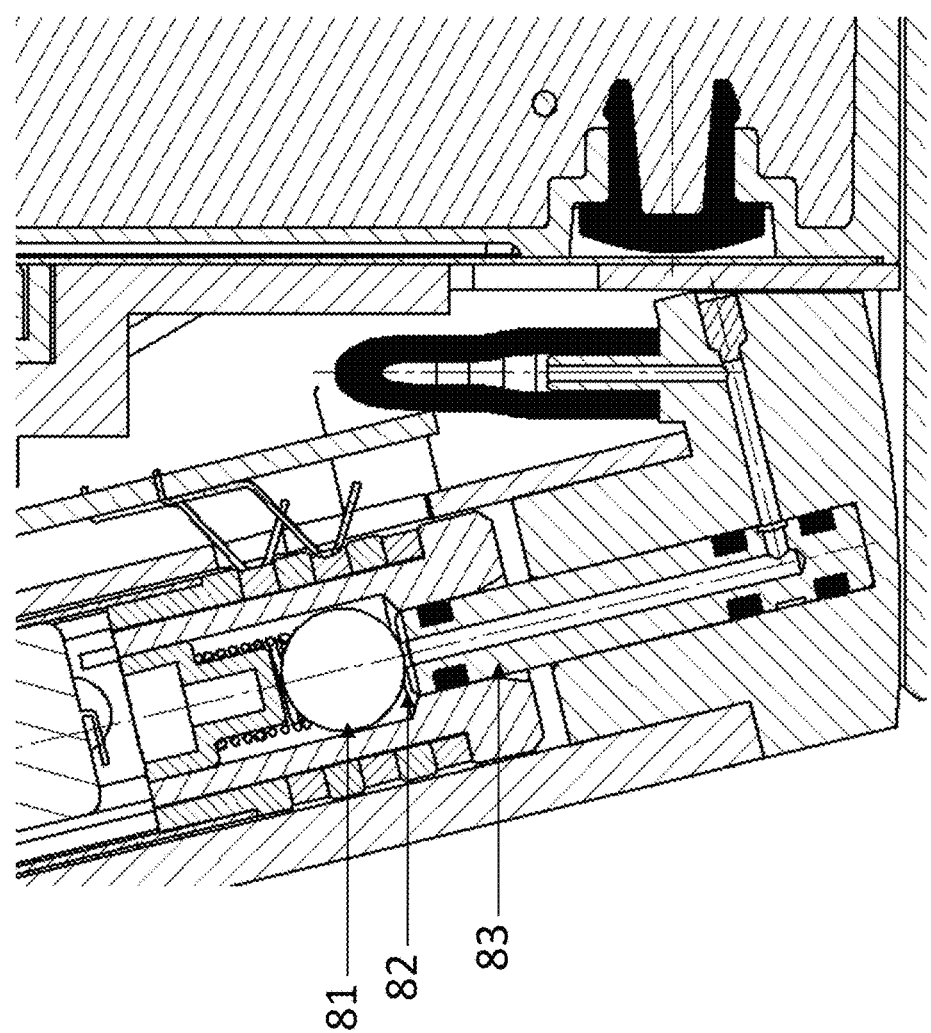
Figure 30:
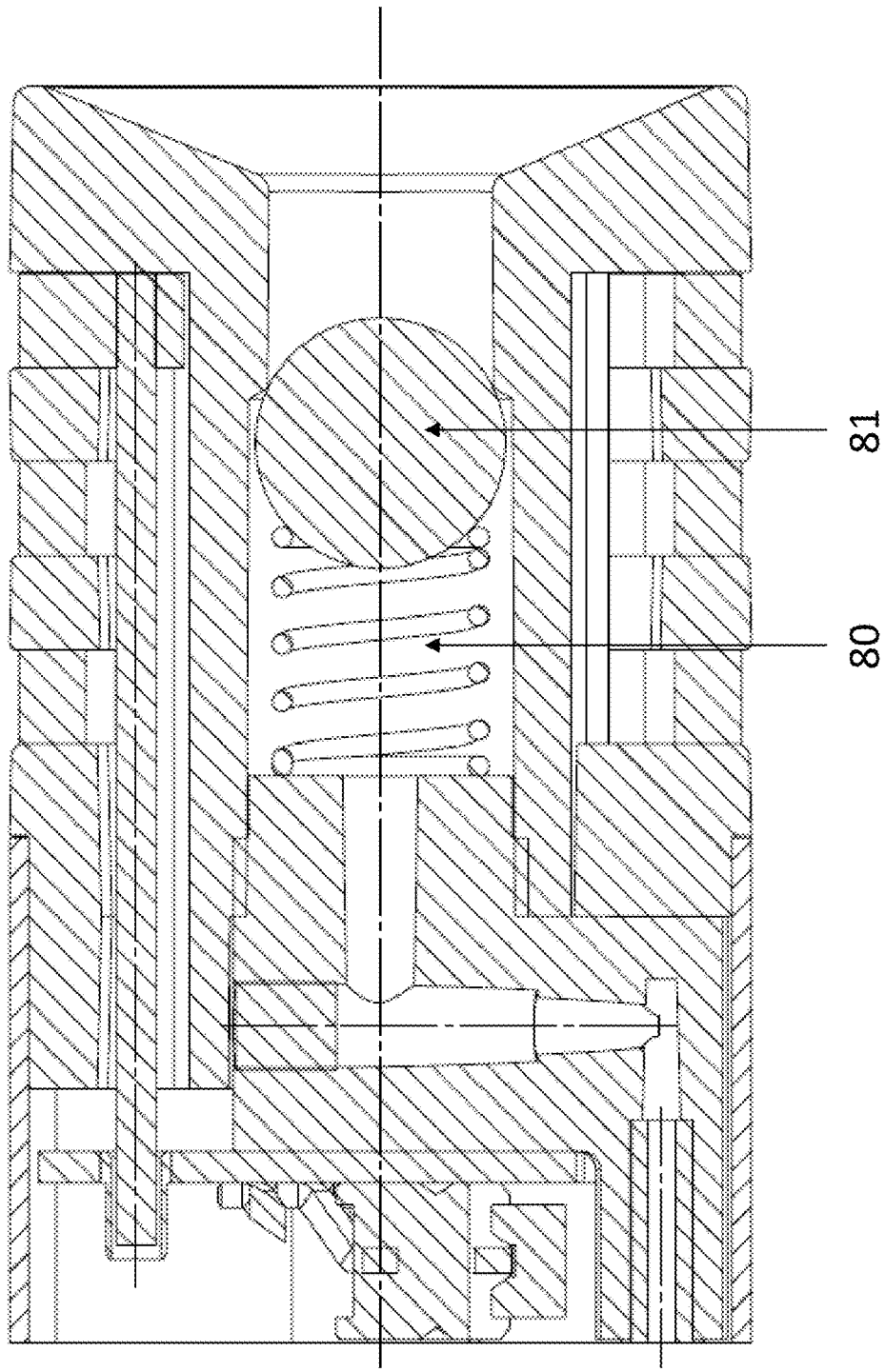
FIG. 30 is a cross-sectional view of the vaporizer showing the filling end.

The e-liquid filing mechanism in the PV is hence a simple aperture or nozzle sealed with spring biased stainless steel 316L ball. When the PV is fully inserted down into the hinged holder, as shown in FIG. 29, then a short filing tube or stem or spigot 83 at the base of the hinged holder pushes the ball 81 off its seat 82, exposing a fluid transfer path up from the filing tube, past the steel ball 81 and up through the PV to the 'child' reservoir around the wick and coil assembly.

The piezo pump can be activated manually by a user touching a button or other hard or soft switch on the case; alternatively, the case can be set up to automatically always fill the PV up whenever the PV is returned to the case and the case shut. In any event, filing automatically ends when the electronics in the case determines that the PV has sufficient e-liquid; for example, the electronics can monitor the power, current or voltage used by the micro-pump; this will start to rise as the PV reaches full capacity; the micro-pump can then be automatically switched off (or even momentarily switched into reverse to withdraw a small amount of e-liquid from the PV so there is no possibility of overfilling the PV).

A stop valve is included at the base of the spigot 83. This is a simple ball valve that is biased closed but is pushed open when the PV is fully inserted into the case to enable e-liquid to flow past it. Once the PV is removed, the ball valve returns to its closed position, preventing any liquid from spilling from the filing tube or spigot 83. This is shown in FIG. 9B.

A small, spring loaded, damped plug sits around the short filing tube or stem or spigot and causes the PV to be gently raised up when the hinged holder is opened; the PV rises about 5 mm to enable easy extraction from the case, mimicking the ritual of being offered a cigarette from a pack.

Figure 31:
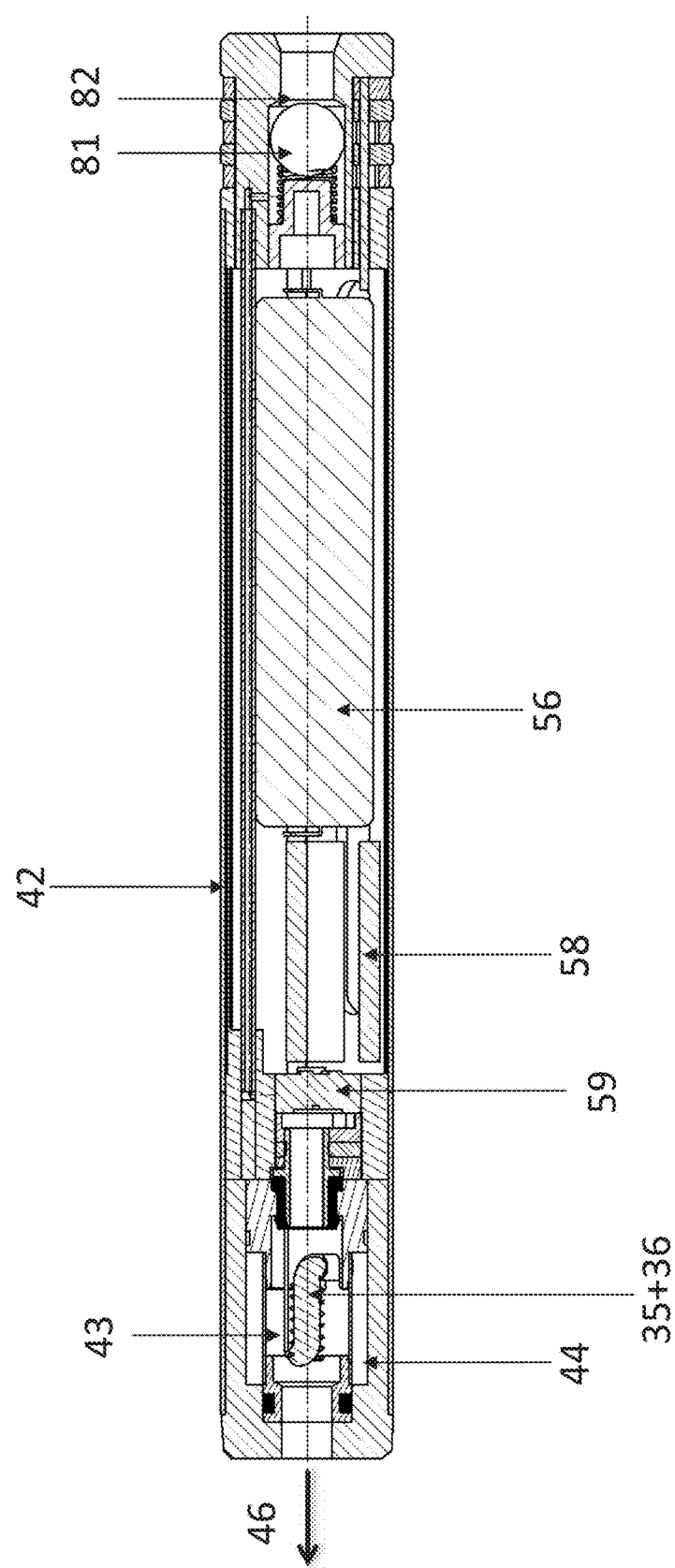
FIG. 31 is a cross-sectional view of the vaporizer with a cotton wick, seen from one angle.
Figure 32A:
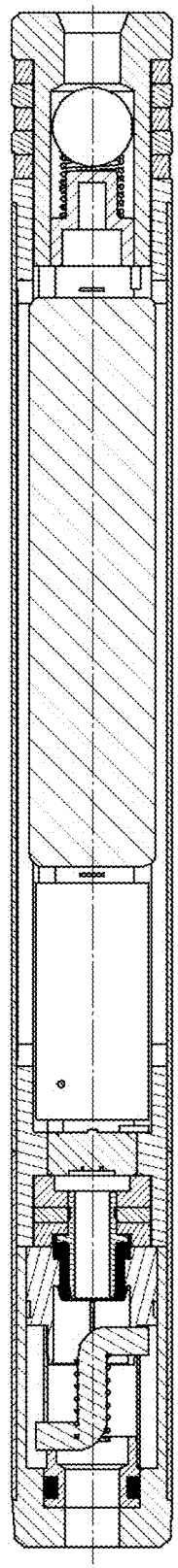
FIGS. 32A and 32B is a cross-sectional view of the cotton-wick vaporiser, seen from two different angles.
Figure 32B:
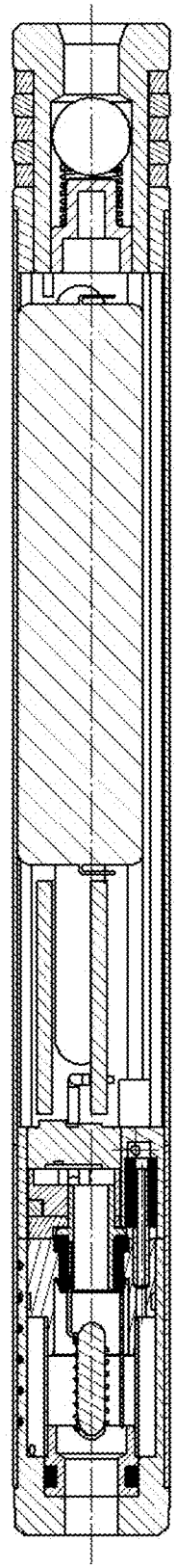

FIGS. 31 and 32A and 32B are various cross-sectional views through the PV that uses a cotton wick. As noted earlier, the PV (whether using a cotton wick or a ceramic cell) is the approximate same size as an ordinary cigarette, approximately 10 cm in length and 1 cm in width. The cross-section is square, with rounded corners (a 'squircle'): this shape enables a long, rectangular circuit board to be included in the PV and gives more design freedom for the placement of that PCB: if the PV casing, was circular, then the PCB would likely have to be mounted exactly across a diameter, and that would leave little room for a battery. So the square cross-section is a much better shape if a long PCB and battery is to be included inside the casing since it allows the PCB to be placed very close to one of the long faces of the PV, hence liberating volume for the battery. Also the PV includes a narrow pipe to transport e-liquid from the filling end to the reservoir around the heating element; this pipe can be accommodated in the corner of the PV casing just above the PCB. The square-profiled tube with rounded corners is hence an effective shape for including these elements.

The steel ball valve 81 is shown off its seat 82 although in normal vaping it will be biased against and sealing against its seat. When the PV is being filled with e-liquid, then e-liquid passes up past ball valve 81, along fluid tube 57 and into reservoir 44. E-liquid passes from reservoir 44 along wick 35 into the atomizing chamber. When the user inhales from the PV, then air is drawn in from air inlets in the PV (not shown, but typically positioned so that air is no drawn over the PCB) and is then sucked from air outlet 46, activating air pressure sensor 59; the MCU on board 58 then sends power from the battery 56 to the heating coil 36, which rises to 130° C. and rapidly heats the e-liquid in the wick 35, causing it to vapourise; the vapour is carried out from outlet 46 into the user's mouth.

FIGS. 33A to 33C are cross-sectional views of the PV that uses a ceramic cell 84. Moving from right to left, e-liquid is filled into the PV, moving past stainless steel ball valve 81, passing along feed tube 42 into e-liquid child reservoir 43 that surrounds the ceramic cell 84. E-liquid wicks into the ceramic cell 84 through apertures 57. Vapour is inhaled from outlet aperture 46. The entire mouthpiece unit 52 can be clipped off and on the body 53 if desired, enabling mouthpiece to be replaced if needed. The main PCB 58 sits over the battery 56.

Figure 34A:
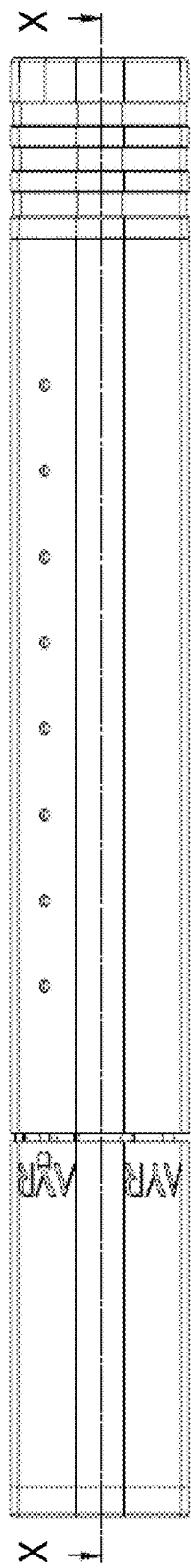
FIGS. 34A and 34B are views of the fully assembled vaporizer.
Figure 34B:
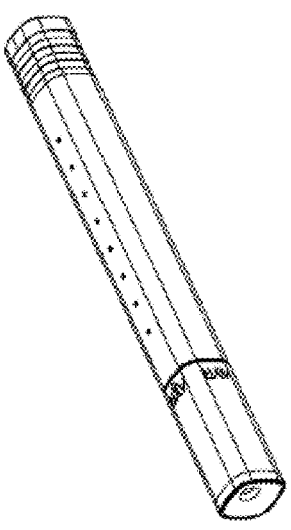

FIGS. 34A and 34B are external views of the ceramic cell-based PV.

Key features of the PV are the following:

PV Feature 1: PV includes an air pressure valve

PV Feature 2: PV includes a mechanical valve that is pushed up from its seat when filling takes place PV Feature 3: PV or case has an IMU PV Feature 4: The PV includes a touch sensor PV Feature 5: 'z' wick heating coil PV Feature 6: PV with replaceable wick and coil PV Feature 7: Pulsed power to the coil PV Feature 8: Detecting coil degradation PV Feature 9: Estimating coil temperature PV Feature 10: Monitoring each inhalation to measure e-liquid consumption and heating coil degradation PV Feature 11: Monitoring the coil characteristics to identity the type of coil installed.

PV Feature 12: Monitoring external or ambient temperature to ensure the coil is at optimal operating temperature PV Feature 13: Monitoring airflow to ensure the coil is at optimal operating temperature PV Feature 14: Using data from cartridge defining the e-liquid to control the heating of the coil PV Feature 15: The PV has a squircle cross-section PV Feature 16: Silicone caps to the ceramic cell Section D describes these features in more detail.

Figure 35:
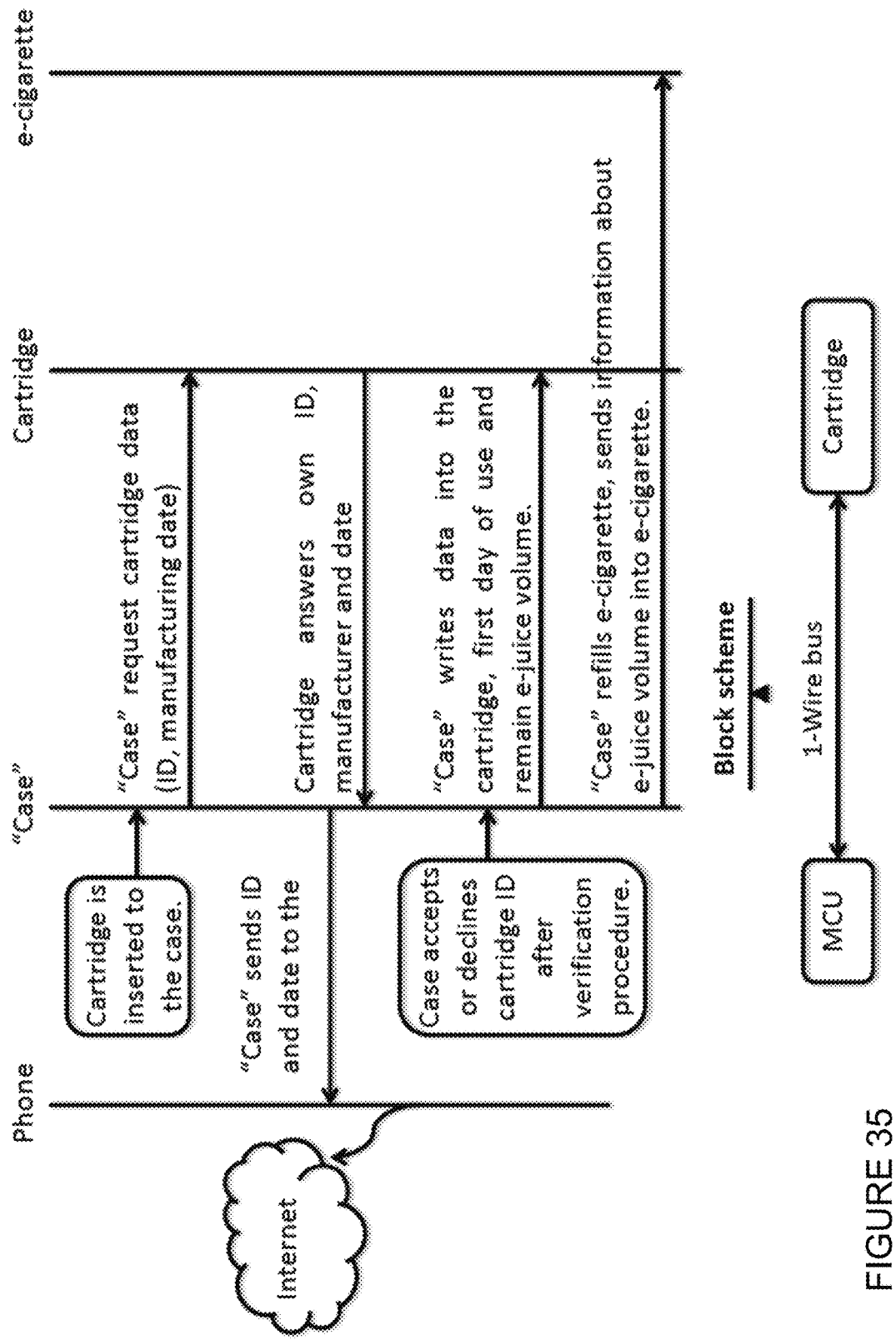
FIGS. 35 and 36 are flow charts showing the operation of the system.
Figure 36:
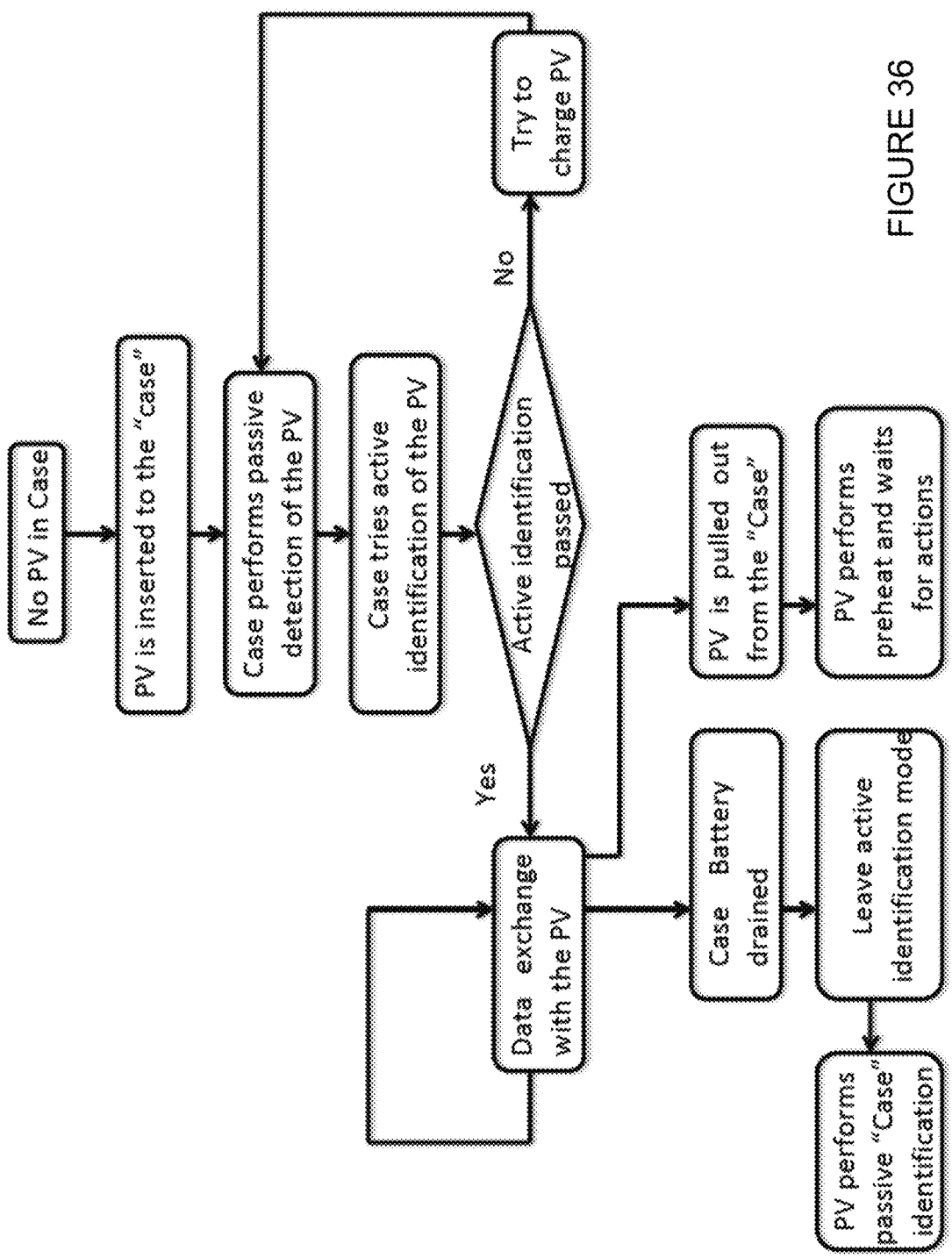

FIGS. 35 and 36 are flow charts explaining the operation of the electronic vaporiser.

Whilst this implementation is an electronic vaporiser system, the innovative features can also be applied in an inhalation system providing substances other than nicotine—for example, medication, such as asthma medication or any other drug that can be effectively delivered into the lungs, and also vitamins, and recreational drugs such as marijuana (where their use is lawful). The term 'e-liquid' can hence be generalized to any substance, including any medication, or legally permissible recreational drug.

Section C: Key Features

A number of interesting features are present in this electronic cigarette vaporiser system. We list them here, categorised into features relevant to the Case, the Cartridge and the PV. Note that each feature can be used with any one or more of the other features and no single feature is mandatory.

Case Features
Case Feature 1: The case includes a piezo-electric pump
Case Feature 2: The case or PV has a 'discrete' mode
Case Feature 3: The case or PV includes a 'power mode' with coil temperature monitoring
Case Feature 4: The case has a PV ejection mechanism
Case Feature 5: A non-contact sensor in the case detects PV release from the case
Case Feature 6: Sensor in the piezo pump feed line
Case Feature 7: Correcting any imbalance in the twin actuators in the piezo pump
Cartridge Features
Cartridge Feature 1: The cartridge or other form of parent reservoir includes an air pressure valve
Cartridge Feature 2: The cartridge includes a memory chip
Cartridge Feature 3: The cartridge includes two e-liquid apertures
Cartridge Feature 4: The cartridge stores the batch number of the e-liquid it is filled with and can be remotely disabled from using specific batch numbers
PV Features
PV Feature 1: PV includes an air pressure valve
PV Feature 2: PV includes a mechanical valve that is pushed up from its seat when filling takes place
PV Feature 3: PV or case has an IMU
PV Feature 4: The PV includes a touch sensor
PV Feature 5: 'z' wick heating coil
PV Feature 6: PV with replaceable wick and coil
PV Feature 7: Pulsed power to the coil
PV Feature 8: Detecting coil degradation
PV Feature 9: Estimating coil temperature
PV Feature 10: Monitoring each inhalation to measure e-liquid consumption and heating coil degradation
PV Feature 11: Monitoring the coil characteristics to identity the type of coil installed.
PV Feature 12: Monitoring external or ambient temperature to ensure the coil is at optimal operating temperature
PV Feature 13: Monitoring airflow to ensure the coil is at optimal operating temperature
PV Feature 14: Using data from the cartridge defining the e-liquid to control the heating of the coil
PV Feature 15: The PV has a squircle cross-section
PV Feature 16: Silicone caps to the ceramic cell In this section, we describe the key features of this electronic vaporiser system in more detail and generalise from the specific implementations.

Case Features 1-5
Case Feature 1:
The case includes a piezo-electric pump: the case (or the PV or the cartridge) includes a piezo-electric pump to transfer small but accurate quantities of e-liquid in from the cartridge or parent reservoir to a child reservoir in the PV. This enables mixing from multiple cartridges too. The piezo-electric pump can be used as the fluid transfer mechanism to transfer e-liquid from the cartridge or parent reservoir into the child reservoir in the PV. It can also be used in reverse to suck back out any residual e-liquid in the PV.

Because the amounts delivered can be accurately metered, this means that the PV (or case or cartridge or an associated application running on a smartphone) can accurately determine the total consumption of e-liquid and/or the amount of e-liquid remaining in a cartridge and also in the PV itself. This in turn can be used in the automatic re-ordering function—for example, when the system knows that the cartridge is down to its last 20% by volume of e-liquid, then the app running on the user's smartphone can prompt the user with a message asking if the user would like to order a replacement cartridge or cartridges. Low-cost piezo-electric pumps used ordinarily for delivering ink in an inkjet printer may be used, as well as more costly pumps, such as those made for pumping blood plasma. Note that the piezo-electric pump is quite a high cost item and so suitable for premium category electronic vaporiser devices. Where minimizing costs is critical, then a mechanical pumping arrangement, as for example described in WO 2015/128665, can be used instead.

The pump operates at low pressure, under 1 psi (higher pressures are possible) and has a flow rate of 0.4-0.6 mL per minute, and hence will fill a completely empty PV in 60-90 seconds (or half that if the PV has been used to vape a single session after its last complete filling since it is already half-filled). The pump can be activated manually by a user touching a button or other hard or soft switch on the case; alternatively, the case can be set up to automatically always fill the PV up whenever the PV is returned to the case and the case shut. In any event, filing automatically ends when the electronics in the case determines that the PV has sufficient e-liquid; for example, the electronics can monitor the power, current or voltage used by the micro-pump; this will start to rise as the PV reaches full capacity; the micro-pump can then be automatically switched off (or even momentarily switched into reverse to withdraw a small amount of e-liquid from the PV so there is no possibility of overfilling the PV). The micro-pump can also be operated in reverse, or with rapid forward and reverse pumping, to clear a blockage or clean the system.

A sensor can be placed in the inlet tube feeding the piezo-pump to determine if air or e-liquid is about to enter the piezo-pump: the pumping frequency for e-liquid has to be significantly lower for efficient pumping of e-liquid; or other parameters can also be altered to ensure pumping effectiveness. Also, the viscosity of the e-liquid affects the piezo-pump and as the viscosity increases, the pumping frequency should be lowered.

The viscosity could be directly measured using an appropriate sensor (e.g. a MEMS sensor) or could be inferred from the ambient temperature and/or the temperature of the e-liquid (viscosity is temperature dependent).

We can generalise this feature as follows:

An electronic cigarette vaporiser system including a single piezo-electric pump that both withdraws liquid from a cartridge or chamber and also pumps controlled amounts of liquid into another reservoir in the electronic vaporiser.

Optional features include one or more of the following:
 the reservoir surrounds or leads to an atomizing chamber.
 the pump is in a case that enables a removeable, personal vaporiser to be stored, and a cartridge is attached to or inserted into the case, and the case both re-fills the vaporiser with e-liquid and re-charges a battery in the vaporiser.

the cartridge or chamber is removably insertable or attachable to the case.

the cartridge or chamber is removably insertable or integral to the vaporiser the pump is a piezo-electric pump, for example of the sort used to transfer ink in an inkjet printer or to pump other liquids such as blood plasma the pump is a piezo-electric pump that can reliably pump liquids across the viscosity range of e-liquids between −10 degrees C. and +40 degrees C.

the pump has an input feed line connected to the cartridge and an output feedline connected to a filling nozzle that engages with the PV or vaporiser when the vaporiser is positioned in the case for re-filling with e-liquid the pump is included in the vaporiser and the vaporiser also includes the cartridge.

the cartridge is not pressurized to a degree sufficient to expel liquid.

the cartridge is filled with an inert gas at manufacture.

the pump (or its control or driver circuitry) provides data to an electronics module (e.g. MCU in the PV and/or case and/or elsewhere, such as the connected smartphone) that enables the module to determine, estimate or infer the amount of liquid pumped from the cartridge or left remaining in the cartridge (e.g. using a knowledge of the total number of pumping cycles and the amount pumped per cycle, or the pumping frequency, duration of pumping and the amount pumped per cycle, or other relevant data; the ambient temperature and temperature of the e-liquid can also be measured or inferred and that result also factored in).

the module uses this data defining the amount of liquid consumed to assess whether the quantity is within user-defined limits; if the liquid consumed is at or above the defined limit, the module can cause a warning message to be displayed, e.g. on the case, the PV or the connected smartphone application.

Note that the device could also be stopped from working entirely if excessive nicotine appears to have been consumed, although that would be an extreme measure and possibly also counter-productive since it could simply prompt the user to smoke a cigarette instead.

the pump (or its control or driver circuitry) or a sensor in line with the pump provides data to an electronics module that enables the module to determine, estimate or infer when pumping liquid to the reservoir in the personal vaporiser should cease to prevent over-filling the personal vaporiser.

data is the current drawn by the pump or electrical resistance offered by the pump, or the output of a pressure sensor in line with the pump electronics module uses the data as well as data relating to the amount of liquid pumped into the personal vaporiser to determine, estimate or infer when pumping liquid to the reservoir in the personal vaporiser should cease.

the pump (or its control or driver circuitry) provides data to an electronics module that enables the module to determine, estimate or infer whether the cartridge has been unlawfully filled because it is providing a quantity of liquid that exceeds the normal capacity of the cartridge.

the pump has a flow rate of between 0.4 mL and 0.6 mL per minute.

the pump delivers a pressure of under 1 psi, or under 5 psi, with e-liquid.

the pump is activated by a user touching a panel or button or switch on the case.

the pump can be operated in reverse to withdraw liquid from the personal vaporiser, for example to minimize contamination of liquid when switching flavours.

the pump can also be operated in reverse, or with rapid forward and reverse pumping, to clear a blockage or clean the system.

the pump is activated automatically whenever a personal vaporiser is placed into a storage or filling mode, e.g. closed into a storage case.

the pump can be prevented from pumping liquid from a specific cartridge in the case where that cartridge is identified as defective or as including defective or contaminated e-liquid.

Operating parameters of the pump are automatically altered depending on whether it is pumping air or e-liquid Operating parameters of the pump are automatically altered depending on the ambient temperature and/or the e-liquid temperature and/or the e-liquid viscosity The operating parameters include the actuator frequency the electronic vaporiser system is an e-cigarette system and the liquid is an e-liquid.

the electronic vaporiser is a medicinally approved nicotine drug delivery system.

the electronic vaporiser is the same approximate size as a cigarette the electronic vaporiser is filled from a user-replaceable, closed liquid cartridge the electronic vaporiser is refillable with e-liquid only when inserted, whole and intact and not dis-assembled, into a re-fill case that includes a fluid transfer mechanism to transfer liquid into the vaporiser.

Other aspects include the following:

An e-cig system including a piezo-electric micropump operating to extract e-liquid from a user-removable cartridge.

An e-cig system including a piezo-electric micropump operating to transfer e-liquid into a reservoir in a PV.

An e-cig system including a peristaltic micropump operating to extract e-liquid from a user-removable cartridge.

An e-cig system including a peristaltic micropump operating to transfer e-liquid into a reservoir in a PV.

Note that there may be a single pump to both extract and transfer, or one pump for each operation. Another aspect is therefore an electronic vaporiser system including a single piezo-electric pump to withdraw e-liquid from an e-liquid cartridge or chamber and a further piezo-electric pump to pump controlled amounts of e-liquid into another reservoir in the electronic vaporiser.

Another aspect is: A storage case for an electronic cigarette vaporiser, in which the case includes:

(a) a user-replaceable, closed e-liquid cartridge that slots into or otherwise attaches to the case, the cartridge including a septum that seals an aperture in the body of the cartridge;

(b) a needle or stem positioned to puncture or penetrate the septum when the cartridge is moved into position;

(c) a piezo-pump connected to the needle or stem to withdraw e-liquid from the cartridge and to pump it to the vaporiser when the vaporiser is positioned in the storage case and the user either activates a control switch (e.g. on the case, and/or on an app) or (ii) e-liquid filling is started automatically.

The case may include several different cartridges all feeding the pump, via a mixer unit.

Another aspect is: A case for storing, re-filling with e-liquid and re-charging an electronic cigarette vaporiser, in which the case includes a piezo-electric pump to transfer quantities of e-liquid to a child reservoir in the personal vaporiser.

Other optional features:
the piezo-electric pump is used in reverse to suck back out any residual e-liquid in the personal vaporiser.
the amount of e-liquid transferred by the piezo-electric pump is metered.
the metered data enables the total consumption of e-liquid and/or the amount of e-liquid remaining in a cartridge and also in the personal vaporiser itself to be measured or assessed.
the metered data is used in an automatic re-ordering function for new cartridges.
the piezo-electric pump is a piezo-electric pump of the kind used ordinarily for delivering ink in an inkjet printer or to pump blood plasma.
the electronic vaporiser system is an e-cigarette system.
the electronic vaporiser is a medicinally approved nicotine drug delivery system.

One final aspect: A piezo-electric pump adapted to be operable to withdraw e-liquid from an e-liquid cartridge or reservoir and to pump controlled amounts of e-liquid into a reservoir or chamber in an electronic cigarette vaporiser. The adaptation can be the specific choice of materials used in the piezo-pump, in order for there to be nicotine compatibility, such as the use of polyimide materials.

Case Feature 2:

Case or PV has a 'discrete' mode: PV includes a 'discrete mode'—e.g. to reduce the amount of vapour produced, the user can activate a button or sensor on the PV (or case, or connected app) and that alters the operation of the operation of the atomising device in such a way as to decrease the vapour produced—for example, it could reduce the power used, or increase the VG proportion compared to PG, if that is possible—e.g. the case or PV can mix differing proportions of PG and VG, or alter the frequency or other operational parameters (e.g. duty cycle) of a piezo-electric, thermal bubble jet or ultrasonic atomiser. Consequently, the density or thickness of the vapour produced by the PV can be significantly reduced; this is particularly useful indoors, when the user might wish to vape very discretely. The strength of the 'hit' can also be decreased too, because the amount of nicotine inhaled will be reduced; this can be useful where the user wishes to reduce their nicotine consumption.

We can generalise this feature as follows:

An electronic cigarette vaporiser system operable in a 'discrete' mode to reduce the amount of vapour produced by a vaporiser that forms part of the system, compared to a normal mode.

Optional features include one or more of the following:
the 'discrete' mode causes the vapour produced to be less visible or noticeable, compared to a normal mode.
the system include a button or sensor that, if selected or activated, alters the operation of the vaporiser in such a way as to decrease the vapour produced.
the user can activate a button or sensor on the system (e.g. on the PV, or case) or connected application running on a connected smartphone or other device, that alters the operation of an atomising or heating device in such a way as to decrease the vapour produced, compared to a normal mode.
the 'discrete' mode involves reducing the power delivered to or used by the atomising or heating unit, compared to a normal mode, e.g. by 10%.
the atomising or heating unit is powered using a pulsed signal and the duty cycle of the pulsed signal is varied to decrease the power, compared to a normal mode, e.g. by 10%.
the pulsed signal is a PWM (pulse width modulated) signal.
the 'discrete' mode involves increasing the VG (vegetable glycerin) proportion compared to PG (propylene glycol) in the e-liquid being vaporised, compared to a normal mode.
the 'discrete' mode involves altering the frequency or other operational parameters (e.g. duty cycle) of a piezo-electric, thermal bubble jet or ultrasonic atomiser.
the 'discrete' mode involves reducing the maximum temperature of the heating element in the atomizing unit, compared to a normal mode, e.g. by 10%.
a microcontroller in the vaporiser monitors the temperature of the heating element, e.g. to ensure that it remains within the range that delivers a good vaping experience but with lower amounts of vapour.
the electronic vaporiser system is an e-cigarette system.
the electronic vaporiser system is a medicinally approved nicotine drug delivery system.
the electronic vaporiser is the same approximate size as a cigarette
the electronic vaporiser is the same approximate size as a cigarette and includes no control buttons
the electronic vaporiser has a square or rectangular cross-section with rounded corners and includes a long PCB inserted lengthwise into the vaporiser
the electronic vaporiser is filled from a user-replaceable e-liquid cartridge
the electronic vaporiser is refillable with e-liquid only when inserted, whole and intact and not dis-assembled, into a re-fill case that includes a fluid transfer mechanism to transfer e-liquid into the vaporiser
the electronic vaporiser is filled with e-liquid using a piezo-electric pump
the electronic vaporiser includes lights that illuminate to indicate the amount of e-liquid consumed, and these lights are dimmed or turned off if the vaporiser is in 'discrete' mode.

Case Feature 3:

Case or PV includes a 'power mode'—e.g. to increase the amount of vapour produced, the user can activate a button or sensor on the case or PV, or connected app and that alters the operation of the operation of the atomising device in such a way as to increase the vapour produced—for example, it may increase the power used, or increase the frequency or duty cycle of a piezo-electric, thermal bubble jet or ultrasonic atomizer, but whilst monitoring the coil temperature to ensure that excessively high temperatures, associated with undesirable compounds in the vapour, are not reached.

Additionally, or alternatively, the system may increase the PG proportion compared to VG, if that is possible—e.g. the case or PV can mix differing proportions of PG and VG, Consequently, the density or thickness of the vapour produced by the PV can be significantly increased; the strength of the 'hit' can also be increased too, because the amount of nicotine inhaled will be greater.

We can generalise this feature as follows:

An electronic cigarette vaporiser system operable in a 'power' mode to increase the amount of vapour produced by a vaporiser that forms part of the system, whilst monitoring the temperature of a heating element in the vaporiser to ensure that excessively high temperatures, associated with undesirable compounds in the vapour produced by the heating element, are not reached.

Optional features include one or more of the following:
- the system includes a button or sensor that alters the operation of the heating element in such a way as to increase the vapour produced, compared to normal.
- the button or sensor is on the vaporiser, or a case for the vaporiser, or a connected application running on a connected smartphone or other device.
- the PV includes no 'power mode' button.
- the PV includes no other control buttons.
- the 'power' mode involves increasing the PG proportion compared to VG of the e-liquid being vaporised.
- the 'power' mode involves altering the frequency or other operational parameters (e.g. duty cycle) of a piezo-electric, thermal bubble jet or ultrasonic atomizer, whilst monitoring the temperature of the heating element to ensure it remains at a safe temperature.
- the vaporiser includes or co-operates with an electronics module that (i) detects characteristics of the resistance of the heating element and (ii) uses an inference of temperature derived from that resistance as a control input.
- the temperature of the heating element is estimated from data stored in the electronics module that has been empirically obtained for a specific heating coil design.
- the electronics module controls the power delivered to the heating element to ensure that it is no higher than approximately 130° C. or 10% above normal
- the electronics module controls the power delivered using the resistance measurement and does not calculate any derived temperature.
- The system includes a 'discrete' mode to decrease the amount of vapour produced by a vaporiser that forms part of the system, compared to normal
- the electronic vaporiser system is an e-cigarette system.
- the electronic vaporiser is a medicinally approved nicotine drug delivery system.
- coil temperature monitoring is achieved as described below (see 'PV Feature 9')
- the electronic vaporiser is the same approximate size as a cigarette
- the electronic vaporiser is the same approximate size as a cigarette and includes no control buttons
- the electronic vaporiser has a square or rectangular cross-section with rounded corners and includes a long PCB inserted lengthwise into the vaporiser
- the electronic vaporiser is filled from a user-replaceable e-liquid cartridge
- the electronic vaporiser is refillable with e-liquid only when inserted, whole and intact and not dis-assembled, into a re-fill case that includes a fluid transfer mechanism to transfer e-liquid into the vaporiser
- the electronic vaporiser is filled with e-liquid using a piezo-electric pump
- the electronic vaporiser includes lights that illuminate to indicate the amount of e-liquid consumed, and these lights are set to shine more brightly if the vaporiser is in 'power' mode, compared to their normal level of brightness.

Case Feature 4:

Case has a PV ejection mechanism: The case includes an automatic lifting mechanism (e.g. magnetic or spring-based) that, when the case is opened, gently lifts the PV up a few mm from the case to enable a user to easily grasp it and may also prevent it from falling out if tipped upside down. A mechanical lifting system could be a simple pivoting lever that contacts a part of the PV (e.g. its front face); a damped spring is placed under tension if the PV is inserted fully into the case; when the PV is released from the case (e.g. by pushing a release button), then the lever cause the PV to gently rise up by about, for example, 12 mm. A magnetic lifting mechanism could involve a permanent magnet at one part of the PV and an adjacent electro-magnet placed in the case and powered by the main battery in the case; slowly energising the electro-magnet when the PV needs to be released causes the PV to gracefully rise up out of the case.

We can generalise this feature as follows:

A case for an electronic cigarette vaporiser, the case including an automatic lifting mechanism (e.g. magnetic or spring-based) that gently lifts the vaporiser up a few mm from the case to enable a user to easily grasp the vaporiser and withdraw it from the case.

Optional features include one or more of the following:
- the case both re-fills the vaporiser with e-liquid and also re-charges a battery in the vaporiser.
- the lifting mechanism is a pivoting lever that contacts a part of the vaporiser (e.g. its front face) and a damped spring that is placed under tension if the vaporiser is inserted fully into the case, so that when the vaporiser is released from the case, then the lever causes the vaporiser to gently rise up by about, for example, 12 mm.
- the lifting mechanism is a permanent magnet at one part of the vaporiser and an adjacent electro-magnet placed in the case and powered by the main battery in the case; so that slowly energising the electro-magnet when the PV needs to be released causes the vaporiser to gracefully rise up out of the case.
- the lifting mechanism is a damped spring that is placed under tension when the vaporiser is inserted fully into the case or the case is closed; and a latch secures the spring in its tensioned state and releases the spring when the case is opened, enabling the spring to extend, gently lifting the vaporiser up 1 cm approximately so that it can be easily grasped.
- the case includes a liquid filling nozzle or stem or aperture that engages with the vaporiser and enables e-liquid to pass from a reservoir or cartridge in the case into the vaporiser.
- the lifting mechanism is automatically activated when the case is opened.
- the case includes a hinged holder into which a vaporiser is slid for storage, and the case is opened by causing the holder to hinge open.
- the case includes a sensor to detect when the vaporiser has been withdrawn from the case.
- if the lifting mechanism is activated, then a signal is sent to the vaporiser to turn the vaporiser on or otherwise alter its state.
- the case is part of an electronic vaporiser system, such as an e-cigarette system.
- the case is part of a medicinally approved nicotine drug delivery system.
- the case includes a holder for an electronic vaporiser is the same approximate size as a cigarette the electronic vaporiser is the same approximate size as a cigarette and includes no control buttons that could impede smooth ejection from the case.

the electronic vaporiser has a square or rectangular cross-section with rounded corners and includes a long PCB inserted lengthwise into the vaporiser the electronic vaporiser is filled from a user-replaceable e-liquid cartridge the electronic vaporiser is refillable with e-liquid only when inserted, whole and intact and not dis-assembled, into a re-fill case that includes a fluid transfer mechanism to transfer e-liquid into the vaporiser the electronic vaporiser is filled with e-liquid using a piezo-electric pump fluid transfer mechanism.

Case Feature 5:

A non-contact sensor detects PV release from the case: A non-contact sensor (e.g. a magnetic sensor, such as a reed switch, Hall effect sensor etc.) detects when the PV enters and leaves the charge/re-fill case by sensing the presence, proximity or movement of a small magnet or strip of metal in the PV (or some other mechanism for disrupting the local magnetic field around the sensor); a non-contact switch like a magnetic sensor has the advantage of being robust and reliable and does not affect the smooth, tactile quality of inserting and withdrawing the PV from the case, unlike physical (e.g. electrical) contacts. Similarly, a light sensor could be used; for example, a light sensor in the PV could detect when light was incident on the PV, inferring that the PV is now in an open case or no longer in the case at all; alternatively, the case could include a small light sensor facing a LED light source in the case; withdrawal of the PV triggers the light sensor since light from the LED is now incident on the sensor. Many variants of sensor are possible. When withdrawal of the PV is detected by the PV, it can automatically start heating the atomising coil so that the PV is at its optimal operational temperature when the user takes his first vape.

We can generalise this feature as follows:

An electronic cigarette vaporiser system that includes a case and a vaporiser that is stored in the case, and the system includes a non-contact sensor that detects release or withdrawal of the vaporiser from the case.

Other optional features:

when withdrawal of the vaporiser is detected, then the vaporiser electronic circuitry changes state.

changes state to a ready mode changes state to a ready or pre-heating mode in which an inhalation detector is activated.

changes state to a heating mode, in which the atomising unit is at least partly activated—so that the vaporiser is fully heated when the first inhalation is taken.

when withdrawal of the vaporiser from the case is detected by the vaporiser or the vaporiser receives data indicating that the vaporiser has been withdrawn from the case, it automatically starts heating the atomising unit so that the vaporiser is at its optimal operational temperature when the user takes his first vape.

the case includes some or all of the non-contact sensor the vaporiser includes some or all of the non-contact sensor the sensor is a non-contact magnetic sensor, such as a reed switch, or Hall effect sensor that detects when the PV enters and leaves a charge/re-fill case by sensing the presence, proximity or movement of a small magnet or strip of metal in the PV or some other mechanism for disrupting the local magnetic field around the sensor.

a light sensor in the PV detects when light is incident on the PV, inferring that the PV is now in an open case or no longer in the case at all;

the case includes a small LED light source and sensor; the LED is illuminated when the vaporiser is in the case and light reflected from the vaporiser is detected by the sensor; withdrawal of the vaporiser triggers the light sensor since light is no longer reflected off the vaporiser into the sensor.

Sensor is an IMU in the PV the case is a re-fill and re-charge case.

the electronic vaporiser system is an e-cigarette system.

the electronic vaporiser is a medicinally approved nicotine drug delivery system.

the case includes a holder for an electronic vaporiser is the same approximate size as a cigarette the electronic vaporiser is the same approximate size as a cigarette and includes no control buttons that could impede smooth ejection from the case.

the electronic vaporiser has a square or rectangular cross-section with rounded corners and includes a long PCB inserted lengthwise into the vaporiser the electronic vaporiser is filled from a user-replaceable e-liquid cartridge the electronic vaporiser is refillable with e-liquid only when inserted, whole and intact and not dis-assembled, into a re-fill case that includes a fluid transfer mechanism to transfer e-liquid into the vaporiser the electronic vaporiser is filled with e-liquid using a piezo-electric pump fluid transfer mechanism.

Case Feature 6: Sensor in the Piezo Pump Feed Line

The e-liquid feed or inlet tube includes a sensor that can detect whether the feed into the piezo micro-pump is liquid or air; this is very useful to know because the piezo-pump operates in different modes depending on the viscosity of the material being pumped. So being able to automatically alter the cycle time or frequency of the piezo-pump, based on an automatic assessment of the substance being pumped, is very useful.

We can generalise this feature as follows:

An electronic cigarette vaporiser system including a piezo-electric pump that pumps e-liquid into an electronic vaporizer, in which a sensor detects whether air or e-liquid is present in the liquid feed line into the piezo-electric pump and adjusts an operating parameter of the pump accordingly.

Other optional features:

the operating parameter that is adjusted is the frequency of the actuators in the piezo-pump the operating parameter that is adjusted is the flow-rate provide by the piezo-pump the operating parameter that is adjusted is the pressure delivered by the piezo-pump if the sensor detects that air is entering the piezo pump, then the piezo pump is controlled to operate at a high frequency, such as between 150-400 Hz (and preferably 300 Hz).

if the sensor detects that e-liquid is entering the piezo-pump, then the piezo pump is controlled to operate at a lower frequency, such as 7-20 Hz (and preferably 15 Hz).

a temperature measurement device provides a further input that is used to adjust one or more of the operating parameters of the piezo-pump ambient and/or e-liquid temperature is measured by the temperature measurement device as the temperature measured by the temperature measurement device gets lower, then the piezo pump is operated at a lower frequency.

A viscosity measurement device provides a further input that is used to adjust one or more of the operating parameters of the piezo-pump As viscosity increases, then the piezo pump is operated at a lower frequency The sensor includes a pair of electrical contacts on either side of the tube; and when there is e-liquid in the portion of the tube around which the sensors are placed, then there is a large resistance; when there is air in that portion, then the resistance is infinite or too high to measure.

The sensor is a capacitive sensor.

The sensor is an infra-red light sensor.

The piezo-pump and sensor are in the case

The piezo-pump and sensor are in the vaporiser

The piezo-pump and sensor are in a user-replaceable cartridge the electronic vaporiser is filled from a user-replaceable e-liquid cartridge the electronic vaporiser is refillable with e-liquid only when inserted, whole and intact and not dis-assembled, into a re-fill case that includes a fluid transfer mechanism to transfer e-liquid into the vaporiser Case Feature 7: Correcting any Imbalance in the Twin Actuators in the Piezo Pump Where the piezo pump has twin-piezo actuators, then one problem that can arise is that each actuator, over time, starts to operate slightly differently. Proper operation of the pump requires both actuators to operate identically, delivering exactly the same quantity of liquid for each pumping stroke. Pumping performance can drop significantly over time because of this mis-match in operation and output. In our system, a microcontroller can independently adjust the phase or timing or power of each voltage pulse that triggers a piezo-actuator until both actuators are operating together in the most optimal manner.

We can generalise this feature as follows:

An electronic cigarette vaporiser system including a piezo-electric pump with multiple piezo-actuators, in which a microcontroller independently adjusts the phase or timing or power of each voltage pulse that triggers a piezo-actuator.

Other optional features:

the microcontroller continuously or regularly monitors the efficiency or performance of the entire pump and adjusts the phase, timing, or power delivered to each piezo-actuator relationship until or so that the optimum pumping performance is achieved.

Pumping performance is measured using a flow sensor, such as a MEMS based flow sensor if one actuator is delivering less e-liquid than the other, then the power delivered to that first actuator is increased, or the power delivered to the other actuator is decreased.

For the less effective actuator, then the peak voltage delivered to that actuator is increased, or the peak voltage delivered to the other actuator is decreased.

For the less effective actuator, then the start of the voltage pulse is brought forward for that actuator, or the start of the voltage pulse for the other actuator is delayed.

The microcontroller continuously or regularly adjusts the various parameters affecting each actuator's performance until optimal pumping from the entire piezo-pump is achieved.

the piezo-pump is in the case.

the piezo-pump is in the vaporiser.

the piezo-pump is in a user-replaceable cartridge.

the electronic vaporiser is refillable with e-liquid only when inserted, whole and intact and not dis-assembled, into a re-fill case that includes the piezo-pump fluid transfer mechanism to transfer e-liquid into the vaporiser.

Another aspect is a piezo-electric pump with multiple piezo-actuators, in which a microcontroller independently adjusts the phase or timing or power of each voltage pulse that triggers a piezo-actuator in the piezo-pump. A microcontroller continuously or regularly monitors the efficiency or performance of the entire pump and adjusts the phase, timing, or power delivered to each piezo-actuator relationship until or so that the optimum pumping performance is achieved.

Cartridge Features 1-4

Cartridge Feature 1:

The cartridge or other form or parent reservoir includes an air pressure valve. As the fluid level inside the cartridge/reservoir falls (e.g. because fluid is being transferred into the child reservoir in the PV), atmospheric pressure forces open the air pressure valve to allow air to flow in and ensure equalisation of the air pressure. Air pressure equalisation or normalisation is also important whenever the ambient air pressure alters (e.g. when in an aircraft) or the temperature changes, causing the e-liquid in the cartridge to expand or contract, since it prevents the e-fluid leakage that might otherwise occur. If no air pressure valve is provided, then, as the cartridge empties, a partial vacuum forms, retarding fluid transfer out of the cartridge.

The valve also prevents contaminants from entering the cartridge/reservoir, which hence preserves the condition and stability of the e-liquid.

The cartridge is non-refillable, tamper evident and with an airtight seal to preserve e-liquid stability during transit and storage. The cartridge lid includes a small air hole to allow air to enter and leave a plenum chamber formed by the lid as one face, and ridges in the lid as the sides and a PTFE sheet facing the lid as the opposite face. The PTFE sheet is impermeable to e-liquid but permeable to air, hence enabling the air pressure equalization within the cartridge. The plenum provides for a large surface area for the air/PTFE interface. The PTFE membrane is typically constructed from PTFE Powder that is sintered and formed into a bulk microporous structure. The membrane is in the form of a rectangle approximately 50 mm×10 mm, and 0.25 mm thick, giving a large surface area. This is ultrasonically fused with the lid moulding window aperture of a similar size. The cartridge material is HDPE, which can be effectively ultrasonically welded to PTFE. Other materials than PTFE may be used if they have the right properties of being impermeable to e-liquid, but permeable to air; for example, PTFE coated paper may be suitable.

Instead of a PTFE sheet, a simple mechanical, e.g. a duckbill valve, could be used instead.

We can generalise this feature as follows:

An e-liquid cartridge or other form of parent reservoir designed to supply e-liquid to an electronic cigarette vaporiser, in which the cartridge includes an air pressure valve.

Other optional features:

the air pressure valve is designed so that as the fluid level inside the cartridge/reservoir falls (e.g. because fluid is being transferred into the child reservoir in the PV), atmospheric pressure enables the air pressure valve to allow air to flow in and ensure equalisation of the air pressure.

the cartridge, in use, engages with a fluid transfer mechanism that extracts e-liquid from the cartridge valve is air-permeable but impermeable to e-liquid.
valve is an oleophobic material
valve is a hydrophobic or super-hydrophobic material
valve is an air-porous, e-liquid impermeable layer or membrane that permits air pressure equalisation within the cartridge.
valve is an air-porous e-liquid impermeable PTFE layer or membrane.
valve is an air-porous e-liquid impermeable PTFE-coated paper layer or membrane.
PTFE layer or membrane includes on its air-facing side strands of polypropylene or another plastic that increases the surface area of the air-interface and/or facilitates welding to the body of the cartridge
the valve is a mechanical valve, such as a duckbill valve.
the cartridge is non-refillable, tamper evident and with an airtight seal to preserve e-liquid stability during storage and transportation.
the cartridge has a lid and that lid includes a small air hole to allow air to enter and leave a plenum chamber formed by (i) the lid as one face of the plenum, and (s) internal ridges in the lid as the sides of the plenum and an air-porous, e-liquid impermeable sheet facing the lid as the opposite face of the plenum, the sheet being in contact with the e-liquid in the cartridge.
the sheet is ultrasonically fused with the lid moulding window aperture of a similar size.
the Cartridge material is HDPE, PETG or COC, ultrasonically welded to PTFE.
the cartridge is not pressurized to a degree sufficient to expel e-liquid.
the cartridge is filled with an inert gas at manufacture.
the cartridge is adapted to be inserted into or attached to a portable, personal storage and carrying case for the electronic vaporiser and further adapted to engage with a fluid transfer system in the case.
the cartridge is adapted to be inserted into or attached to the electronic vaporiser and further adapted to engage with a fluid transfer system in the vaporiser.
the cartridge includes an integral fluid transfer mechanism
the cartridge is no greater than 10 mL in capacity.

We can also generalise beyond an e-liquid cartridge, to a cartridge with any sort of liquid: A cartridge or other form of parent reservoir designed to supply liquid to an electronic vaporiser, in which the cartridge includes an air pressure valve. This cartridge may include each of the features defined above.

Cartridge Feature 2: Cartridge with Chip

Most electronic vaporiser e-cigarettes allow users to refill liquid tanks with anything, which results in potentially high toxicity, coil contamination and device malfunctioning. No such manual refilling is possible with the closed cartridge in this system. To verify compliance and indicate any tampering, each cartridge has its own unique serial number written in a One-Wire flash memory chip (we use the term 'chip' to refer to a solid state memory, microcontroller or microprocessor). The chip is a Maxim DS28E15 security chip or authenticator. After a cartridge is installed, the case reads the cartridge's serial number and verifies whether its hash-function is valid. If the verification is okay, the cartridge will be used to refill the e-cig. If not, the case will block any liquid usage from this cartridge. The memory chip is the same sort type of chip used on ink-jet cartridges and its operation is the same.

The cartridge internal memory stores the liquid level too. For example, the case measures or infers the quantity of e-liquid pumped from the cartridge and stores a record of the estimated e-liquid left in the cartridge (it assumes the cartridge started with 10 mL of e-liquid). The case writes this value into the cartridge. If the cartridge is removed but not entirely used it will keep its last liquid level in memory. The case also stores this liquid level. When the cartridge is installed back into the case, then the case will read and use this number. A cartridge can be transferred to a different case and that new case will read out the correct liquid level for that cartridge and write the new level after some use back into the cartridge.

Reading and storing serial numbers also allows the case to gather usage statistics and send it over the Internet to the factory database (see above).

Each cartridge has information about when and where it was produced, and any tax due and when it was paid. Using this information and current time and data from the user's smartphone we can detect if liquid in the cartridge is out-of-date or a counterfeit.

We can generalise this feature as follows An e-liquid cartridge designed to provide e-liquid for an electronic cigarette vaporiser system, the cartridge including a chip that stores and outputs a unique identity for the cartridge and/or data defining the e-liquid stored in the cartridge, and the cartridge being adapted to be inserted into or form an integral part of the electronic vaporiser system.

Other optional features:
the cartridge, in use, engages with a fluid transfer mechanism that extracts e-liquid from the cartridge
the cartridge includes an integral fluid transfer mechanism
data stored and output by the chip defines one or more of: flavor, nicotine strength, manufacturing batch number, date of manufacture or filling, tax data, quantity of e-liquid stored in the cartridge.
the electronic vaporiser system includes a storage case adapted to both re-fill an electronic vaporiser with e-liquid from the cartridge and also re-charge a battery in the electronic vaporiser PV; and the chip outputs the unique ID and/or the data defining the e-liquid stored in the cartridge to a microcontroller or microprocessor in the case.
the cartridge is adapted to be inserted into or attached to a portable, personal storage and carrying case for an electronic vaporiser and further adapted to engage with a fluid transfer system in the case; and the chip outputs the unique ID and/or the data defining the e-liquid stored in the cartridge to a microcontroller or microprocessor in the case and the unique ID and/or data controls the operation of the fluid transfer system.
the cartridge is adapted to be inserted into or attached to an electronic vaporiser and further adapted to engage with a fluid transfer system in the vaporiser; and the chip outputs the unique ID and/or the data defining the e-liquid stored in the cartridge to a microcontroller or microprocessor in the case and the unique ID and/or data controls the operation of the fluid transfer system.
cartridge includes an integral fluid transfer mechanism
electronic vaporiser system is an e-cigarette PV.
electronic vaporiser system is a medicinally approved nicotine drug delivery system.
the cartridge is non-refillable, tamper evident and with an airtight seal to preserve e-liquid stability during storage and transportation.
cartridge includes a data transfer contact or contacts, such as contacts using a single wire protocol.
cartridge is no larger than 10 mL in capacity.
cartridge includes two apertures, the first aperture being used to fill the cartridge on a filing line and then being covered with a bung or plug and the second aperture being sealed by a septum designed to be penetrated or punctured by a needle or stem that withdraws e-liquid from the cartridge.

single wire connection is used to read data from the chip.

unique identity the data defining the e-liquid stored in the cartridge is processed by a processor in a device into which the cartridge is inserted or attached (e.g. the case into which the cartridge is inserted or attached or the vaporiser).

processor in the device receives data from a remote server either permitting the cartridge to be used by the case or preventing it from being used by the device.

processor calculates or determines if the unique identity is valid and sends a signal either permitting a fluid transfer mechanism to work with that cartridge or preventing it from working with that cartridge.

processor in the device writes data back to the chip.

data written back to the chip includes an estimate or measure of the quantity of e-liquid remaining in, or provided by, the cartridge.

The estimate or measure is calculated from data from or associated with the pump, such as the number of pumping cycles The estimate or measure is calculated using the ambient temperature and/or the e-liquid temperature processor in the device stores the quantity of e-liquid remaining in, or provided by, each cartridge, as defined by the unique identity for the cartridge.

processor in the device reads out from the chip the quantity of e-liquid remaining in, or provided by, the cartridge and compares that with its stored data for the quantity of e-liquid remaining in, or provided by, that cartridge and prevents use of that cartridge if the quantity of e-liquid remaining in, or provided by, the cartridge, as declared by the chip, exceeds the stored data for that cartridge, to make unauthorized re-filling of the cartridge pointless.

the cartridge is not pressurized to a degree sufficient to expel e-liquid.

the cartridge is filled with an inert gas at manufacture

We can generalise beyond an e-liquid cartridge to a liquid cartridge: An cartridge designed to provide liquid for an electronic vaporiser system, the cartridge including a chip that stores and outputs (i) a unique identity for the cartridge and (ii) data defining the liquid stored in the cartridge, and the cartridge being adapted to be inserted into or form an integral part of the electronic vaporiser system.

Cartridge Feature 3: Cartridge with Two Apertures

Filling of an e-liquid cartridge or cartomiser on an automated or semi-automated line conventionally requires a fine needle to puncture a rubber seal to that cartridge or cartomiser; when the needle is withdrawn, the rubber seal closes itself. This filling process needs to be done carefully, and this adds to the cost of the process. Filling large numbers of cartridges needs however to be done very cost-effectively and rapidly. In our system, we remove the need for a needle to puncture a seal during the filing stage; instead the cartridge is designed to have two apertures: one aperture is used for filing with a filing tube—there is no puncturing of a rubber seal. The other does have a rubber seal which is punctured, but only when the cartridge is inserted into the re-fill case. This approach reconciles the need for low-cost, high speed filing with e-liquid on automated or semi-automated manufacturing lines with minimal adaptation with the need for reliable storage of the e-liquid in the cartridge and reliable delivery of the e-liquid from the cartridge when inserted into the re-fill case.

We can generalise this feature as follows:

An e-liquid cartridge designed to provide e-liquid for an electronic cigarette vaporiser, the cartridge including:

two apertures, the first aperture being used to fill the cartridge on a filing line and then being covered with a bung or plug or other form of seal and the second aperture being sealed by a septum or other form of seal that is designed to be penetrated or punctured by a needle or stem that, in use, withdraws e-liquid from the cartridge.

Optional features:

a strip covers one or both apertures.

the strip is adhesive and tamper evident the strip is pealed off by a user prior to use alternatively, the strip does not need to be pealed off by a user prior to use because it includes gap over the second aperture that is large enough so that a filling needle or stem can pass through that gap to extract e-liquid from the cartridge, but is small enough to show any tampering to the septum or other seal to the second aperture.

the apertures are in one face of the cartridge.

the cartridge is purged with an inert gas prior to filling with e-liquid the first aperture is sized to enable rapid filling with e-liquid on an automated or semi-automated manufacturing line the cartridge is not pressurized to a degree sufficient to expel e-liquid.

the cartridge, in use, engages with a fluid transfer mechanism that extracts e-liquid from the cartridge via the needle or stem that penetrates the septum or seal covering the second aperture in the cartridge.

the cartridge is adapted to be inserted into or attached to a portable, personal storage and carrying case for an electronic vaporiser and further adapted to engage with a fluid transfer system in the case.

the cartridge is adapted to be inserted into or attached to an electronic vaporiser and further adapted to engage with a fluid transfer system in the vaporiser.

the cartridge includes an integral fluid transfer mechanism the cartridge is no greater than 10 mL in capacity.

We can generalise beyond an e-liquid cartridge to a cartridge with any sort of liquid: A cartridge designed to provide liquid for a vaporiser, the cartridge including:

two apertures, the first aperture being used to fill the cartridge on a filing line and then being covered with a bung or plug or other form of seal and the second aperture being sealed by a septum or other form of seal designed to be penetrated or punctured by a needle or stem that, in use, withdraws liquid from the cartridge.

Cartridge Feature 4: The Cartridge Stores the Batch Number of the e-Liquid it is Filled with and can be Remotely Disabled from Using Specific Batch Numbers Product safety is vitally important in the e-cigarette and also medicines categories. Whilst every precaution is taken to ensure that all e-liquids pass all applicable toxicology and other safety standards, it remains possible that contaminants might inadvertently be introduced, or that research will reveal that an ingredient previously thought safe is in fact potentially harmful. Because our cartridges store on a secure chip data that identifies the specific batch number of e-liquid used, and a unique ID for that cartridge, and because they are designed to work with a connected vaporising system (i.e. one which can receive data from a remote server), we can remotely control, without any user input needed, the vaporizing system to not use any batch that is considered potentially harmful. For example, if a batch is identified as potentially harmful, then we can send a signal from a server that is received by the app running on a user's smartphone, which in turn is used to send a message to the case with the affected batch number or unique IDs. The case can then store that batch number and/or unique IDs and then compare the batch number or unique IDs of every cartridge inserted into the case with that stored number; where there is a match, then the case can disable or prevent use of that affected cartridge and also write warning data onto the chip of that cartridge to prevent any further use. A warning message can then be displayed on the case and the user's smartphone alerting them that a different cartridge should be used instead.

The same approach can be applied to the date of manufacturing data held on the cartridge chip: for example, the microcontroller in the case can check whether the date of manufacture is within required tolerance—for example 6 months if the shelf life is 6 months and prevent use if the cartridge is older than 6 months.

We can generalise this feature as follows:

An electronic cigarette vaporiser system including a cartridge designed to provide a liquid or other substance for the electronic vaporiser system, the cartridge including a chip that stores data related to the batch number of the substance stored in the cartridge, and the cartridge being adapted to be inserted into or form an integral part of the electronic vaporiser system.

Optional features:
the electronic vaporiser system reads the data from the cartridge chip and compares that data with stored data and, depending on the result of that comparison, either prevents or permits use of that substance.
the electronic vaporiser system prevents use of that substance by preventing or not initiating use of a fluid transfer mechanism that would otherwise transfer some of that substance from the cartridge.
the electronic vaporiser system prevents use of that substance by sending a signal to the chip that sets a flag or other marker on the chip that, when read by the
the flag or marker disables or prevents the cartridge from discharging any of the substance from the cartridge
the electronic vaporiser system receives a wireless signal that controls the disablement of a specific cartridge.
the electronic vaporiser system receives a wireless signal that includes batch numbers that are defective or not to be used.
the wireless signal that controls the disablement of a specific cartridge, batch number or range of batch numbers is sent from a connected smartphone app or other personal device, which in turn receives a wireless control signal from a remote control centre.
the data related to the batch number of the substance stored in the cartridge is a number or other identifier that allows the specific substance in the cartridge to be tracked back to its manufacture.
the data related to the batch number of the substance stored in the cartridge is a batch manufacture number
the data related to the batch number of the substance stored in the cartridge is an ID, unique to that cartridge
the case or connected smartphone app or other personal device stores the data related to the batch number for the cartridge used or inserted into the electronic vaporiser system.
the cartridge is not pressurized to a degree sufficient to expel any substance.
the cartridge is filled with an inert gas at manufacture
the cartridge, in use, engages with a fluid transfer mechanism that extracts the substance from the cartridge
the substance is e-liquid.
the chip stores data related to the date of manufacture of the substance stored in the cartridge and the system reads the date data from the cartridge chip and either prevents or permits use of that substance depending on that date.
the cartridge is adapted to be inserted into or attached to a portable, personal storage and carrying case for an electronic vaporiser and further adapted to engage with a fluid transfer system in the case.
the cartridge is adapted to be inserted into or attached to an electronic vaporiser and further adapted to engage with a fluid transfer system in the vaporiser.
the cartridge includes an integral fluid transfer mechanism
cartridge is no larger than 10 mL in capacity.

We can further generalise the feature as a cartridge that forms part of the electronic vaporiser cigarette system as defined above.

PV Features 1-16

PV Feature 1:

PV includes an air pressure valve: the PV includes an air pressure valve or device so that excess air can escape from an e-liquid 'child' reservoir in the PV. The 'child' reservoir is the reservoir in the PV that is directly filled by a 'parent' reservoir; the 'parent' reservoir can be an e-liquid cartridge that is removable from the PV or case. This child reservoir is designed to enable an atomizing coil unit to draw in controlled amounts of e-liquid for vaping; e-liquid in the secondary child reservoir is typically wicked into the atomising coil unit.

So, to re-cap, the parent reservoir, typically a user-removable and replaceable, sealed or closed e-liquid capsule or cartridge, perhaps of capacity 5 mL or 10 mL, is slotted into the PV or the re-fill/re-charge case, and a fluid transfer mechanism operates to transfer e-liquid from the capsule or cartridge into the 'child' reservoir in the PV, typically 2 mL or less (it is 0.2 mL in the illustrated implementation). The heating coil unit is arranged to gradually wick or otherwise transfer some of the e-liquid up from the child reservoir in normal vaping operation.

Air needs to escape from the child reservoir in the PV when that reservoir is being filled under pressure with e-liquid, otherwise excessively high pressures can build up in the e-liquid in the child reservoir, which can lead to leakage as the e-liquid finds a way to escape via the atomising coil unit and hence out through the vapour inhalation apertures that are connected to the coil unit. Also, air needs to enter into the child reservoir as e-liquid is consumed in normal use, since otherwise a partial vacuum would be created, which would tend to prevent or retard e-liquid in the child reservoir wicking/entering the atomising coil unit.

Also, if the ambient air pressure changes, for example in an aircraft where the ambient pressure can rapidly fall to significantly lower than sea-level atmospheric pressure, then the valve will operate to ensure that the air pressure in the reservoir can rapidly and reliably equalise to ambient air pressure in the aircraft cabin, again preventing leakages of e-liquid from the PV.

Hence, the PV includes a valve that, for example, equalises the air pressure in the PV to ambient air pressure, or alters it to bring it closer to ambient air pressure ('normalising') in order to prevent leakage when filling the PV with e-liquid and to ensure correct operation whilst the PV is consuming e-liquid.

The air-pressure valve or device could have no moving parts, but instead be a barrier made of an air-porous material, such as a sintered polymer or metal, coated with or otherwise including a barrier or layer of an air-porous substance that is not porous to e-liquid, such as an oleophobic material or a hydrophobic or super-hydrophobic material, for example, PTFE or a suitable porous ceramic. The air-pressure valve or device could be positioned to allow air to flow out from the 'child' reservoir. Equally, it will allow air to flow into the child reservoir as e-liquid is consumed and also as ambient pressure rises (e.g. as an aircraft descends from high altitude). Examples of suitable oleophobic materials are sintered phosphor bronze, sintered stainless steel and sintered PU plastic.

Where the vaporizer uses a conventional cotton wick and coil, then the air valve is separate from the wick. However, where a ceramic coil is used (typically a hollow ceramic wicking cylinder with an embedded heating coil wound within the hollow core), then the ceramic material itself acts as the air valve since the ceramic itself is air-permeable.

We can generalise this feature as follows:

An electronic cigarette vaporiser that includes an air pressure valve or device to enable excess air to escape from an e-liquid reservoir in the vaporiser during pressurized filling of the vaporiser with e-liquid.

Other optional features:
- the reservoir is a child reservoir and is filled by a parent reservoir, the parent reservoir being a cartridge that is removable from the vaporiser or a case that stores, re-fills and re-charges the vaporiser.
- the child reservoir supplies e-liquid designed to enable an atomizing unit to draw in controlled amounts of e-liquid for vaping.
- the parent reservoir is a user-removable and replaceable, sealed or closed e-liquid capsule or cartridge, of capacity 10 mL or less, and is slotted into or otherwise used by the PV or a portable re-fill/re-charge case for the PV, and a fluid transfer mechanism operates to transfer e-liquid from the capsule or cartridge into the child reservoir in the PV, of capacity 3 mL or less.
- vaporizer includes a ceramic cell (i.e. a ceramic atomizing unit) and the air pressure device is the wall of the ceramic cell.
- The ceramic cell includes a cylindrical wicking cylinder with a cylindrical bore and with an embedded heating coil wound within the bore.
- reservoir is a chamber arranged outside of the external wall of the ceramic cell
- the child reservoir includes (i) one or more small channels and (ii) a second child reservoir fed by the small channel(s) which surrounds the atomising unit and from which e-liquid is drawn (e.g. by a wick or other porous member) into the atomising unit (e.g. a heating coil inside an air chamber).
- the valve or device permits air to enter into the child reservoir in the vaporiser as liquid is consumed in normal use by the vaporiser.
- the valve or device permits air to enter into the child reservoir if the ambient air pressure changes, for example in an aircraft.
- the valve or device is a barrier made of an air-porous material, such as a sintered polymer or metal, coated with or otherwise including a barrier or layer of an air-porous substance that is not porous to e-liquid.
- the barrier or layer of the air-porous substance that is not porous to e-liquid is an oleophobic material or a hydrophobic or super-hydrophobic material.
- the valve or device in which the oleophobic material is one of: sintered phosphor bronze, sintered stainless steel and sintered PU plastic.
- the air-porous substance is a PTFE membrane.
- the PTFE membrane is compressively secured into an aperture that is connected to an air passage that leads to the child reservoir.
- the valve or device is made of a porous ceramic material.
- the electronic vaporiser is the same approximate size as a cigarette
- the electronic vaporiser is the same approximate size as a cigarette and includes no control buttons
- vaporiser is automatically activated when it detects that it has been withdrawn from a case that otherwise stores the vaporiser.
- the electronic vaporiser has a square or rectangular cross-section with rounded corners and includes a long PCB inserted lengthwise into the vaporiser
- the electronic vaporiser has a squircle cross-section
- the electronic vaporiser is only re-fillable from a user-replaceable closed, e-liquid cartridge
- the electronic vaporiser is refillable with e-liquid only when inserted, whole and intact and not dis-assembled, into a re-fill case that includes a fluid transfer mechanism to transfer e-liquid under pressure into the vaporiser from a user-replaceable closed, e-liquid cartridge
- the electronic vaporiser is filled with e-liquid using a piezo-electric pump PV Feature 2:

PV includes a mechanical valve that is pushed up from its seat when filling takes place: The PV includes a mechanical valve that opens when the PV is being filled—for example, a nozzle or stem from the re-fill case or cartridge is inserted into an e-liquid filling aperture in the PV (or as the PV is inserted into the re-fill case or cartridge) for filling the PV with e-liquid. This causes the valve, situated just behind the e-filling aperture, to be pushed open or rise up from its seat, moving against the bias force of a small spring, so that e-liquid can freely flow through the nozzle or stem into a child reservoir in the PV.

When the nozzle or stem is withdrawn (e.g. the PV is withdrawn from the re-fill case or the filling cartridge or capsule withdrawn from its filling position in the PV where that capsule fits directly into the PV and there is no separate re-fill and re-charge case) then the valve automatically closes by resting back on its seat.

Hence, when the PV is not being actively filled with e-liquid, for example, it is being held for vaping, or is stored in a bag, the valve is fully closed and this prevents any e-liquid in the 'child reservoir' in the PV from leaking out into the user's mouth. The child reservoir here includes a feed pipe that leads into a second child reservoir which surrounds the atomising unit and from which e-liquid is drawn (e.g. by a wick or other porous member) into the atomising chamber (e.g. a heating coil inside an air chamber).

Once the PV is withdrawn from the case, or the stem from the filling 'parent' reservoir is withdrawn from the PV, then the valve sits back down under the biasing force of a small spring and the valve then re-seals against its seat, preventing leakage of any e-fluid out from the child reservoir in the PV. Ensuring that there is no leakage from the e-liquid filling process is especially important if the filling nozzle or aperture in the PV is at the same end as the inhalation nozzles, but this solution applies irrespective of where the filling nozzle or aperture is located.

The stem or nozzle that protrudes from the removable cartridge or other form of parent reservoir, or is connected to the cartridge via a micro-pump, engages with the valve in the PV to push it off its seat and also passes through a duckbill valve or a series of two or more duckbill valves; when the stem or nozzle is withdrawn then the duckbill wipes any droplets of e-juice from the stem, ensuring that those droplets are not deposited on any surface from where they could be ingested by the user or leak out from the PV, but are instead retained in a cavity in the PV behind the duckbill valve.

We can generalise this feature as follows: A electronic cigarette vaporiser that includes a mechanical valve that is (i) pushed up from its seat to enable automatic filling of the vaporiser with e-liquid from a fluid transfer mechanism and (ii) returns to seal against its seat at other times when the vaporiser is being vaped or inhaled from (e.g. when filling is complete).

Other optional features:
- a nozzle or stem from an e-liquid filling device, such as a re-fill case or removable cartridge, is inserted into the PV for filling the PV with e-liquid and this causes the valve to be pushed open or rise up from its seat, moving against the bias force of a small coil spring or other biasing device, so that e-liquid can freely flow from the e-liquid filling device through the nozzle or stem into a child reservoir in the PV.
- the e-liquid filling device is a re-fill case or removable e-liquid cartridge.
- when the nozzle or stem is withdrawn then the valve automatically closes by resting back on its seat.
- a child reservoir in the PV is filled when the valve is open and a fluid transfer mechanism pumps e-liquid into the PV.
- the child reservoir includes a feed pipe that leads into a second child reservoir which surrounds an atomising unit and from which e-liquid is drawn (e.g. by a wick or other porous member, such as a ceramic cell) into the atomising unit (e.g. a heating element inside an air chamber).
- the stem or nozzle in the re-fill case or cartridge and that engages with the valve in the PV to push it off its seat, passes through a duckbill valve or a series of two or more duckbill valves; when the PV is withdrawn away from the stem or nozzle then the duckbill wipes any droplets of e-liquid from the stem or nozzle, ensuring that those droplets are not deposited on any surface from where they could be ingested by the user, but are instead retained in a cavity in the PV behind the duckbill valve.
- the stem or nozzle in the re-fill case or cartridge etc. and that engages with the valve in the PV to push it off its seat includes a stop valve to shut off any e-liquid when the vaporiser is withdrawn from the stem or nozzle.
- the electronic vaporiser is the same approximate size as a cigarette
- the electronic vaporiser is the same approximate size as a cigarette and includes no control buttons
- the electronic vaporiser is automatically activated when it detects that it has been withdrawn from a case that stores the vaporiser.
- the electronic vaporiser has a square or rectangular cross-section with rounded corners and includes a long PCB inserted lengthwise into the vaporiser
- the electronic vaporiser has a squircle cross-section
- the electronic vaporiser is only re-fillable from a user-replaceable closed, e-liquid cartridge
- the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge
- the electronic vaporiser is filled with e-liquid using a piezo-electric pump fluid transfer mechanism PV Feature 3:

PV or case has an IMU: The PV includes an IMU (inertial measurement unit) to detect when it is being lifted up and out of the case so it can start heating (e.g. activate the atomising coil); it can also tell if it is left on a table and so can power down. Movement-related data can be stored and uploaded to a server (for example, sent over Bluetooth to the user's connected smartphone, which in turn sends it to the server). Movement data can be combined with data from the pressure activated sensor or switch that detects an inhalation. This data can be useful since it shows how the PV is being used, the duration of a vaping session etc. Fully instrumenting the vaporiser in this way, including tracking the time of day of all events, generates data that could be very powerful for scientists and regulators seeking to better understand how these products are being used, as well as to enable designers to improve the system.

The case also senses its movements using an IMU or accelerometer; the case and the e-cig PV also have capacitive sensors to check if one or both of them are actually in the user's hand. This allows the case to safely update the PV firmware by detecting that it is not in the user's hand and laying still, therefore the PV is not going to be removed which may corrupt the firmware. This also allows the case to stop any refilling process if it is upside down.

Also, based on the information gathered from device sensors we can calculate users' activity patterns and use it in different use-cases, such as firmware updates, or indicating battery and liquid levels with LEDs on the front device panel.

We can generalise this feature as follows:

An electronic cigarette vaporiser that includes an IMU (inertial measurement unit).

Other optional features:
- the IMU enables the vaporiser to detect when it is being lifted up and out of a case in which it has been stored so that it can change state.
- the change of state is to turn on.
- the change of state also includes to start heating an atomising element.
- the data from the IMU enables the vaporiser to tell if it is not being used (e.g. has just been left on a table) and so can power down.
- movement data from the IMU is combined with data from a pressure activated sensor or switch in the vaporiser that detects an inhalation.
- the time of day of all events, including movement events, is recorded.
- data collected by the vaporiser is sent from the vaporiser for external storage.
- the external storage is a memory in a case in which the vaporiser is stored.
- the electronic vaporiser includes data transfer contact(s) that engage with data transfer contact(s) in the case.
- the electronic vaporiser system is an e-cigarette system.
- the electronic vaporiser is a medicinally approved nicotine drug delivery system.
- the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism Another feature is an electronic vaporiser case that includes an IMU (inertial measurement unit) to detect when it is being handled.

PV Feature 4:

The PV includes a touch sensor: The PV and/or the case can sense when you are touching it—e.g. with a capacitive sensor. It can be programmed to detect specific touch inputs and control the PV accordingly. For example, the touch inputs are not merely to either activate or de-activate the PV, but more sophisticated actions as well. For example, tap twice on the body of the PV to bring it up to heat; tap three times to put it to sleep. Or the PV could detect when it is held by at least two fingers, and then automatically turn on and start heating. The sensor could detect a touch control input anywhere on the PV, or at a specific region. Using a capacitive sensor removes the need for a discrete button. A touch input detected on the case can turn the display panel on the case on. Specific touch inputs can activate pre-heating of the PV stored in the case, or can (where the case does not include the manually hinged holder but some other design to enable the PV to withdraw or be withdrawn from the case) cause the PV to extend from the case or to be otherwise revealed or made accessible. All touch data can be stored and uploaded to a server (for example, sent over Bluetooth to user's the connected smartphone, which in turn sends it to the server). This data can be useful since it shows how the PV is being used, the duration of a vaping session etc. Using a touch sensor instead of physical push buttons enables the PV and/or case to be sleek and simple, not dissimilar to a conventional cigarette and its pack.

We can generalise this feature as follows:

An electronic cigarette vaporiser system that includes a touch sensor and is programmed to detect specific multiple different kinds of touch inputs and to control the PV accordingly, and the touch sensor is included on a vaporiser and/or a case for the vaporiser.

Other optional features:

the touch inputs include one or more of the following: activate or de-activate the vaporiser; turn on or off lights on the vaporiser (these can indicate the amount of e-liquid consumed); dim the lights on the vaporiser; alter the colours of the lights on the vaporiser; alter the power delivered to the heating element.

the touch inputs include tapping a defined one or more times; moving a finger or fingers along a surface of the vaporiser or the case in defined pattern or gesture.

the PV detects when it is held by at least two fingers, and then automatically turns on the main circuitry (i.e. the circuitry other than that needed for touch sensing) and may also starts heating.

all touch inputs to the vaporiser generate touch data that is stored in the vaporiser and then sent for external storage the external storage is a memory in a case in which the vaporiser is stored.

the electronic vaporiser includes data transfer contact(s) that engage with data transfer contact(s) in the case the touch data is sent over short range wireless (e.g. Bluetooth) to the user's connected smartphone, which in turn sends it to the server.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no push-type control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism if the case detects that it is touched, then it can activate a display panel on the case PV Feature 5: 'z' Wick Coil Designing a specific shape of wick and coil that is both effective and also fast to manufacture is not straightforward. One design uses a 'z' shaped wick.

We can generalise this feature as follows:

A wick and coil assembly for a PV electronic cigarette vaporiser, in which the wick has a body around which is arranged a heating element, and in which:

(a) the body is arranged longitudinally along the long axis of the PV electronic vaporiser in a vapourising chamber to interrupt the air flow path through that chamber;

(b) one end of the wick includes an end section, angled with respect to the body, and protruding into an e-liquid reservoir;

(c) the other end of the wick includes an end section, angled with respect to the body, and protruding into an e-liquid reservoir.

Other optional features:

one or both end sections of the wick are perpendicular to the body of the wick.

each end sections points in a different direction.

each end section points in the same direction.

a heating coil is wound around the body of the wick.

the assembly is positioned within a tube and the tube forms the inner surface of an e-liquid reservoir.

the e-liquid reservoir is fed by a user-replaceable cartridge.

the wick is cotton.

the wick is made of a porous ceramic.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 6:

PV with replaceable wick and coil: the atomizing unit may last less time than the other components in the vaporiser, especially if it uses a cotton wick. It is very useful to be able to replace the tip that includes the atomizing coil with a new atomizing tip.

We can generalise this feature as follows:

An electronic cigarette vaporiser that is not dis-assembled for filling with e-liquid, but is instead filled from a user-replaceable e-liquid cartridge;

and in which the vaporiser includes a front section comprising a wick and heating assembly but no e-liquid cartridge, the front section being removably fitted to a body of the vaporiser to enable a replacement front section to be used, for example once the original wick or heating element starts to degrade, that replacement front section being supplied to the end-user with no e-liquid in it.

Optional features include:

front section magnetically latches onto the body of the vaporiser.

front section press-fits onto the body of the vaporiser.

front section screws onto the body of the vaporiser.

wick includes cotton material wick includes ceramic material ceramic material is a ceramic cell, with a heating element inside the ceramic cell the front section includes an opening or channel or pipe that connects with or joins with an opening or channel or pipe in the body of the vaporiser and through which e-liquid passes.

degradation of the heating element is automatically detected by an electronics module that monitors electrical characteristics of the heating element and determines if those characteristics are associated with degradation of the heating element.

the electrical characteristics are the resistance of the heating element.

the electronics module generates a signal indicating that the front section should be changed if degradation of the heating element is detected.

a micro-pump operates to drain e-liquid from the wick and heating assembly if the front section is to be removed from the body of the vaporiser.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 7: Pulsed Power to the Coil Pulse Width Modulation of the coil current is used. PWM is generated by the MCU (microcontroller unit) in the PV and goes to the power switch that commutates current across the coil. On receiving a signal from the pressure sensor indicating inhalation, the MCU starts to generate PWM signals with a maximum duty cycle to heat the coil as fast as possible and then it will be decreased to maintain coil temperature in the working range according to pre-mapped temperature calculations stored in the MCU.

PWM changes from approximately 90% to 1-10% duty cycle for preheat and 0% when idle.

We can generalise this feature as follows:

An electronic cigarette vaporiser that includes a heating element, a power source and an electronics module that manages the delivery of power, current or voltage to the heating element, in which the electronics module controls or delivers pulses of power, current or voltage to the heating element.

Other optional features:

pulse is PWM.

pulses are delivered at high switching frequency.

high switching frequency is 1-10 KHz.

PWM changes from approximately 90% to 1-10% duty cycle for preheat and 0% when idle.

pulses extend the battery life of the vaporiser.

power current or voltage is controlled or shaped to minimize the production or release of potentially harmful substances.

pulses control the temperature of the heating element to minimize the production or release of potentially harmful substances by the vaporiser.

heating element temperature is estimated from the resistance of the heating element.

PWM control is used to implement discrete mode vaping (see Case Feature 2), i.e. to reduce the amount of vapour produced by the vaporiser compared to a normal mode.

PWM control is used to implement power mode vaping (see Case Feature 3), i.e. to increase the amount of vapour produced by the vaporiser compared to a normal mode, whilst monitoring the heating element temperature of the vaporiser to ensure that excessively high temperatures, associated with undesirable compounds in the vapour, are not reached.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 8: Detecting Coil Degradation If the coil resistance will be higher than some limit we can say that the coil needs to be replaced. Large fluctuations in coil resistance will be treated like a coil malfunction (an may be due to a bad contact for example).

We can generalise this feature as follows:

An electronic cigarette vaporiser that includes a heating element and further includes or co-operates with an electronics module that (i) detects characteristics of the delivery of power, current or voltage to the heating element and (ii) determines if those characteristics are associated with degradation of the heating element.

Other optional features:

a characteristic that is associated with degradation of the heating element is an increase in the heating element resistance the heating element resistance is established by the electronics module sending a test current through the heating element that is sufficient to enable a measurement of resistance to be made the test current is set at a level or a duration that the temperature of the heating element is not raised to a vaping temperature of for example 130 degrees C.

if the electronics module measures a very large resistance of the heating element, above a preset threshold, then that is indicative of a defective heating element the electronics module stores a record of the measured characteristics and determines if those stored records indicate fluctuations that are indicative of degradation of the heating element.

The electronics module generates a signal indicating that the heating element should be replaced.

The signal causes a visual indication to be given on the vaporiser and/or a case into which the vaporiser is stored and/or a device that is wirelessly connected to the case.

vaporiser includes the power source and the electronics module.

vaporiser is stored in a case that includes the power source and electronics module.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 9: Estimating Coil Temperature Since the system uses a microcontroller MCU to control the overall coil heating process, we can use its calculating capabilities to obtain the coil temperature by indirect methods using this MCU. Most of electronic vaporisers on the market have no control over the coil temperature. Problems arise, such as:

boiling of the e-liquid, with hot drops bursting out of the mouthpiece, coil overheating due to low liquid level, which leads to high-toxicity fumes In our system, the MCU measures or infers the coil temperature in the electronic vaporiser via the coil resistance control. It is a much more accurate method because there is no thermal resistance between the coil and the temperature sensor.

Our measurement technique relies on the linear approximation of the dependence of resistance on temperature in the range from 50 to 200° C. So the MCU directly measures current and voltage delivered to the coil; it calculates coil resistance from this data. We have empirically mapped resistance to temperature for various coil/atomizing combinations. For example, in our laboratory experiments we obtained the empirical equation for the coil resistance $R(T)=-1.714*T+1.68$ using a KangerTech 1.5 Ohm coil.

We can generalise this feature as follows:

An electronic cigarette vaporiser PV that includes a heating element and further includes or co-operates with an electronics module that (i) detects characteristics of the resistance of the heating element and (ii) uses an inference of temperature derived from that resistance as a control input.

Other optional features:

the temperature of the heating element is inferred from data stored in the electronics module that has been empirically obtained for a specific heating element design.

the electronics module controls the power delivered to the heating element to ensure that it is no higher than approximately 130° C., plus an error tolerance.

the electronics module controls the power delivered using the resistance measurement and does not calculate any derived temperature.

the electronics module applies multiple techniques designed to ensure the heating element is at its optimal heating temperature, including estimating heating element resistance, and weights the signals from each technique.

the electronic vaporiser system is an e-cigarette system.
the electronic vaporiser is a medicinally approved nicotine drug delivery system.
the electronic vaporiser is the same approximate size as a cigarette
the electronic vaporiser is the same approximate size as a cigarette and includes no control buttons
the electronic vaporiser is automatically activated when it detects that it has been withdrawn from a case that otherwise stores the vaporiser.
the electronic vaporiser has a square or rectangular cross-section with rounded corners and includes a long PCB inserted lengthwise into the vaporiser
the electronic vaporiser has a squircle cross-section
the electronic vaporiser is only re-fillable from a user-replaceable closed, e-liquid cartridge
the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge
the electronic vaporiser is connected to, and filled with, e-liquid using a piezo-electric pump fluid transfer mechanism PV Feature 10: Monitoring Each Inhalation to Measure e-Liquid Consumption and Heating Coil Degradation The electronics module also allows the PV to count each and every draw from the electronic vaporiser. The PV includes a conventional pressure sensor to determine when the user starts and stops inhalation. The MCU counts these start and stop events and measures the time between them. This 'draw' or 'inhalation' time will be used in calculating the e-liquid consumption.

The PV can also estimate when and if the coil needs to be cleaned or replaced with a new one since we can estimate the number of draws a coil should achieve. Also this vape or inhalation counting allows us to estimate the liquid level in the PV since each inhalation will use an amount of e-liquid we can approximate or guess; we can alter that approximation in light of feedback from other parts of the system, for example we know quite accurately how much e-liquid is delivered to the PV on its next filling cycle since the piezo pump delivers a precise amount of e-liquid for each pumping action and the MCU tracks the number of pumping actions needed to fill the PV each time. So we can use this information from the case to know how much e-liquid was injected to the PV.

We can generalise this feature as follows:

An electronic cigarette vaporiser that includes a heating element, an air pressure sensor and a microcontroller; in which the microcontroller stores, processes or determines the extent of each inhalation using signals from the air pressure sensor.

Other optional features:
the microcontroller calculates approximate e-liquid consumption from the extent of each inhalation or provides data that enables an external processor to calculate approximate e-liquid consumption.
the microcontroller calculates when and if the heating element needs to be cleaned or replaced based on the number and/or extent of the inhalations made, or provides data that enables an external processor to make this calculation.
the microcontroller calculates the approximate quantity of e-liquid left in the vaporiser based on the calculated approximate e-liquid consumption.
the microcontroller calculates approximate quantity of e-liquid left in the vaporiser based on the calculated approximate e-liquid consumption and also using data from other elements in the vaporiser or the case that re-fills the vaporiser.
the extent of an inhalation is a function of one or more of: duration; peak flow rate; average flow rate
the electronic vaporiser system is an e-cigarette system.
the electronic vaporiser is a medicinally approved nicotine drug delivery system.
the electronic vaporiser is the same approximate size as a cigarette
the electronic vaporiser is the same approximate size as a cigarette and includes no control buttons
the electronic vaporiser is automatically activated when it detects that it has been withdrawn from a case that otherwise stores the vaporiser.
the electronic vaporiser has a square or rectangular cross-section with rounded corners and includes a long PCB inserted lengthwise into the vaporiser
the electronic vaporiser has a squircle cross-section
the electronic vaporiser is only re-fillable from a user-replaceable closed, e-liquid cartridge
the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge
the electronic vaporiser is connected to, and filled with, e-liquid using a piezo-electric pump fluid transfer mechanism PV Feature 11: Monitoring the Coil Characteristics to Identity the Type of Coil.

It is useful to be able to identify automatically the type of coil (e.g. material of the heating wire, other characteristics) since different types of coil may have different optimal and also maximum safe temperatures, and may react differently to the pulsed power technique described above.

We can generalise this feature as follows:

An electronic cigarette vaporiser that includes a heating element and a microcontroller; in which the microcontroller monitors or measures electrical characteristics of the heating element and uses that to automatically identify the type of heating element and as a control input.

Other optional features:
the vaporiser is operable to use different types of heating element, with different electrical characteristics.
the vaporiser stores a record of different values or profiles of electrical characteristics and the type of heating element associated with each value or profile and can then compare any monitored or measured electrical characteristics with that record to determine the likely type of heating element that is present in the vaporiser.
the electrical characteristics are monitored or measured by passing a current through the element which is not sufficient to heat the heating element to its operating temperature.
the electrical characteristics include the resistance of the heating element.
the microcontroller automatically applies different heating parameter controls, including optimal and maximum operating temperature, depending on the type of heating element that is identified.
the electronic vaporiser system is an e-cigarette system.
the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 12: Monitoring External or Ambient Temperature to Ensure the Coil is at Optimal Operating Temperature Conventional electronic vaporisers can perform poorly in cold conditions (e.g. below 0° C.) because the coil works at below its optimal operating temperature. We include a temperature measuring sensor in the PV or case which measures ambient temperature and controls the power delivered to the coil to take into account the ambient temperature—e.g. increasing power when it is very cold.

We can generalise this feature as follows:

An electronic cigarette vaporiser that includes a heating element and a microcontroller; in which the microcontroller monitors or measures or uses data relating to external or ambient temperature and uses that as a control input.

Other optional features:

the control input automatically controls the power delivered to the heating element to ensure that the heating element operates at its optimal temperature.

where ambient temperatures are monitored or measured as very cold, then the power to the heating element is automatically increased to compensate.

where ambient temperatures are monitored or measured as very cold, then a pre-heat function is automatically operated prior to the first inhalation to bring the heating element to it's optimal temperature.

the vaporiser includes or co-operates with an electronics module that (i) detects characteristics of the resistance of the heating element and (ii) uses an inference of temperature derived from that resistance as a control input.

the temperature of the heating element is inferred from data stored in the electronics module that has been empirically obtained for a specific heating element design.

the microcontroller applies multiple techniques designed to ensure the heating element is at its optimal heating temperature, including estimating coil resistance, and weights the signals from each technique.

the electronics module controls the power delivered using the resistance measurement and does not calculate any derived temperature.

the electronics module controls the power delivered to the heating element to ensure that it is no higher than approximately 130° C., plus an error tolerance.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism the electronic vaporiser includes a temperature measuring sensor for measuring ambient temperature.

the electronic vaporiser receives data or a control signal from a temperature measuring sensor in a case for the vaporiser.

PV Feature 13: Monitoring Airflow to Ensure the Coil is at Optimal Operating Temperature Conventional electronic vaporisers include an air-pressure sensor that acts as a simple switch: when air passes over the sensor, the system assumes the user is inhaling and then immediately applies power to the heating coil. A very strong inhalation can however lead to the coil cooling down compared to a very mild inhalation. We detect the airflow speed or pressure drop over the air-pressure sensor and use that as an input to the microcontroller that controls the power delivered to the heating coil. We can therefore compensate for a very strong inhalation by applying more power during that inhalation as compared to a very light inhalation. This ensures that the heating coil is kept at its optimal heating temperature. This technique can be combined with other techniques designed to ensure the coil is at its optimal heating temperature, such as estimating coil resistance (which has been empirically mapped to coil temperature).

We can generalise this feature as follows:

An electronic cigarette vaporiser that includes a heating element and a microcontroller; in which the microcontroller monitors or measures the airflow speed or pressure drop over an air-pressure sensor or other sensor and uses that as an input to control the power delivered to the heating element.

Other optional features:

the microcontroller compensates for a very strong inhalation by applying more power during that inhalation as compared to a very light inhalation.

the microcontroller controls the power to ensure that the heating element is kept at its optimal heating temperature.

the vaporiser includes or co-operates with an electronics module that (i) detects characteristics of the resistance of the heating element and (ii) uses an inference of temperature derived from that resistance as a control input.

the temperature of the heating element is inferred from data stored in the electronics module that has been empirically obtained for a specific heating element design.

the microcontroller applies multiple techniques designed to ensure the heating element is at its optimal heating temperature, including estimating heating element resistance, and weights the signals from each technique.

the electronics module controls the power delivered using the resistance measurement and does not calculate any derived temperature.

the electronics module controls the power delivered to the heating element to ensure that it is no higher than approximately 130° C., plus an error tolerance.

the electronic vaporiser system is an e-cigarette system.

the electronic vaporiser is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 14: Using Data from the Cartridge that Defines the Type of e-Liquid to Control the Heating of the Coil Different e-liquids have different optimal temperatures for vaping; for example, the water content can have a significant impact on the optimal and maximum temperatures the heating coil should reach for the best flavor and also to ensure that there is no significant risk of harmful products in the vapour. Conventional electronic vaporisers cannot automatically vary the temperature reached by their heating coils to take this into account. Our system can.

We can generalise this feature as follows:

An electronic cigarette vaporiser that includes a heating element for heating an e-liquid and a microcontroller; in which the microcontroller determines the type and/or characteristics of the e-liquid being used and uses that as an input to automatically control the power delivered to the heating element to heat the e-liquid in a manner suitable for that specific type of e-liquid, or e-liquid with those characteristics.

Other optional features:

the e-liquid is supplied from a cartridge and that cartridge includes a record of the type of e-liquid stored in the cartridge and/or its characteristics and the microcontroller reads that record or is provided data from that record.

the cartridge includes a memory that stores the type of e-liquid the cartridge has been filled with and/or its characteristics and the vaporiser or a case into which the cartridge is inserted can read-off that data from the memory.

a variable for the type of e-liquid is the water content of the substance the vaporiser includes or co-operates with an electronics module that (i) detects characteristics of the resistance of the heating element and (ii) uses an inference of temperature derived from that resistance as a control input.

the temperature of the heating element is inferred from data stored in the electronics module that has been empirically obtained for a specific heating element design.

the electronics module applies multiple techniques designed to ensure the heating element is at its optimal heating temperature, including estimating coil resistance, and weights the signals from each technique.

the electronics module controls the power delivered using the resistance measurement and does not calculate any derived temperature.

the electronics module controls the power delivered to the heating element to ensure that it is no higher than approximately 130° C., plus an error tolerance.

the electronic vaporiser system is an e-cigarette system and the substance is an e-liquid.

the electronic vaporiser system is a medicinally approved nicotine drug delivery system.

the electronic vaporiser is the same approximate size as a cigarette the electronic vaporiser is the same approximate size as a cigarette and includes no control buttons the electronic vaporiser is automatically activated when it detects that it has been withdrawn from a case that otherwise stores the vaporiser.

the electronic vaporiser has a square or rectangular cross-section with rounded corners and includes a long PCB inserted lengthwise into the vaporiser the electronic vaporiser has a squircle cross-section the electronic vaporiser is only re-fillable from a user-replaceable closed, e-liquid cartridge the cartridge stores a record of the type of substance it stores and/or its characteristics on a chip and the vaporiser reads that chip or is provided data from that chip.

the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is connected to, and filled with, e-liquid using a piezo-electric pump fluid transfer mechanism PV Feature 15: The PV has a Squircle Cross-Section As noted earlier, the PV is the approximate same size as an ordinary cigarette, approximately 10 cm in length and 1 cm in width. The cross-section is square, with rounded corners: this shape enables a long, rectangular circuit board to be included (a 'squircle') in the PV and gives more design freedom for the placement of that PCB: if the PV casing was circular, then the PCB would, if long, likely have to be mounted exactly across a diameter, and that would leave little room for a battery. So the square cross-section is a much better shape if a long PCB and battery is to be included inside the casing. Also the PV includes a narrow pipe to transport e-liquid from the filling end to the reservoir around the heating element; this pipe can be accommodated in the corner of the PV casing. Finally, the outer casing of the PV includes a series of small LEDs that be lit to show the amount of e-liquid that has been consumed, for example, mimicking the reducing length of a cigarette as it burns down—hence, with a full reservoir of e-liquid, the entire row of perhaps 5 or 6 LEDs would be illuminated; progressively fewer LEDs are lit as vaping progresses, until only the LED closest to the user's mouth is illuminated. The LEDs are mounted on a very narrow circuit board: this is cheaper if it is flat since that eases SMT (surface mount technology) manufacture of the LEDs on the PCB. It is also easier to fix a flat PCB against the flat surface of the PV, as opposed to a circular surface. The square-profiled tube with rounded corners is hence an effective shape for including these various elements.

We can generalise this feature as follows:

An electronic cigarette vaporiser that is the same approximate size as a cigarette and has a square or rectangular cross-section with rounded corners and includes a long PCB inserted lengthwise into the vaporiser.

Optional features:
the PCB is not mounted at the mid-point of the cross-section, but at a different position closer to a major face of the vaporiser to permit more room for a rechargeable battery the PCB is mounted close and running parallel to a main face of the vaporiser the cross-section is a squircle the vaporiser includes a narrow pipe to transport e-liquid from the filling end to the reservoir around the heating element and this pipe runs along one internal corner of the vaporiser.

the electronic vaporiser system is an e-cigarette system and the substance is an e-liquid.

the electronic vaporiser system is a medicinally approved nicotine drug delivery system.

the electronic vaporiser is the same approximate size and shape as a cigarette the electronic vaporiser is the same approximate size and shape as a cigarette and that vaporiser includes no control buttons.

the electronic vaporiser is automatically activated when it detects that it has been withdrawn from a case that otherwise stores the vaporiser.

the electronic vaporiser is only re-fillable from a user-replaceable closed, e-liquid cartridge the electronic vaporiser is refillable with e-liquid only when inserted, whole and intact and not dis-assembled, into a re-fill case that includes a fluid transfer mechanism to transfer e-liquid into the vaporiser from a user-replaceable closed, e-liquid cartridge the electronic vaporiser is, connected to, and filled with, e-liquid using a piezo-electric pump fluid transfer mechanism the electronic vaporiser is fillable only from a user-replaceable e-liquid cartridge the electronic vaporiser is refillable with e-liquid only when inserted, whole and intact and not dis-assembled, into a re-fill case that includes a fluid transfer mechanism to transfer e-liquid into the vaporiser PV Feature 16: Silicone Caps to the Ceramic Cell Heating elements are usually mass-manufactured by a company that specializes in making just these units; the fully assembled units are then supplied to the company manufacturing the vaporizer. The units are then inserted into the main body of the vaporizer on a manufacturing line. In order to minimize leakage of e-liquid from around the edge of the unit, it is normal for their mass-manufacturer to supply them wrapped in a thin layer of cotton material. This provides a seal around the unit, but the seal is not that effective, especially when the e-liquid is supplied under pressure, because the cotton becomes saturated quickly and then ceases to prevent leakage. The consequence is that the conventional design of a heating element wrapped in cotton is not satisfactory for our purposes.

Instead of cotton material, we provide a pair of silicone end-caps that fit over each end of the heating unit; the heating unit with its silicone end caps can then be press-fitted inside the body of the vaporizer; the silicone forms a tight seal around the unit and prevents unwanted leakage, even when e-liquid is being pumped into the reservoir surrounding the heating unit under pressure.

This approach is especially useful when a ceramic heating unit is used.

We can generalise as follows:

A heating or atomising unit for an electronic cigarette vaporiser, in which the unit includes a protective elastomer wall or barrier configured to enable (i) the unit to fit inside a body in the vaporiser and to prevent leakage around the outside of the unit whilst e-liquid is being supplied under pressure to a reservoir surrounding the unit and (ii) e-liquid to pass from the e-liquid reservoir outside of the unit and into the unit.

Optional features include:
the unit is a ceramic cell
the ceramic cell is cylindrical
the protective elastomer wall or barrier is a pair of end caps that fit over each end of the unit
a gap is formed between each end cap through which e-liquid can pass to reach the outer surface of the ceramic cell and then pass through the ceramic and into the atomizing chamber in the cell (where there is a heating element).
a cotton material is placed in the gap
The elastomer is chosen to have one or more (and preferably all) of the following properties: (i) form an effective seal around the ceramic unit; (ii) withstand high temperatures (e.g. in excess of 200 degrees C. or higher); (iii) will not introduce any toxic compounds into the e-liquid and (iv) is easy to mould around the unit
The elastomer is thermally insulating.
The elastomer is silicone
The elastomer is a rubber
The unit is generally cylindrical and the elastomer forms a thin wall or barrier around the curved surface of the cylinder
The elastomer forms a thin wall or barrier around one or both ends of the unit
The unit is a ceramic heating unit
The ceramic heating unit includes a cylindrical ceramic wicking material with a central, hollow bore, with a heating element formed around the central bore.
The unit is manufactured using an insert molding manufacture process
The unit is dropped into a round tool that is about 1 mm in radius greater than the radius of the unit and the elastomer is poured into the gap to form the wall or barrier
e-liquid passage holes are formed in the wall or the barrier at locations in the wall or barrier designed to provide controlled delivery of e-liquid Another feature is an electronic cigarette vaporizer including a heating or atomising unit as defined above.

Note: for each of the generalisations given above, we have focused on an electronic cigarette vaporiser. It would be possible in each case to generalise further to an electronic vaporiser—i.e. a vaporiser that is not limited to enable nicotine to be inhaled, but other substances, including medicines.

Miscellaneous Features

In this section, we list various miscellaneous features that are present in the vaping system.

Misc. 1:

The PV includes an oleophobic barrier separating the vaporising chamber from the portion of the PV containing the electronics and battery: The PV includes a washer or other form of barrier that permits air to pass but not e-liquid; the barrier separates the portion of the PV including the battery and the electronics from the portion of the PV which e-liquid or vapour comes into contact with. The washer/barrier could have no moving parts, but instead be made of an air-porous material, such as a sintered polymer or metal, coated with or otherwise including a layer or barrier of a substance that is air-porous but not porous to e-liquid, such as an oleophobic material or a hydrophobic or super-hydrophobic material. Examples of suitable oleophobic materials are sintered phosphor bronze, sintered stainless steel, sintered PU plastic.

Misc. 2:

PV has replaceable covers: The PV includes a user replaceable cover to enable customizing of the appearance of the PV. The cover may be a clip on cover.

Misc 3:

PV magnetically latches in the case. The PV, or the chassis that holds the PV in the case, is magnetically latched into the case (e.g. one or more magnets are placed somewhere on the PV or the chassis so that the charging and/or data contacts on the PV latch reliably to their corresponding contacts in the case). For example, a small neodymium magnet in the case and a matching magnet or metal item in the PV (or vice versa) ensure that, when the PV is nearly fully inserted into the case, the PV is drawn in the rest of the way to a secure, final position, which is also the position needed for fluid transfer from a parent e-liquid reservoir (e.g. the e-liquid cartridge that slots into the case) to a child reservoir in the PV.

The charging and data transfer contacts in the PV and the case are optimally and securely positioned in contact with one another. The magnets stop the PV from falling out of the case if the case is tipped upside down and also eliminate contact bounce—i.e. when the PV is dropped into the case. Furthermore, they ensure that the fluid transfer mechanism is correctly positioned (e.g. the filling aperture or nozzle in the PV is correctly lined up with the filling stem or nozzle from the cartridge or other form of parent reservoir). In one implementation, one or more small magnets near to the battery and data contacts ensure that the corresponding battery and the data contacts in the PV and case magnetically latch to one another when the PV is fully inserted into the case or the chassis part of the case that holds the PV; the magnets do not need to be placed near to the contacts but can be positioned anywhere suitable, for example, either at one end of the PV, or alternatively are positioned somewhere along the main body of the PV.

Whilst magnetically securing the charging contacts in a PV against the power electrodes in a charging case is known, it is not known to use magnetic latching to ensure that not only are the power contacts correctly and reliably positioned in relation to each other, but so also are the data contacts and the fluid transfer mechanism. Magnetic latching can be applied to any one or more of the following: the power contacts, the data contacts, the fluid transfer mechanism. When applied directly to say just the power contacts (e.g. only the power electrodes have adjacent magnets), then the data contacts and the fluid transfer mechanism can be taken into correct alignment anyway, so it is not necessary to have multiple magnets in the PV or case.

Equally, a small neodymium magnet in the case and a matching magnet or metal item in the hinged chassis described earlier (or vice versa) ensure that, when the chassis is nearly fully closed, the chassis is drawn in the rest of the way to a secure, final position, which is also the position needed for fluid transfer from a parent e-liquid reservoir (e.g. the e-liquid cartridge that slots into the case) to a child reservoir in the PV. This again eliminates contact bounce, gives a good tactile feel to closing the chassis into the case, and ensures that the power and data connections are properly aligned.

Misc. 4:

The replaceable tip of the PV includes its own integral atomising heating element and is separable from the e-juice reservoir in the PV. (Cartomizers could be said to include a replaceable tip with a heating element, but they include the e-juice reservoir).

Misc. 5:

PV has a heated nozzle: Those parts of the PV (especially the nozzle) on which e-liquid vapour might otherwise condense if those parts of the nozzle were cold, are heated using e.g. an electrical heating element. Condensation of the e-liquid vapour on internal components of the PV is a problem if those condensed droplets can trickle into the user's mouth. If those components are heated (e.g. using an electrical heating coil in thermal connection with the component(s)), then the possibility of condensation forming can be reduced. Heating the components can also be used to warm the e-liquid vapour to a desired temperature; this is especially useful if atomisation of the e-liquid arises using a non-heating system, such as ultrasonic atomisation using piezo-electric or other form of droplet-on-demand system.

Misc. 6

The cartridge includes a piezo-electric pump to transfer small but accurately and reliably metered quantities of e-liquid: the piezo-electric pump can be used as the fluid transfer mechanism to transfer e-liquid from the cartridge or parent reservoir into the child reservoir in the PV. It can also be used in reverse to suck back out any residual e-liquid in the PV. Because the amounts delivered can be accurately metered, this means that the PV (or case or associated application running on a Smartphone) can accurately determine the total consumption of e-liquid and/or the amount of e-liquid remaining in a cartridge and also in the PV itself. This in turn can be used in the automatic re-ordering function—for example, when the system knows that the cartridge is down to its last 20% by volume of e-liquid, then the app running on the user's smartphone can prompt the user with a message asking if the user would like to order a replacement cartridge or cartridges. Low-cost piezo-electric pumps used ordinarily for delivering ink in an inkjet printer may be used.

Misc. 7:

Atomiser is integrated into a removable lid or cap to the cartridge—when the PV engages with the lid/cap, the lid/cap is filled with a small quantity of e-liquid and locks onto the PV; so when the PV is lifted up, the lid is locked into to one end. Hence, every cartridge comes with its own atomizer.

Misc. 8:

The cartridge can be packaged into a container that is the same size as a conventional cigarette pack: this enables distribution through existing cigarette vending machines and point of sale systems.

Misc 9:

The case is the same size as a cigarette pack: the case, or its packaging, is the same size as a conventional cigarette pack (e.g. a pack of twenty cigarettes)—e.g. this enables distribution through existing cigarette vending machines and point of sale systems.

Misc 10.

Case includes a removable cover: Case includes a removable, e.g. a clip-on, cover or decorative panel(s) to enable a user to customize appearance; the main side faces of the case can be removed and a new face press-fitted into position.

Misc 11.

PV includes the removable cartridge and a mechanical sealing valve: The PV includes a removable e-liquid cartridge that slots into or attaches directly to the PV, without the need for a separate re-fill and re-charge case; a fluid transfer mechanism transfers e-liquid from the cartridge to a child reservoir in the PV; that child reservoir feeds e-liquid to a separate atomising unit (i.e. the child reservoir is separate from the atomising unit but feeds e-liquid to it via, for example, channels or some other mechanism). The cartridge is similar in structure to the cartridge described elsewhere in this specification but is not meant for insertion into a re-fill/re-charge case. The e-liquid cartridge is an air-tight, closed unit that cannot be re-filled by a user. The filling or fluid transfer mechanism is similar too: a micropump in the cartridge is activated by moving the cartridge relative to the rest of the PV to transfer e-liquid from the cartridge to a child reservoir in the PV. The PV includes the mechanical valve described above as that is lifted off its seat by when the stem or nozzle of the filling device or cartridge is introduced; this valve prevents leakage of any e-liquid during or after filling the PV child reservoir. The cartridge can remain inside or attached to the PV whilst the PV is being vaped. The PV can include any of the other features listed above. The cartridge includes some form of air pressure equalisation as otherwise, when the fluid volume diminishes, a partial vacuum will develop behind the fluid retarding it's transfer. However if a bellows type of cartridge is employed the lost volume is automatically compensated for. The cartridge can include any of the other features listed above.

Misc 12.

E-liquid is transferred out of the parent reservoir using a piston or other device that decreases the internal volume of the parent reservoir: A cartridge or other form of parent reservoir stores e-liquid; a plunger, piston or other means of reducing the internal volume of the parent reservoir is activated and as the internal volume decreases, e-liquid is forced out of a nozzle into a child reservoir in the PV. A foil cap seals the nozzle prior to use and is penetrated by a hollow spigot or tube when the cartridge is inserted into the device for filling a PV (the device could be a case or the PV itself).

The plunger, or piston etc could be forced forwards using a screw being turned within a thread inside the reservoir and directly pushing the plunger or piston forward, or a rack and pinion system in which the user turns a thumbwheel as the pinion, which causes the plunger, connected to the rack that is forced forwards as the thumbwheel is turned.

Similarly, there could be a rotary end cap, mounted on a thread external to the reservoir; when the end cap is turned, it drives the plunger or piston forwards.

The plunger, or piston etc could also be forced forwards using a rotary cam; rotating an end-cap causes a cam follower to push linearly forward against the plunger/piston, forcing that forward.

The plunger, or piston etc could also move forward inside a tube or other device and be connected to an outer collar or other device that sits outside of the tube and can be moved forward along a slot in the tube; as the user drags the collar forward along the slot, the plunger is also forced forwards. The outer collar could also be mounted on a thread so that rotating the collar causes it to move forward along the thread, moving the plunger forward as it does so.

Alternatively, the plunger, or piston could include a magnet (e.g. formed as a collar or other device) and then another magnet (e.g. formed as an outer collar that sits outside the magnetic collar on the plunger) could move forward, forcing the magnetic collar on the plunger forward. The outer magnetic collar could be mounted on a thread, so that turning the outer magnetic collar takes it forward along the thread and hence also takes the internal magnetic collar and the plunger forward too, decreasing the volume of the chamber and forcing e-liquid out.

In all of the above cases, the piston or plunger moves forward. But equally, the plunger could remain fixed, with the body of the parent reservoir moving in a direction to reduce the internal volume of the parent reservoir. This approach is especially relevant where the parent reservoir is inserted directly into the PV, and not a separate re-fill/re-charge case.

Also, the plunger or piston can force the e-liquid out of an aperture in the parent reservoir at the end of the cartridge facing the plunger, or anywhere else as well—for example, the aperture could be in a stem or nozzle that passes through the plunger.

Misc 13.

E-liquid is transferred out of a deformable parent reservoir: A cartridge or other form of parent reservoir stores e-liquid; it is connected to a chamber, such as a bellows, whose internal volume can be increased, sucking in e-liquid from the parent reservoir, and then decreased, expelling e-liquid into a child reservoir in the PV. There is a one-way valve at each end of the chamber; one valve opens when the other closes. So for example, the valve at the cartridge/parent end of the chamber opens to fill the chamber, whilst the valve at the other end remains closed. If the chamber is compressed, then the valve at the cartridge/parent end of the chamber shuts, and the valve at the other end opens, enabling fluid to be transferred to a child reservoir in the PV.

The chamber could be formed for example as a bellows (e.g. made of silicone), with folds or ridges that move apart when the chamber is expanding and move closer together when the chamber is contracting.

The chamber could be a simple deformable tube, e.g. a rubber tube; squeezing the tube squirts e-liquid out from the chamber; allowing the tube to regain its shape causes e-liquid to be sucked into the tube from the parent. Again, there is a one-way valve at each end of the chamber; one valve opens when the other closes. Another variant, which removes the need for one-way valves at each end, is a rotating pump with lobes or vanes that, as they rotate, force e-liquid through the tube.

Misc 14.

Archimedes screw: A cartridge or other form of parent reservoir stores e-liquid; an Archimedes screw inside the reservoir, when turned, transfers e-liquid through the reservoir & out of a nozzle at one end to the child reservoir in the PV.

Misc 15.

Gravity feed: A cartridge or other form of parent reservoir stores e-liquid; a gravity-based fluid transfer mechanism could be used to transfer e-liquid from the parent to a child reservoir in the PV. Air pressure equalisation can be achieved by using an air vent that allows air to enter the reservoir as fluid leaves it, but to prevent leakage or passage of any e-liquid. For example, the vent could have no moving parts, but instead be an air-porous material, such as a sintered polymer or metal, coated with a layer or barrier of a substance that is air-porous but not porous to e-liquid, such as an oleophobic material or a hydrophobic material. Various form factors for the cartridge/reservoir are possible, such as a concentric ring shaped to fit around the PV; a spiral tube that wraps around the PV; a serpentine or matrix tube that wraps around the PV.

The invention claimed is:

1. An electronic cigarette vaporiser system that includes a case and an electronic vaporiser that is stored in the case, and a heating element in the electronic vaporiser, wherein the system includes a non-contact sensor that detects release or withdrawal of the vaporiser from the case, in which the electronic vaporiser system includes (i) a user-replaceable, e-liquid cartridge that is attached to or integral with at least a part of the system, but is not user-refillable and includes no heating element; and (ii) an e-liquid reservoir that is separate from the user-replaceable e-liquid cartridge; and (iii) an electric or electronic pump that is configured to withdraw e-liquid from the user-replaceable e-liquid cartridge and pump pressurised e-liquid to the e-liquid reservoir; and wherein the heating element is not in the user-replaceable e-liquid cartridge but is instead in, or in e-liquid communication with, the e-liquid reservoir.

2. The electronic vaporiser system of claim 1 in which when withdrawal of the vaporiser is detected, then a vaporiser electronic circuitry changes state.

3. The electronic vaporiser system of claim 2 in which the vaporiser changes state to a ready mode.

4. The electronic vaporiser system of claim 3 in which the vaporiser changes state to a ready or pre-heating mode in which an inhalation detector is activated.

5. The electronic vaporiser system of claim 2 in which the vaporiser changes state to a heating mode, in which an atomising unit is at least partly activated.

6. The electronic vaporiser system of claim 5 in which when withdrawal of the vaporiser from the case is detected by the vaporiser or the vaporiser receives data indicating that the vaporiser has been withdrawn from the case, the vaporiser system automatically starts heating the atomizing unit so that the vaporiser is at its optimal operational temperature when the user takes his first vape.

7. The electronic vaporiser system of claim 1 in which the case includes some or all of the non-contact sensor.

8. The electronic vaporiser system of claim 1 in which the vaporiser includes some or all of the non-contact sensor.

9. The electronic vaporiser system of claim 1 in which the sensor is a non-contact magnetic sensor that detects when the vaporiser enters and leaves the case by sensing the presence, proximity or movement of a small magnet or strip of metal in the vaporiser or some other mechanism for disrupting the local magnetic field around the sensor.

10. The electronic vaporiser system of claim 9 in which the non-contact magnetic sensor is a reed switch, or Hall effect sensor.

11. The electronic vaporiser system of claim 8 in which a light sensor in the vaporiser detects when light is incident on the vaporiser, inferring that the vaporiser is now in an open case or no longer in the case at all.

12. The electronic vaporiser system of claim 7 in which the case includes a small LED light source and sensor; the LED is illuminated when the vaporiser is in the case and light reflected from the vaporiser is detected by the sensor; withdrawal of the vaporiser triggers the light sensor since light is no longer reflected off the vaporiser into the sensor.

13. The electronic vaporiser system of claim 1 in which the non-contact sensor is an IMU (inertial measurement unit) in the vaporiser.

14. The electronic vaporiser system of claim 1 in which the case re-fills the vaporiser with e-liquid and re-charges a battery in the vaporiser.

15. The electronic vaporiser system of claim 1 which is a medicinally approved nicotine drug delivery system.

16. The electronic vaporiser system of claim 1 in which the electronic vaporiser includes no control buttons that could impede smooth ejection from the case.

17. The electronic vaporiser system of claim 1 in which the electronic vaporiser has a square or rectangular cross-section with rounded corners and includes a long PCB inserted lengthwise into the vaporiser.

18. The electronic vaporiser system of claim 1 in which the electronic vaporiser is filled from the user-replaceable e-liquid cartridge.

19. The electronic vaporiser system of claim 1 in which the electronic vaporiser is refillable with e-liquid only when inserted, whole and intact and not dis-assembled, into the case and the case includes a fluid transfer mechanism to transfer e-liquid into the vaporiser.

20. The electronic vaporiser system of claim 1 in which the case includes the electric or electronic pump.

21. The electronic vaporiser system of claim 1 in which the electronic vaporiser includes the electric or electronic pump and the user-replaceable cartridge is removably insertable or integral to the vaporiser.

22. The electronic vaporizer system of claim 1, further comprising a structure that is configured to enable excess air-pressure arising from the pressured e-liquid to escape from the e-liquid reservoir and that is non-porous to the pressurized e-liquid.

23. The electronic vaporiser system of claim 1, in which the pump is in a desktop station.

* * * * *